US012797372B2

(12) United States Patent
Buhrlage et al.

(10) Patent No.: US 12,797,372 B2
(45) Date of Patent: Nov. 17, 2026

(54) SMALL MOLECULE INHIBITION OF DEUBIQUITINATING ENZYME JOSEPHIN DOMAIN CONTAINING 1 (JOSD1) AS A TARGETED THERAPY FOR LEUKEMIAS WITH MUTANT JANUS KINASE 2 (JAK2)

(71) Applicant: DANA-FARBER CANCER INSTITUTE, INC., Boston, MA (US)

(72) Inventors: Sara Buhrlage, Somerville, MA (US); James Griffin, Boston, MA (US); Ellen Weisberg, Boston, MA (US); Jing Yang, Boston, MA (US); Xiaoxi Liu, Boston, MA (US); Robert Magin, Boston, MA (US); Bin Hu, Boston, MA (US); Wai Cheung Chan, Boston, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 358 days.

(21) Appl. No.: 18/580,469

(22) PCT Filed: Jul. 25, 2022

(86) PCT No.: PCT/US2022/074110

§ 371 (c)(1),
(2) Date: Jan. 18, 2024

(87) PCT Pub. No.: WO2023/009982

PCT Pub. Date: Feb. 2, 2023

(65) Prior Publication Data

US 2024/0335427 A1 Oct. 10, 2024

Related U.S. Application Data

(60) Provisional application No. 63/225,773, filed on Jul. 26, 2021.

(51) Int. Cl.

| | |
|---|---|
| ***A61K 31/428*** | (2006.01) |
| ***A61K 45/06*** | (2006.01) |
| ***A61P 35/02*** | (2006.01) |
| ***C07D 401/12*** | (2006.01) |
| ***C07D 401/14*** | (2006.01) |
| ***C07D 403/12*** | (2006.01) |
| ***C07D 403/14*** | (2006.01) |
| ***C07D 413/12*** | (2006.01) |
| ***C07D 413/14*** | (2006.01) |
| ***C07D 417/12*** | (2006.01) |
| ***C07D 417/14*** | (2006.01) |
| ***C07D 471/04*** | (2006.01) |
| ***C07D 487/04*** | (2006.01) |
| ***C07D 513/04*** | (2006.01) |

(52) U.S. Cl.

CPC ............ *A61K 31/428* (2013.01); *A61K 45/06* (2013.01); *A61P 35/02* (2018.01); *C07D 401/12* (2013.01); *C07D 401/14* (2013.01); *C07D 403/12* (2013.01); *C07D 403/14* (2013.01); *C07D 413/12* (2013.01); *C07D 413/14* (2013.01); *C07D 417/12* (2013.01); *C07D 417/14* (2013.01); *C07D 471/04* (2013.01); *C07D 487/04* (2013.01); *C07D 513/04* (2013.01)

(58) Field of Classification Search

CPC ....... A61K 31/428; A61K 45/06; A61P 35/02; C07D 401/12; C07D 401/14; C07D 403/12; C07D 403/14; C07D 413/12; C07D 413/14; C07D 417/12; C07D 417/14; C07D 471/04; C07D 487/04; C07D 513/04

See application file for complete search history.

(56) References Cited

U.S. PATENT DOCUMENTS

| | | | | |
|---|---|---|---|---|
| 2017/0095457 A1 | 4/2017 | Lonergan et al. | | |
| 2017/0247365 A1 | 8/2017 | Jones et al. | | |
| 2020/0063114 A1 * | 2/2020 | Fauser | .................. | C12N 15/63 |

FOREIGN PATENT DOCUMENTS

| | | |
|---|---|---|
| WO | 2016046530 A1 | 3/2016 |
| WO | 2016156816 A1 | 10/2016 |
| WO | 2017009650 A1 | 1/2017 |
| WO | 2018065768 A1 | 4/2018 |

OTHER PUBLICATIONS

Hasserjian, Acute myeloid leukemia: advances in diagnosis and classification (International Journal of Laboratory Hematology, 2013, 35, 358-366) (Year: 2013).*

Murphy et al. Cytarabine and daunorubicin for the treatment of acute myeloid leukemia (Expert Opinion on Pharmacotherapy, 2017, 18(16) 1765-1780). (Year: 2017).*

Scott, The JAK2 exon 12 mutations (American Journal of Hematology, Critical Review, 2011, 668-676). (Year: 2011).*

Pubchem, SID 312991685, Available Date: Apr. 9, 2016 [retrieved on Oct. 11, 2022], Retrieved from the Internet <URL:https://pubchem.ncbi.nlm.nih.gov/substance/312991685>, 8 pages.

Wang et al., "JOSD1 Negatively Regulates Type-I Interferon Antiviral Activity by Deubiquitinating and Stabilizing SOCS1," Viral Immunology, vol. 30, No. 5, pp. 342-349, 2017.

* cited by examiner

*Primary Examiner* — Kamal A Saeed
*Assistant Examiner* — Meghan C Heasley
(74) *Attorney, Agent, or Firm* — ArentFox Schiff LLP; Daniel W. Clarke; Shawn P. Foley

(57) ABSTRACT

Disclosed are deubiquitinase (DUB) JOSD1 inhibitors and methods of treating a disease or disorder mediated by dysregulated Janus Kinase 2 (JAK2) activity, in a subject in need thereof, comprising administering a therapeutically effective amount of one or more DUB inhibitors.

15 Claims, 31 Drawing Sheets

Specification includes a Sequence Listing.

1

2

FIG. 4A
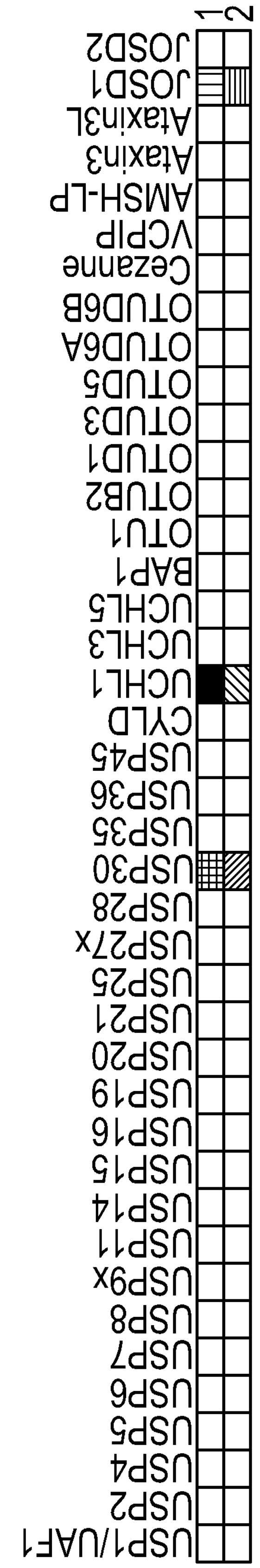
FIG. 4B
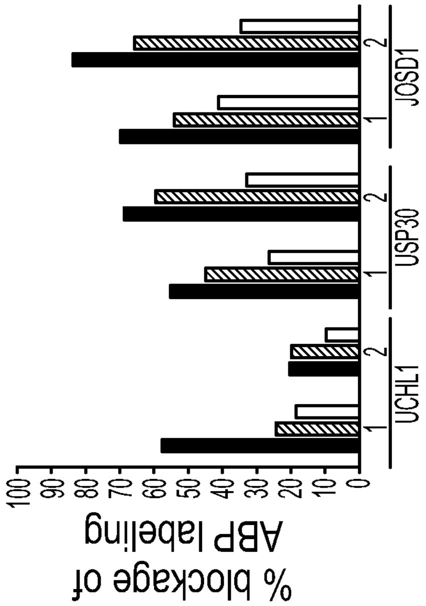
FIG. 4C
| | IC$_{50}$ (nM) | | |
|---|---|---|---|
| | UCHL1 | USP30 | JOSD1 |
| 1 | 400 | 400 | 324 |
| 2 | 168 | 390 | 134 |
FIG. 4D
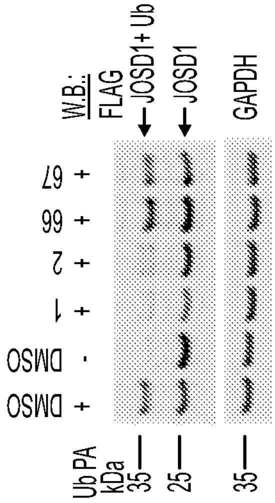

JAK2-V617F
FLAG-JOSD1
pcDNA3
FLAG-pcDNA3
1 2 3
Pull-down FLAG
INPUT
kDa
130
25
35
W.B.:
JAK2
FLAG
GAPDH Pull-down FLAG
MOCK
FLAG-JOSD1
INPUT HEL
IP-JAK2
IP-JOSD1
IP-IgG
INPUT
IP-JOSD1
JOSD1

SET-2

F/H-JOSD1
F/H-pcDNA3
1 2 3 4 5 6 7 8
+++
IB-JAK2
IB-FLAG
IB-GAPDH

FIG. 9C
FIG. 9D
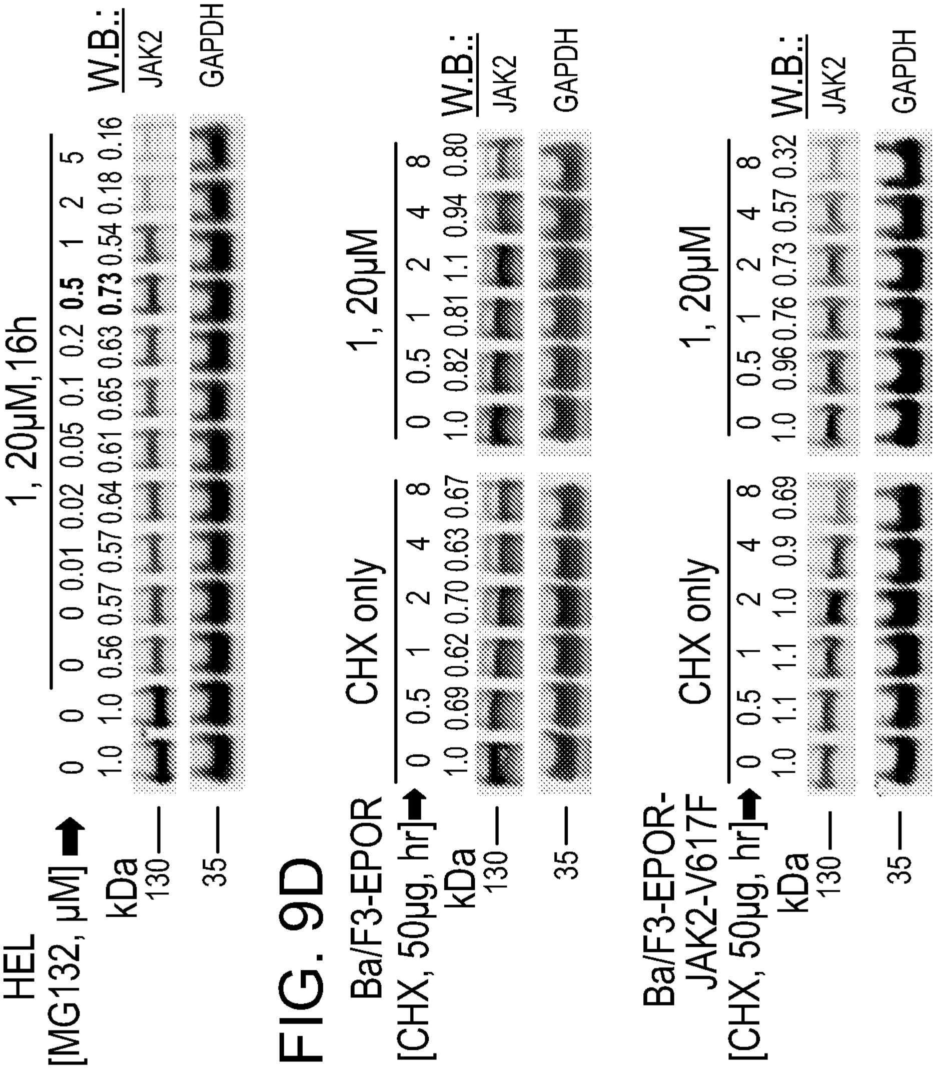
FIG. 9E
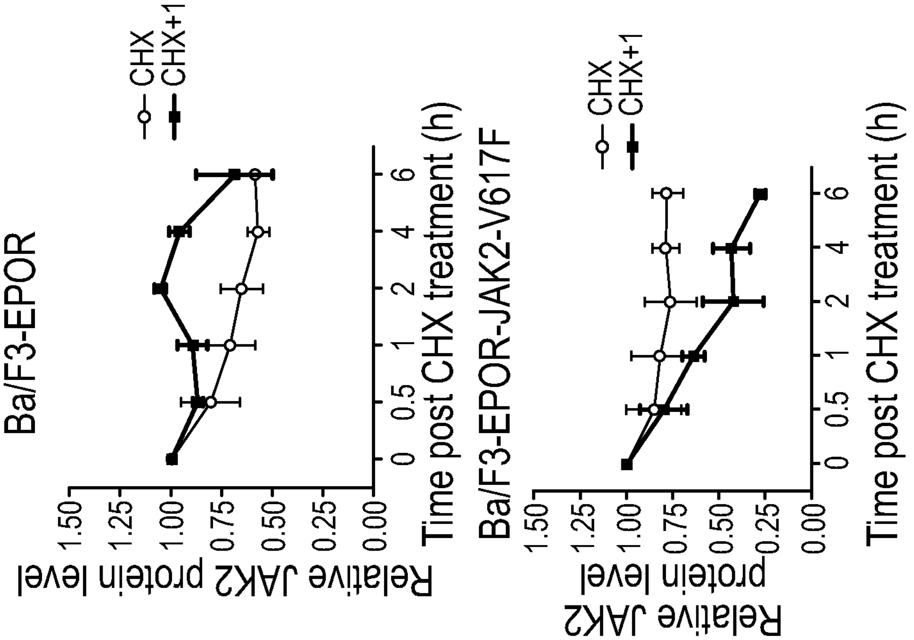

1

IC50 = 324 nM

2

IC50 = 134 nM kDa
25
55
35
HEK-293T
SKM-1
Ba/F3-V617F
HEL
SET-2
W.B.:
UCHL1
USP30
GAPDH
HEL SET-2
W.B.:
USP30
UCHL1
JOSD1
GAPDH

HEL
Comp.
24h [μM]
kDa
130
35
SB1-F-78
0 5 10 20
MF-094
0 5 10 20
W.B.:
JAK2
GAPDH
SET-2
Comp.
24h [μM]
kDa
130
35
SB1-F-78
0 5 10 20
MF-094
0 5 10 20
W.B.:
JAK2
GAPDH HEL
kDa
130
55
35
SCR
KO-USP30
T1 T2 T3
W.B.:
JAK2
USP30
GAPDH FIG. 15D
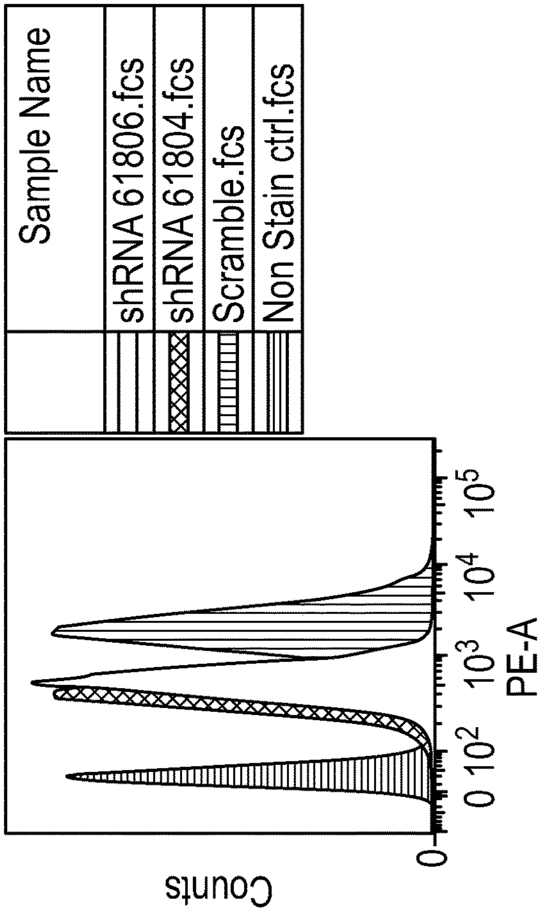
FIG. 15C
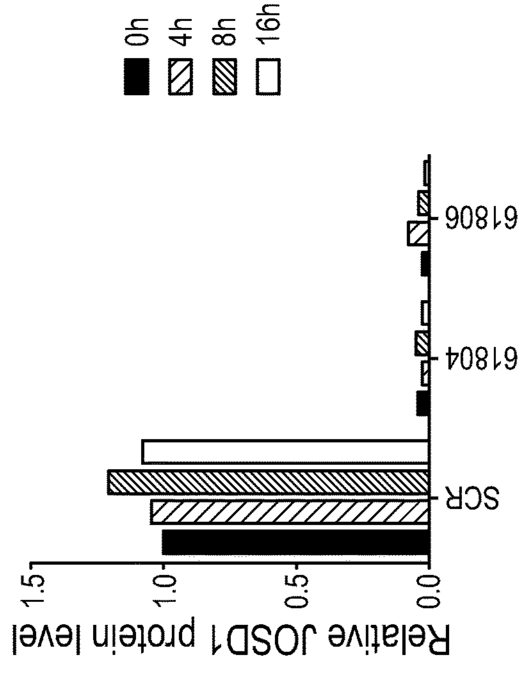
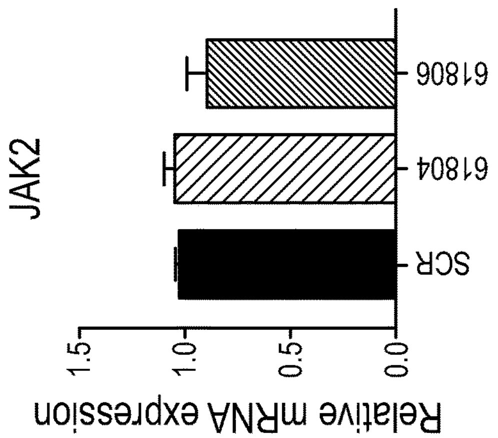
FIG. 15E FIG. 16A
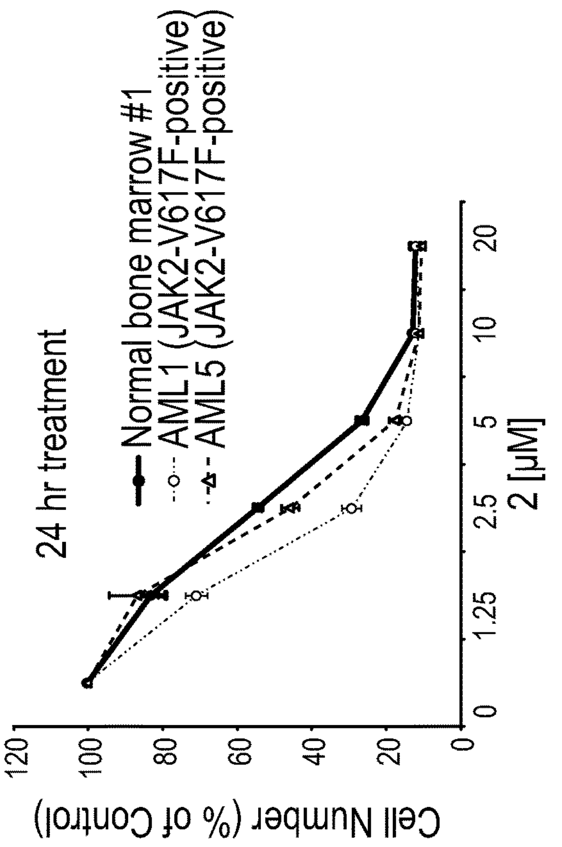
FIG. 16B
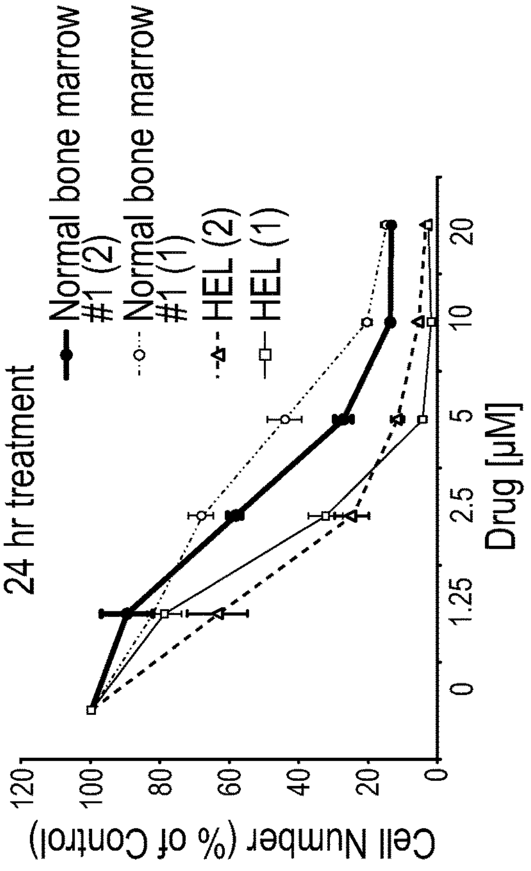
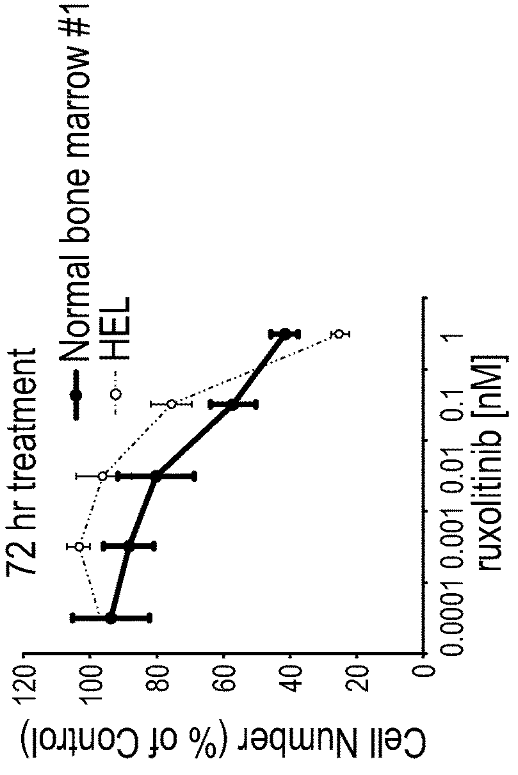
FIG. 16C

SMALL MOLECULE INHIBITION OF DEUBIQUITINATING ENZYME JOSEPHIN DOMAIN CONTAINING 1 (JOSD1) AS A TARGETED THERAPY FOR LEUKEMIAS WITH MUTANT JANUS KINASE 2 (JAK2)

RELATED APPLICATIONS

This application is a national stage application, filed under 35 U.S.C. § 371, of International Application No. PCT/US2022/074110, filed Jul. 25, 2022, which claims the benefit of priority under 35 U.S.C. § 119 (e) to U.S. Provisional Application No. 63/225,773, filed Jul. 26, 2021, each of which is incorporated herein by reference in its entirety.

GOVERNMENT LICENSE RIGHTS

This invention was made with government support under grant number R01CA233800 awarded by the National Institute of Health (NIH). The government has certain rights in the invention.

SEQUENCE LISTING

The instant application contains a Sequence Listing which has been submitted electronically in XML format and is hereby incorporated by reference in its entirety. Said XML copy, created on Jul. 21, 2022, is named 52095-741001WO_ST.xml and is 1.9 KB bytes in size.

BACKGROUND

Mutations in the Janus Kinase 2 (JAK2) gene resulting in constitutive kinase activation represent the most common genetic event in myeloproliferative neoplasms (MPNs), a group of diseases involving overproduction of one or more kinds of blood cells, including red cells, white cells, and platelets. JAK2 kinase inhibitors, such as ruxolitinib, provide clinical benefit, but inhibition of wild-type (wt) JAK2 limits their clinical utility due to toxicity to normal cells, and small molecule inhibition of mutated JAK2 kinase activity can lead to drug resistance.

The JAK2 gene encodes a non-receptor tyrosine kinase that is important for promoting hematopoietic cell growth and division in bone marrow. Wild-type (wt) JAK2 is activated after hematopoietic cytokines, such as erythropoietin and thrombopoietin, bind to their unique cell surface receptors, resulting in activation of downstream signaling proteins such as those constituting the JAK-signal transducer and activator of transcription (STAT), mitogen-activated protein (MAP)-kinase, phosphoinositide 3-kinase (PI3K)/Protein kinase B (PKB or AKT), and mechanistic target of rapamycin (mTOR) pathways; these are important for functional hematopoiesis and result in a proliferative advantage of the affected cells (Gäbler, et al., 2013, JAK-STAT, 2(3):e25025; James, et al., 2005, Nature, 434(7037):1144-48).

Several activating mutations in JAK proteins have been described as underlying causes of various blood disorders. The JAK2 valine-to-phenylalanine (V617F) mutation, which destabilizes the fold of its JH2 domain and leads to JAK2 autophosphorylation and constitutive activation of downstream pathways, is the most frequently occurring mutation in MPNs (Baxter, et al., 2005 Lancet, 365(9464):1054-61; Kralovics, et al., 2005 N Engl J Med., 352(17):1779-90; Levine, et al., 2005, Cancer Cell, 2005, 7(4):387-97).

The JAK2V617F mutation has been described in other myeloid neoplasms as well, including myelodysplastic syndrome (MDS) and chronic myelomonocytic leukemia (CMML). With the MPNs, this mutation occurs in up to 98% of Polycythemia Vera (PV) patients, ~50-60% of Essential Thrombocythemia (ET) patients, and 50-60/6 of Primary Myelofibrosis (MF or PMF) patients (Campbell, et al., 2006 N Engl J Med., 355(23):2452-66).

An additional 5-10% of ET and MF patients have activating mutations in the thrombopoietin receptor (also known as Myeloproliferative Leukemia Protein, MPL) gene that indirectly leads to constitutive JAK2 activation (Pikman, et al., 2006 PLoS Med., 3(7):e270; Rumi, et al., 2013 Blood, 121(21):4388-95). Somatic insertions or deletions in exon 9 of calreticulin (CALR) have been identified in MPN patients without mutations in JAK2 or MPL; these mutations were detected in 67% and 88% of JAK2 wt ET and MF patients, respectively (Klampfl, et al., 2013, N Engl J Med., 369(25):2379-90; Imai, et al., 2017, Int J Hematol., 105(6):743-7). Mutant CALR binds to the thrombopoietin receptor, which leads to aberrant and constitutive activation of JAK2 kinase activity (Araki, et al., 2016 Blood, 127(10):1307-16).

Currently, JAK2 inhibitory drugs, including FDA-approved fedratinib (INREBIC®), provide some clinical benefit, however, both inhibit mutated JAK2 and wt JAK2, which leads to limited clinical effectiveness (Quintas-Cardama, et al., 2010, Blood, 115(15):3109-17; Verstovsek, et al., 2010, N Engl J Med., 363(12):1117-27; Vainchenker, et al., 2018, F1000Res., 7:82). Drug resistance is another challenge, due to insufficient inhibition of phosphorylation of the activation loop on JAK2-Y1007 (Meyer, et al., 2014, Clin Cancer Res., 20(8):2051-59; Koppikar, et al., 2012, Nature, 489(7414):155-59; Andraos, et al., 2012, Cancer Discovery, 2(6):512). Thus, an alternative therapeutic approach to selectively target mutated JAK2 without disrupting the activity of wt JAK2 and that is able to override the resistance that is observed with available JAK2 inhibitors is needed.

SUMMARY

The present disclosure is based upon the discovery that inhibition of the deubiquitinase (DUB), Josephin domain containing 1 (JOSD1) selectively blocks the function of the valine-to-phenylalanine (V617F) mutated JAK2, by allowing JAK2V617F to be naturally degraded by the internal cellular degradation mechanism triggered by high levels of JAK2 ubiquitination.

Accordingly, described herein are methods of treating a disease or disorder mediated by dysregulated JAK2 activity, in a subject in need thereof, comprising administering a therapeutically effective amount of one or more DUB inhibitors or stereoisomers or pharmaceutically acceptable salts thereof. In some embodiments, the DUB inhibitors are compounds 1 and 2, or a combination thereof. In some embodiments, wherein the JAK2 comprises a V617F mutation. In some embodiments, the disease to be treated is cancer. In some embodiments, the cancer is a myeloproliferative neoplasm (MPN), such as Polycythemia Vera (PV), Essential Thrombocythemia (ET), or Primary Myelofibrosis (ML). In some embodiments, the myeloproliferative neoplasm is myeloid neoplasm. In other embodiments, the myeloid neoplasm is myelodysplastic syndrome (MDS), JAK2-V617F-positive MDS, chronic myelomonocytic leukemia (CMML), or acute myeloid leukemia (AML).

In some embodiments, the one or more DUB inhibitors is co-administered with a therapeutically effective amount of an FDA approved chemotherapy (e.g., doxorubicin, daunorubicin, cytarabine, cladribine, fludarabine, mitoxantrone, etoposide, 6-thioguanine, methotrexate, azacytidine, and decitabine), or targeted therapy comprising a poly adenosine diphosphate-ribose polymerase (PARP) inhibitor (e.g., Olaparib (LYNPARZA®, rucaparib (RUBRACA®), niraparib (ZEJULA®), veliparib, talazoparib (TALZENNA®)), and/or a JAK2 inhibitor (e.g., ruxolitinib (JAKAFI®), fedratinib (INREBIC®), momelotinib, and baricitinib (OLUMIANT®)).

Also described herein are methods for reducing the activity of DUB in a cell, either in vivo or in vitro, comprising administering a therapeutically effective amount of one or more DUB inhibitors stereoisomers or pharmaceutically acceptable salts thereof.

Another aspect of the present disclosure is directed to compounds and pharmaceutically acceptable salts and stereoisomers thereof for DUB inhibition.

Another aspect of the present disclosure is directed to a pharmaceutical composition containing a therapeutically effective amount of one of more compounds of the present disclosure or a pharmaceutically acceptable salts or stereoisomers thereof, and a pharmaceutically acceptable carrier.

In another aspect of the present disclosure, methods of making the compounds are provided.

Disclosed herein is a strategy to target mutated JAK2 for degradation, using the cell's intracellular degradation machinery, with relative sparing of non-mutated JAK2. A chemical genetics screen was employed, followed by extensive selectivity profiling and genetic studies, to identify the deubiquitinase JOSD1 as a regulator of mutant JAK2. It was surprisingly discovered that JOSD1 interacts with and stabilizes JAK2-V617F, and inactivation of the DUB leads to JAK2-V617F ubiquitination and subsequent degradation by through the ubiquitination-proteasome pathway, thereby shortening its protein half-life. Moreover, targeting of JOSD1 led to death of JAK2-V617F-positive primary AML cells. These studies provide a new therapeutic approach to achieving selective targeting of mutated JAK2 signaling in MPN. Additional JAK2 mutations that may be targeted by the disclosure include JAK2 gene fusions with the TEL (translocation-Ets-leukemia or ETV6) (TEL-JAK2) and pericentriolar material 1 (PCM1) genes, and mutations in JAK exon 12.

BRIEF DESCRIPTION OF THE DRAWINGS

FIG. 1A is a schematic of chemical structures of compounds 1 and 2. FIG. 1B is a line graph showing the effects of compound 1 on Ba/F3 and Ba/F3-EPOR-JAK2-V617F cell proliferation. FIG. 1C is a line graph showing the effects of compound 2 on Ba/F3 and Ba/F3-EPOR-JAK2-V617F cell proliferation. FIG. 1D is a line graph showing the effects of compound 1 on proliferation of Ba/F3 cells engineered to express different oncogenes. FIG. 1E is a blot showing that Ba/F3-EPOR and Ba/F3-EPOR-JAK2-V617F cells were treated with compound 1 for 24 hours at different concentrations. JAK2 and GAPDH protein levels were detected by western blotting with indicated antibodies. FIG. 1F is a blot showing that Ba/F3-EPOR and Ba/F3-EPOR-JAK2-V617F cells were treated with compound 2 for 16 hours at different concentrations. JAK2 and GAPDH protein levels were detected by western blotting with indicated antibodies.

FIG. 2A is a series of blots showing the effect of compound 1 on JAK2 expression in JAK2-V617-positive HEL (upper panel), SET-2 (middle panel) and MUTZ-8 (lower panel) cells. FIG. 2B is a line graph showing the effect of compound 1 on JAK2-V617F-positive HEL or SET-2 cell proliferation versus normal PBMCs. FIG. 2C is a series of blots showing that the HEL cells were treated with compound 1 and compound 2 at 0, 5, 10, and 20 μM for 16 hours. JAK2 and GAPDH protein levels were detected by western blotting with the indicated antibodies. FIG. 2D is a blot showing that the HEL cells were treated with compound 1 for 24 hours at 0, 5, 10 and 20 IM. JAK2, p-MAPK, MAPK, p-STAT3, STAT3 and GAPDH protein levels were detected by western blotting with indicated antibodies. FIG. 2E a series of showing that the HEL cells were treated with compound 2 at 0 and 5 μM for 16 hours. Different proteins were detected by western blotting with the indicated antibodies. FIG. 2F is a blot showing that K562, KU812F and HEL cells were treated with compound 2 at 0 and 5 μM for 16 hours. JAK2 and GAPDH protein levels were detected by western blotting with the indicated antibodies.

FIG. 3A is bar graph showing that HEL cells were treated with compound 1 for 24 hours at 0, 5, 10 and 20 μM. RNA was isolated, and JAK2 mRNA levels were visualized by real-time PCR. mRNA expression was normalized using the housekeeping GAPDH gene as a loading control. Shown are the representative results of 3 independent experiments. FIG. 3B is a blot showing that HEL cells were pretreated with or without the proteasome inhibitor, MG132 (0.5 μM) for 2 hours. Following compound 1 treatment for 16 hours at 20 μM, JAK2 and GAPDH protein levels were detected by western blotting. FIG. 3C is a series of blots showing that HEL cells were treated with CHX (20 μg/ml) with or without compound 1 treatment (20 μM) at the indicated time points. JAK2 and GAPDH protein levels were detected by western blotting. FIG. 3D is a line graph showing that the half-life of JAK2 protein was quantified as shown. FIG. 3E is a series of blots showing that the HEL cells were treated with CHX (10 μg/ml) with or without compound 2 treatment (10 μM) at the indicated time points. JAK2 and GAPDH protein levels were detected by western blotting. FIG. 3F is a line graph showing that the half-life of JAK2 protein was quantified as shown. Shown are the representative results of 3 independent experiments.

FIG. 4A-FIG. 4D is a profiling panel, a bar graph, a table, and a blot showing the Deubiquitinase (DUB)ome selectivity profiling of compounds 1 and 2. FIG. 4A is a profiling panel showing the comprehensive selectivity profiling of compounds 1 and 2 utilizing purified enzyme biochemical assays and chemical proteomics. USP30, UCHL1 and JOSD1 were identified as targets. FIG. 4B is a bar graph showing the competitive activity-based protein profiling with quantitative mass spectrometry. JOSD1 was identified as a target of compounds 1 and 2 in HEK293 lysates. FIG. 4C is a table showing the biochemical $IC_{50}$ for compounds 1 and 2 against UCHL1, USP30, and JOSD1. FIG. 4D is a target engagement assay for JOSD1 in HEL-FLAG-HA-JOSD1 cells after 10-hour of treatment with compounds 1 and 2 (10 μM). Compounds 66 and 67 are included as a negative control. Compound 66, which although having a similar structure to compound 1, displays an $IC_{50}$>100 nM for JOSD1 and does not induce degradation of JAK2-V617F (data not shown). Also included as a negative control is Bin-01-18B, which displays an $IC_{50}$>100 nM for JOSD1.

FIG. 5A is a series of blots showing that IP was performed with FLAG IgG beads in HEK-293T cells with overexpressed JAK2 and FLAG-JOSD1. JAK2 and JOSD1 were detected both in IP and cell lysate (INPUT) by western blotting with the indicated antibodies. FIG. 5B is series of blots showing that IP was performed with FLAG IgG beads in HEL cells with over-expressed FLAG-JOSD1. JAK2 and JOSD1 were detected both in IP and cell lysate (INPUT) by western blotting with the indicated antibodies. FIG. 5C is a series of blots showing that Co-IP was performed in HEL with JAK2 and JOSD1 antibodies, with IgG used as a negative control. JAK2 and JOSD1 were detected both in IP and cell lysate (INPUT) by western blotting with the indicated antibodies. FIG. 5D is a blot showing that Co-IP was performed in SET-2 with JAK2 and JOSD1 antibodies, with IgG used as a negative control. JAK2 and JOSD1 were detected both in IP and cell lysate (INPUT) by western blotting with the indicated antibodies. FIG. 5E is a series of blots showing that HEK-293T cells were made to overexpress JAK2-V617F (0.5 μg) and FLAG-JOSD1 (0.5, 1 and 1.5 μg). JAK2 and JOSD1 were then detected by western blotting with the indicated antibodies.

FIG. 6A is a series of blots showing that JOSD1 was knocked down in HEL cells by introducing JOSD1-silencing puromycin-resistant short hair pin RNAs (shRNAs) (61804, 61806 or 376514) by lentiviral transduction. JAK2, JOSD1, STAT3, AKT and GAPDH protein levels were detected by western blotting with the indicated antibodies. FIG. 6B is a series of blots showing JOSD1 was knocked down in SET-2 cells by introducing JOSD1-silencing puromycin-resistant shRNAs (61804, 61806 or 376514) by lentiviral transduction. JAK2, JOSD1, STAT3, AKT and GAPDH protein levels were detected by western blotting with the indicated antibodies. FIG. 6C is a series of blots showing JOSD1 was knocked down in HEL MUTZ-8 cells by introducing JOSD1-silencing puromycin-resistant shRNAs (61804, 61806 or 376514) by lentiviral transduction. JAK2, JOSD1, STAT3, AKT and GAPDH protein levels were detected by western blotting with the indicated antibodies. FIG. 6D is a series of blots showing that the JOSD1 gene was knocked down in SET-2 cells. JAK2 IP was performed, and ubiquitin, JAK2, and GAPDH protein levels were detected both in IP and cell lysate (INPUT) by western blotting with indicated antibodies. FIG. 6E is a series of blots showing that JOSD1 was knocked down in SET-2 (JAK2-V617F) cells or K562 (wt JAK2) cell lines. JAK2, JOSD1 and GAPDH protein levels were detected by western blotting with the indicated antibodies. FIG. 6F is a series of blots and a bar graph showing that JOSD1 was knocked out in HEL cells by introducing JOSD1-silencing puromycin resistant Cas9-sgRNAs (#1 and #5) by lentiviral transduction. JAK2, JOSD1, STAT3, AKT and GAPDH protein levels were detected by western blotting with the indicated antibodies (top panel). mRNA levels of JOSD1 were detected by qPCR (bottom panel). FIG. 6G is a series of blots showing that JOSD1 was knocked out in the K562 (wt JAK2) cell line. JAK2, JOSD1 and GAPDH protein levels were detected by western blotting with the indicated antibodies. FIG. 6H is a series of blots showing that JOSD1 was knocked out in HEL cells by introducing JOSD1-silencing puromycin resistant Cas9-sgRNAs (1 and 5) by lentiviral transduction, and monoclonal cells (#5, #6 and #6) were selected. JAK family, JOSD1, downstream STAT signaling molecules and GAPDH protein levels were detected by western blotting with the indicated antibodies.

FIG. 7A is a line graph showing the treatment of primary JAK2-V617F-positive (secondary AML) samples with compound 2. FIG. 7B is a line graph showing the treatment of primary JAK2-V617F-positive (secondary AML) samples with ruxolitinib. FIG. 7C is a line graph showing compound 2 treatment of primary AML1 (de novo MPD/MDS) (JAK2-V617F-positive) and AML5 (secondary AML) (JAK2-V617F-positive) and normal donor-derived bone marrow cells (sample #1) (cultured in the presence of cytokines) for 72 hours. FIG. 7D is a line graph showing the treatment of normal bone marrow cells (sample #2) in the absence and presence of cytokines, AML12 (secondary AML) and HEL cells for 72 hours with compound 2 at the indicated concentrations. FIG. 7E is a line graph showing treatment of normal bone marrow cells (sample #2) in the absence and presence of cytokines, AML12 (secondary AML) and HEL cells for 72 hours with compound 1 at the indicated concentrations. FIG. 7F is a line graph showing treatment of normal bone marrow cells (sample #2) in the absence and presence of cytokines, AML12 (secondary AML) and HEL cells for 72 hours with ruxolitinib at the indicated concentrations. FIG. 7G is a bar graph showing the effects of compound 2 on normal bone marrow and primary AML colony formation. FIG. 7H is a bar graph showing the effects of compound 1 (H) on normal bone marrow and primary AML colony formation.

FIG. 8A is a series of blots showing that HEL cells were treated with compound 1 for 24 hours at 0, 0.5, 1, 5, 10 and 20 μM. JAK2 and GAPDH protein levels were detected by western blotting with the indicated antibodies. FIG. 8B is a series of blots showing that HEL cells were treated with compound 2 for 16 hours at 0, 0.05, 0.1, 0.5, 1, 5 and 10 μM. JAK2 and GAPDH protein levels were detected by western blotting with the indicated antibodies. FIG. 8C is a series of blots showing that HEL cells were treated with compound 2 for 16 hours at 0, 5, 10 and 20 μM, and JAK2, STAT5 and GAPDH protein levels were detected by western blotting with the indicated antibodies. FIG. 8D is a series of blots showing that K562, KU812F and HEL cells were treated with compound 2 at 0, 1.25, 2.5, 5 μM for 16 hours. Cells were collected, and protein was detected by western blotting with the indicated antibodies.

FIG. 9A-FIG. 9E is a series of blots and line graphs showing that compound 1 shortens JAK2-V617F protein half-life through ubiquitin-mediated proteasomal degradation. FIG. 9A is a series of blots showing that HEL cells were treated with compound 1 for 16 hours at 0, 10 and 20 μM. IP was performed with antibodies against JAK2, ubiquitin, and GAPDH and protein levels were detected both in IP and cell lysate (INPUT) by western blotting with the indicated antibodies. FIG. 9B is a series of blots showing that HEL cells were treated with compounds 2 for 16 hours at 0, 5 and 10 μM. IP was performed with antibodies against JAK2, ubiquitin, and GAPDH and protein levels were detected both in IP and cell lysate (INPUT) by western blotting with the indicated antibodies. FIG. 9C is a series of blots showing that HEL cells were pretreated with or without the proteasome inhibitor, MG132 (0-5 μM) for 2 hours. Following compound 1 treatment for 16 hours at 20 μM, JAK2 and GAPDH protein levels were detected by western blotting. FIG. 9D is a series of blots showing that Ba/F3-EPOR or Ba/F3-EPOR-JAK2-V617F cells were treated with CHX (50 μg/ml) with or without compound 1 treatment at 20 μM for different time points. JAK2 and GAPDH protein levels were detected by western blotting with the indicated antibodies. FIG. 8E is a series of line graphs showing that the half-life of JAK2 protein was quantified and plotted. Shown are the representative results of 3 independent experiments.

FIG. 10A is a profiling schematic showing comprehensive selectivity profiling of compounds 1 and 2 utilizing purified enzyme biochemical assays and chemical proteomics. USP30, UCHL1 and JOSD1 were identified as targets. FIG. 10B is a profiling chart showing competitive activity-based protein profiling with quantitative mass spectrometry. JOSD1 was identified as a target of compounds 1 and 2 in HEK293 lysates. FIG. 10C is a series of line graphs showing Biochemical $IC_{50}$ for compounds 1 and 2 against JOSD1.

FIG. 11 A FIG. 11F is a series of blots showing that HEL cells were treated with compound 2 at 0, 5, 10 and 20 μM for 16 hours. MCL-1 and GAPDH were detected by western blotting with the indicated antibodies.

FIG. 12A is a series of blots showing that IP was performed with FLAG IgG beads in HEK-293T cells with over-expressed JAK2 and FLAG-JOSD1. JAK2 and JOSD1 were detected both in IP and cell lysate (INPUT) by western blotting with the indicated antibodies. FIG. 12B is a series of blots showing that IP was performed with FLAG in cells with over-expressed FLAG-JOSD1 or mock. JAK2 and SOCS1 were detected both in IP and cell lysate (INPUT) by western blotting with the indicated antibodies. FIG. 12C is a series of blots showing that Co-IP was performed in HEL or SET-2 with JAK2 and JOSD1 antibodies, with IgG used as a negative control. JAK2 and JOSD1 were detected both in IP and cell lysate (INPUT) by western blotting with the indicated antibodies.

FIG. 13A is a series of blots showing that JOSD1 was knocked down in HEL cells by introducing JOSD1-silencing puromycin resistant shRNAs (61804, 61806 and 369909) by lentiviral transduction. JAK2, JOSD1, downstream STAT signaling and GAPDH protein levels were detected by western blotting with the indicated antibodies. FIG. 13B is a series of blots showing that the JOSD1 gene was knocked down in SET-2 cells. JAK2, JOSD1, downstream STAT signaling molecules and GAPDH protein levels were detected by western blotting with the indicated antibodies. FIG. 13C is a series of blots showing that the JOSD1 gene was knocked down in MUTZ-8 cells. JAK2, JOSD1, MCL-1 and GAPDH protein levels were detected by western blotting with the indicated antibodies. FIG. 13D is a series of blots showing that the JOSD1 gene was knocked down in HEL cells. JAK2, JOSD1, downstream STAT signaling molecules and GAPDH protein levels were detected by western blotting with the indicated antibodies. FIG. 13E is a series of blots showing that the JOSD1 gene was knocked down in HEL cells. RNA was isolated and JAK2 mRNA levels were visualized by real-time PCR. mRNA expression was normalized for the housekeeping gene GAPDH. Shown are the representative results of 3 independent experiments.

FIG. 14A is a line graph showing the comparison of growth of HEL shck and HEL sg EGFP (control) cells and HEL sg JOSD1 KO cells (monoclonal line 3-2) over time. FIG. 14B is a series of blots showing that the JOSD1 gene was knocked out in HEL cells. Antibodies against JAK2 and JOSD1 (C-terminal and N-terminal) were used to assess JOSD1 KO efficiency and JAK2 protein levels.

FIG. 15A-FIG. 15E is a is a series of blots, a line graph, a series of bar graphs, and a histogram showing knockdown of JOSD1 shortens JAK2-V617F protein half-life: SET-2 cells. FIG. 15A is a series of blots showing that the JOSD1 gene was knocked down in SET-2 cells by introducing JOSD1-silencing puromycin resistant shRNAs (61804 and 61806) by lentiviral transduction. After 3d puromycin selection, cells were picked out as monoclonal cells and expanded, then treated with CHX (20 μg/ml) for different time points. JAK2, JOSD1 and GAPDH protein levels were detected by western blotting with the indicated antibodies. FIG. 15B is a line graph showing that the half-life of JAK2 protein was analyzed as shown. FIG. 15C is a bar graph showing that the JOSD1 protein levels were analyzed as shown. FIG. 15D is a histogram showing that the JOSD1 was knocked down in SET-2 cells. Protein levels of JAK2 were detected by flow-cytometry with PE-staining. FIG. 15E is a bar graph showing that the JOSD1 gene was knocked down in SET-2 cells. RNA was isolated and JAK2 mRNA levels were visualized by real-time PCR. mRNA expression was normalized for the housekeeping gene GAPDH.

FIG. 16A-FIG. 16C is a series of line graphs showing the effects of compounds 1 and 2 on normal bone marrow growth. FIG. 16A is a line graph showing that the compound 2 treatment of primary AML cells (JAK2-V617F-positive) and normal donor-derived bone marrow cells (sample #2) for 24 hours. AML1 is de novo MPD/MDS and AML5 is secondary AML (Table 2, infra). FIG. 16B is a line graph showing the 24-hour treatment of normal bone marrow cells (sample #2) or HEL cells with compound 1 or 2. FIG. 16C is a line graph showing the 72-hour treatment of normal bone marrow cells (sample #2) or HEL cells with ruxolitinib. Normal bone marrow cells were treated with drug in the presence of cytokines. Primary AML patient cells and HEL cells were treated with drug in the absence of cytokines.

FIG. 17A is a bar plot showing that compound 1 inhibits cell growth of Ba/F3 cells and EPOR-JAK2-V617F-expressing Ba/F3 cells. FIG. 17B is a bar plot showing that compound 2 inhibits cell growth of Ba/F3 cells and EPOR-JAK2-V617F-expressing Ba/F3 cells. FIG. 17C is a series of blots showing that Ba/F3 cells and EPOR-JAK2-V617F-expressing Ba/F3 cells were treated with compound 1 or 2. JAK2 and β-Actin expression were detected by western blotting with the indicated antibodies.

FIG. 18A is a line plot showing the effects of compounds 1 and 2 on cell growth of Ba/F3 EpoR+ cells. FIG. 18B is a line plot showing the effects of compounds 1 and 2 on cell growth of EPOR-JAK2-V617F-expressing Ba/F3 cells.

FIG. 19A is a line plot showing the effects of fresh stocks of compounds 1 and 2 on growth of HEL cells. FIG. 19B is a line plot showing the effects of aged stocks of compounds 1 and 2 on growth of HEL cells.

DETAILED DESCRIPTION

Figure 1A:
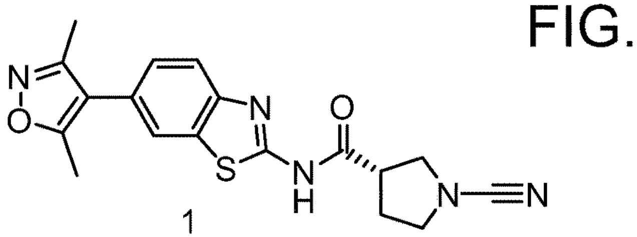
FIG. 1A-FIG. 1F is a chemical structure schematic, a series of line graphs, and a series of blots showing that compounds 1 and 2 selectively degrade JAK2-V617F and kill JAK2-V617F-expressing Ba/F3 cells.
Figure 1A:
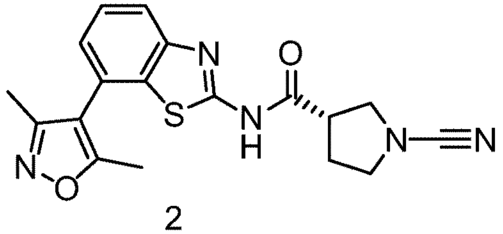

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated to facilitate the understanding of the present disclosure.

Definitions

The transitional term “comprising,” which is synonymous with “including,” “containing,” or “characterized by,” is inclusive or open-ended and does not exclude additional, unrecited elements or method steps. By contrast, the transitional phrase “consisting of” excludes any element, step, or ingredient not specified in the claim. The transitional phrase “consisting essentially of” limits the scope of a claim to the specified materials or steps “and those that do not materially affect the basic and novel characteristic(s)” of the claimed invention.

Unless specifically stated or obvious from context, as used herein, the term “or” is understood to be inclusive. Unless specifically stated or obvious from context, as used herein, the terms “a”, “an”, and “the” are understood to be singular or plural.

By “neoplasia” is meant a disease or disorder characterized by excess proliferation or reduced apoptosis. Illustrative neoplasms for which the disclosure can be used include, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic myelomonocytic leukemia, chronic lymphocytic leukemia), myelodysplastic syndrome, Essential Thrombocythemia, Primary Myelofibrosis, polycythemia vera, lymphoma (Hodgkin’s disease, non-Hodgkin’s disease), and Waldenstrom’s macroglobulinemia.

The terms “treating” and “treatment” as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition or symptoms associated therewith be completely eliminated.

Any compositions or methods provided herein can be combined with one or more of any of the other compositions and methods provided herein.

Myeloproliferative Neoplasms

Myeloproliferative neoplasms (MPN) are cancers that start in the bone marrow and are diagnosed using blood tests and a bone marrow biopsy. The valine-to-phenylalanine substitution at amino acid position 617 (V617F) has been identified as an important mutation in Janus kinase 2 (JAK2) in patients with MPNs.

MPNs are commonly asymptomatic; however, when symptoms do occur, they include headaches, blurred vision, fatigue, weakness, dizziness, itchiness (pruritus), night sweats, and raised blood pressure (hypertension).

There are several types of MPNs, including Polycythemia vera (PV), in which the bone marrow overproduces red blood cells; Essential thrombocythemia (ET), in which the bone marrow overproduces platelets, Myelofibrosis (MF) (Primary Myelofibrosis also called Idiopathic Myelofibrosis; IM), which causes scarring in the bone marrow and the reduction of less red blood cells, leading to anemia, and Chronic Myeloid Leukemia (CML) (also known as Chronic Myelogenous Leukemia), in which the bone marrow overproduces white blood cells.

PV is a chronic disorder involving the overproduction of blood cells in the bone marrow (myeloproliferation). Red blood cell overproduction is most dramatic, but white blood cells and platelets may also be elevated. PV causes hyperviscosity (increased blood thickness and volume), which may not flow through smaller blood vessels properly causing headaches, fatigue, weakness, dizziness or itchy skin, splenomegaly, gastrointestinal issues, and the risk of blood clots. The JAK2-V617F mutation is found in the majority of PV cases.

ET is characterized by the persistent overproduction of platelets in the absence of a recognizable cause of thrombocytosis such as chronic inflammation, a concurrent nonhematologic malignancy, or another MPD. The JAK2-V617F mutation is found in approximately half of ET cases. IM is a progressive, chronic disease in which the bone marrow is replaced by fibrous scar tissue, reducing bone marrow-derived blood cell generation. Organs such as the liver and spleen begin to generate blood cells to replace the lost bone marrow generation. This disease is marked by an enlarged spleen and progressive anemia. IM is also called agnogenic myeloid metaplasia, myelosclerosis with myeloid metaplasia, and primary myelofibrosis. Androgens, recombinant human erythropoietin (rHuEpo), and thalidomide are effective modalities of treatment of the anemia of IM.

CML is a slowly progressing blood and bone marrow disease that usually occurs during or after middle age, and rarely occurs in children. CML is characterized by overproduction of granulocytes in the bone marrow. The produced granulocytes do not become healthy, normally functioning cells and build up in the blood and bone marrow so there is less room for healthy white blood cells, red blood cells, and platelets, elevating the risk for infection, anemia, or easy bleeding.

PV and ET may develop into FM. However, generally, MPNs can evolve over time into other serious myeloid diseases, including acute myeloid leukemia (AML), myelodysplastic syndromes (MDS), JAK2-V617F-positive MDS, chronic myelomonocytic leukemia (CMML), or advanced myelofibrosis.

AML is a bone marrow cancer, but most often quickly moves into the blood. AML may further spread to other organs including the lymph nodes, liver, spleen, central nervous system (brain and spinal cord), and testicles. AML most often affects white blood cells but may also involve red blood cells and platelets. AML is the most common type of acute leukemia in adults and typically gets worse quickly if it is not treated. AML is also called acute myelogenous leukemia and acute nonlymphocytic leukemia.

MDS are a group of cancers in which immature blood cells in the bone marrow do not mature or become healthy blood cells. The different types of MDS are diagnosed based on certain changes in the blood cells and bone marrow. Age and past treatment with chemotherapy or radiation therapy affect the risk of developing an MDS. Signs and symptoms of MDS include shortness of breath and feeling tired.

CMML is a clonal disorder of hematopoietic cells and is a complex of heterogeneous conditions with both myeloproliferative and myelodysplastic features. CMML is characterized by an increase in monocytes and dysplasia of myeloid precursor cells. CMML is common in old age, show a male predominance, and is a relatively rare disease. The diagnosis of CMML is made using morphologic criteria including monocyte-dominant leukocytosis, dysplastic changes, and increased blasts in the bone marrow. CMML is often diagnosed by excluding other diseases accompanied by monocytosis and other types of MDS/MPN diseases.

The JAK2 Valine-to-Phenylalanine (V617F) Mutation

JAK2-V617F is the most frequently occurring mutation leading to the development of MPN and subsets of AML (James, et al., 2005, Nature, 434(7037):1144-48; Baxter, et al., 2005, Lancet, 365(9464):1054-61; Kralovics, et al., 2005, N Engl J Med., 352(17):1779-90; Levine, et al., 2005, Cancer Cell, 2005; 7(4):387-97; Wernig, et al., 2006, Blood, 107(11):4274-81). In addition to allogeneic hematopoietic stem cell transplantation (HSCT), the classic treatment for MPN, another promising therapeutic approach has been targeted inhibition of the "druggable" therapeutic target, JAK2-V617F.

FDA approved JAK2 inhibitory drugs, such as ruxolitinib (JAKAFI®), have generally shown moderate, but significant clinical activity in MPN patients or in patients with MPN who progressed to AML (Harrison, et al., 2012, N Engl J Med., 366(9):787-98; Verstovsek, et al., 2012, N Engl J Med., 366(9):799-807; Eghtedar, et al., 2012 Blood, 119 (20):4614-8) validating it as a therapeutic target. However, while treatment with JAK2 inhibitors leads to reduced spleen size and disease symptoms, dose-limiting toxicities such as thrombocytopenia and anemia resulting from inhibition of wild-type (wt) JAK2 limits clinical utility (Ajayi, et al., 2018, Cancer Res., 212:119-32). Also, while these inhibitors ameliorate symptoms, the mutant clone persists, increasing the likelihood that patients will ultimately develop further mutations and progress to acute leukemia. As the JAK2-V617F mutation is in the pseudokinase domain located away from the functional JH1 kinase domain ATP-binding pocket, and JAK2 inhibitors in clinical development are ATP-competitive inhibitors of the JH1 kinase domain, these inhibitors also lack structural specificity for mutated JAK2 compared to wt JAK2 (Kong, et al., 2017, Sci Rep., 7(1):9088). In addition to the limitations resulting from inhibition of wt JAK2, drug resistance is also a problem in patients receiving kinase inhibitors, typically occurring after 1-2 years of treatment (Meyer, et al., 2014, Clin Cancer Res., 20(8):2051-59; Koppikar, et al., 2012, Nature, 489(7414): 155-59; Andraos, et al., 2012, Cancer Discovery, 2(6):512).

Resistance may also result from compensatory activities by other JAK family members that form complexes with drug-inhibited JAK2. (Harrison, et al., 2012 N Engl J Med., 366(9):787-98; Verstovsek, et al., 2012, N Engl J Med., 366(9):799-807; Koppikar, et al., 2012, Nature, 489(7414): 155-9). Thus, there is an urgent need for more efficacious, targeted approaches that inhibit aberrant JAK2 activity without affecting JAK2 signaling in normal cells.

Additional diseases and disorders mediated by dysregulated JAK2 mutations include leukemias with chromosomal translocations generating translocation-Ets-leukemia (TEL, also known as ETV6)-JAK2 and pericentriolar material 1 (PCM1)-JAK2 gene fusions, and mutations in JAK exon 12, which occur in a minority of JAK2-V617F-negative PV and Idiopathic Erythrocytosis patients (less than 2% of diagnoses) (Scott, et al., 2007, N Engl J Med., 356(5): 459-468).

Deubiquitinating Enzymes (DUBs)

Ubiquitin is a small protein consisting of 76 amino acids that is important for the regulation of protein function in the cell. Ubiquitylation and deubiquitylation are enzymatically mediated processes by which ubiquitin is covalently bound or cleaved from a target protein. These processes have been implicated in the regulation of many cellular functions including cell cycle progression, apoptosis, modification of cell surface receptors, regulation of DNA transcription, and DNA repair. Thus, the ubiquitin system has been implicated in the pathogenesis of numerous disease states including inflammation, viral infection, metabolic dysfunction, central nervous system (CNS) disorders, and oncogenesis (Clague, et al., 2013, Physiol Rev, 93:1289-1315). A number of ubiquitin-like (Ubls) molecules have been identified that regulate protein functions in cells in a similar manner to ubiquitin.

Ubiquitin and Ubls molecules are cleaved from proteins by enzymes called isopeptidases or deubiquitinating enzymes (DUBs), of which there are approximately 95 DUBs in human cells, divided into sub-families based on sequence homology: ubiquitin C-terminal hydrolases (UCHs), ubiquitin-specific proteases (USPs), ovarian tumor proteases (OTUs), Machado-Josephin domain proteases (MJDs), JAB 1/MPN MOV34 metalloproteases (JAMMs) or Sentrin-specific proteases (SENPs). DUBs can process ubiquitin or ubiquitin-like adducts. A number of DUBs have been linked to various diseases including cancer, inflammation, neurodegenerative diseases and anti-infectives (Kim, et al., 2013, Curr Pharm Des., 9(22):4039-52; Nicholson, et al., 2014, J Biomol Screen, 19(7):989-99; Ristic, et al., 2014, Front Mol Neurosci., 19(7):72; Ashida, et al., 2014, Nat Rev Microbiol., 2(6): 399-413.)

JOSD1

Herein, JOSD1 was identified and validated as a DUB that stabilizes JAK2-V617F, using genetic and biochemical approaches.

An exemplary JOSD1 amino acid molecule is provided at NCBI Accession No. NP_001347164, version NP_001347164.1, incorporated herein by reference, and reproduced below (SEQ ID NO: 1):

```
  1 mscvpwkgdk akseslelpq aappqiyhek qrrelcalha lnnvfqdsna ftrdtlqeif
 61 qrlspntmvt phkksmlgng nydvnvimaa lqtkgyeavw wdkrrdvgvi altnvmgfim
121 nlpsslcwgp lklplkrqhw icvrevggay ynldsklkmp ewiggeselr kflkhhlrgk
181 ncelllvvpe eveahqswrt dv
```

An exemplary JOSD1 nucleic acid sequence is provided at NCBI Accession No. NM_001360235, version NM_001360235.2, incorporated herein by reference and set forth below (SEQ ID NO: 2):

```
   1 agtcaacgca gaaggagcga gaacgttcgg ccgaaaagcc cggcacagag aagggagggg
  61 tgctgaaagc cgcggactgc agccgctggc ctggctgccg ccccgaaaca acgcccacgc
 121 ccgggagaag ggcaggctgg cgtccagggc cgcggccaga gggctagaat ccgcgccttc
 181 cgagggagcc gcgccctgcg ggccccaccg tacccgaggg gatggagggc tgcccccgag
 241 gcccccgcgc ggctcgcggt cccacgcctg ccggcccgcg ctagctactc gactcgtgcg
 301 ctaaatttat ccgtcaccca ggccttgtct cccgagtcat tggcgtcgtg gttcaaaaga
 361 aatggaagaa aaggagcgat gtgaccgatt gtgttcggtc ctcctgcttt gaggcctggc
 421 atttgcagag ggaaacagca agaaaatcgt ggggatttttg gaggggggtg ggagggaagg
 481 gtggggaaac ggaaacaagg tcttacattt tatgtgtttt tttaaattct gcactttgac
 541 agtggtagca aaataaaagt aatccaaaag ttatttttct attgagaaga gagaagaggt
 601 gggttttatt tttttccttt tgattccaat cttttctccc agtgacaaag cataaatcat
 661 ggacaccaga gaataaggtg gacctcagga atccggaaaa gactgagaag cttacattct
 721 tcctctagag ggaagagtgg ggtgtttata gccatctctg gaacctaaaa caaaaaacat
 781 gagttgtgtg ccatggaaag gagacaaggc caaatctgaa tcattggagc tgccccaggc
 841 agcaccccca caaatctacc atgagaaaca gcgcagggag ctttgtgccc tccacgccct
 901 caataacgtc ttccaggaca gcaatgcctt cacccgggat acgctgcaag agattttcca
 961 gaggttgtct ccaaacacca tggtgacacc tcacaagaag agcatgctgg gaaatggcaa
1021 ctacgatgtg aatgtcatta tggcagcact tcagaccaaa ggctatgaag ctgtttggtg
1081 ggacaagcgc agggatgtcg gtgtcattgc cctcactaac gtcatgggct tcatcatgaa
1141 tctgccctcc agcctatgct ggggtccact gaaactgccc ctcaaaaggc agcactggat
1201 ctgtgttcga gaggtgggag gggcctacta caacctcgac tccaaactca agatgcccga
1261 gtggattgga ggcgagagcg agctcaggaa gtttctaaaa catcatttgc gaggaaagaa
1321 ctgtgaactc ctgctggtgg taccagaaga ggtagaggct catcagagtt ggaggaccga
1381 tgtgtaacag ttctgcccaa cctccctctc gcctcagccc cttcagtcct ctgtgacgtg
1441 ctgtggcctc tacagtgggt ctgcccttgc cacttcccca aacatctcat caagtttttc
1501 cccttcagat ctgacagtgc aataggacag acgtgtggac tgttataaga actactcagt
1561 gttttgttcc tgggcaagga aggtaggagt tctgtgcact taaggccagt ggtcacaaac
1621 ccttgtttta tttaagagac agaggagaaa gtggagcggg gagggaatcc tagcttattt
1681 tccctttttct atgaggactt gacacaggtt ctgctgagtt gtcactgctg ctccagactc
1741 acctagagat gctgcctcca ctttccatcc tgtctgggtc tgaaaacagt gggtctgcag
1801 atagtgccca caaaccccat gtgactggtt tgaaggaccc agagcataaa ggtctctcag
```

-continued

```
1861  gaaaccatgt ccaaaaccct agcagcggta cagcatgctg tctccaaccc ttatccccag
1921  gtttaagggt ggtttatggc catacgtgga ggttttttgt tgttgttttt gagactgagt
1981  ttcactcttg ttgcccaggc tggagtgcaa tggcaccatc tcggctcact gcaacctcca
2041  cctcctggtt caagcgattc tcaggcctca gcttcccaag tagttgggat tacaggcgcc
2101  tgccaccaca cctggctaat tttgtatttt tagtagagat ggggtttctc catgttggtc
2161  aggctggtct caaactcccg acctcaagtg atctgcccgc cttggcctcc caaagtgctg
2221  ggattacagg cgtgagccac cgcacccggc agagttttat aatgaaaaat taactaatat
2281  tctagtatga agtgaggagg atactgaaca ggatgtggct aaagccaacc tgggacagcc
2341  atggggtggc ttggtttctt cactccagtg tigtccctac catttcgcag cattgattta
2401  ggaggctctg ggacaaaaga gaagccaaag agcagttttc ccagttcact cactctggca
2461  aaatcaggaa aaaaaagtct gcttttgaca tcaaattcca ctaatttggg gcagcgttgg
2521  gtgaggaaag tattgtgaag acaggcttct tcgagtaggg gcagccacaa ttcagtagac
2581  actctaggct cggaggctgc cactgtagtt gccaagctca ggttgggtgg ttctgtgctg
2641  tatggatgga ataggacctg ggctggtcat cttcatgtcg tttcctctct gtatcaatgg
2701  aagttcaacc cgcccctacc tcttcagata gttgtaggcc actttctct tgtaactttg
2761  gaaaacaaaa gaggagaaat aagtatcata ccatatgcgt gtctccaaag tggatgtggt
2821  tgcctcaagg caggtggcag gcaggggtga cctgctggcc ctcagatcaa tggtcgtggc
2881  aggtctgaga gctgtcccac tggccagact tctctccagc agcaaagcca gcctggggct
2941  tgcatgttga tcctgagcaa gcttaacggg gtgaagctgg gctttctccc ccctgtgact
3001  ggagtgcatg ttgacaccag cactttttct gcacatgtat cttcaatcca acaaggccgt
3061  tttttaatg ctgagtaaca ggccaccaag cggctactgc gttatatctt ctcagcaact
3121  ggccgcagtc tcttctgcac cattttctac accagacctg cttggcacca cagggagctc
3181  ttttcctgcc ctgcacaatg acattccaac caccaccagc cagacattac agccaacctt
3241  gctgattgtc acaagcagga ccttggggcc actggcactg tcagatagta agccatttct
3301  tgggtagagg aggaaactcc tctccacaaa tccacttggg cctgtgcaaa tggcacttga
3361  aagagtcccc atgcacttgg agtccatgag ccaatgggat atgcaaagac gcttaaacat
3421  ttcagggctg gtttctctgt tcatatccaa ttctggtgct taggaacagg gacccatgct
3481  gatgcccaag ggcaaaaagc cccacttcct ttaaggaagt gaacaggcct gaccctgatg
3541  cccaataacg ggcaacccta ggctttttgt ttttcttgct tttattcctt tttgttgttg
3601  gccttgtgct gcgtttgttt acaaaagatg tattttgttt aaccaaatat taaaaatgga
3661  aaactccata tatgtctcct tgtctgcctg aattctataa ttgtgtaaag aaaaataaac
3721  tttagtatga cgctgtttta aaagga
```

JOSD1 is generally an understudied DUB, and the first-in-class inhibitors that are presented herein, or optimized derivatives thereof, could be useful tools for probing JOSD1-mediated signaling and identifying coactivators and regulatory partners. In addition, presented herein is a therapeutic approach to JAK2-V617F-positive cancer that, unlike available JAK2-targeting small molecule kinase inhibitors, is selective for mutant JAK2 while sparing wt JAK2-expressing cells. In a more general sense, DUB inhibition to achieve selective inhibition of mutant/activated kinases may be able to be applied across many targets for which simultaneous therapeutic inhibition or ablation of the nonmutated counterpart can be deleterious to the patient.

Previously, USP10 inhibitors were identified as selectively targeting FLT3-ITD and kinase inhibitor-resistant FLT3 mutants over wt FLT3 in AML (Lamberto, et al., 2017, Cell Chem Biol., 224(12):1490-500 e11), and, herein, it is shown that JOSD1 inhibition selectively degraded mutant JAK2 over wt JAK2 in JAK2-V617F-positive hematopoietic malignancies. The findings are also reminiscent of studies identifying E3 ubiquitin-protein ligase Cbl (Cbl) as a dominant "activated protein tyrosine kinase-selective" ubiquitin ligase, with reports of Cbl protein-dependent ubiquitination targeting activated protein tyrosine kinases for degradation (Mohapatra, et al., 2013, Biochim Biophys Acta., 1833(1):122-39). These studies, combined with observations described herein, make targeted therapy that spares normal kinases in favor of their constitutively activated oncogenic counterparts an intriguing possibility.

Therapeutic targeting of mutant JAK2 by promoting its degradation via DUB inhibition as opposed to inhibition of its kinase activity is an innovative approach that may be beneficial for overcoming resistance to current JAK2 kinase inhibitors. In addition, selective degradation of the oncogenic target may prove more efficacious than kinase inhibitors by simultaneously blocking both enzymatic and scaffolding functions of oncogenic JAK2.

Taken together, these findings suggest that therapeutic targeting of JAK2-V617F by selectively promoting its degradation is potentially beneficial for both circumventing the adverse side effects associated with JAK2 inhibition in clinical testing and also for overriding the technical limitations associated with JAK2 kinase inhibition that reduce clinical efficacy.

DUB inhibitors of the present disclosure

Another aspect of the present disclosure is directed to compounds and pharmaceutically acceptable salts and stereoisomers thereof for DUB inhibition, particularly for JOSD1 inhibition.

In some embodiments, the compound is any one of the following structures:

(3)

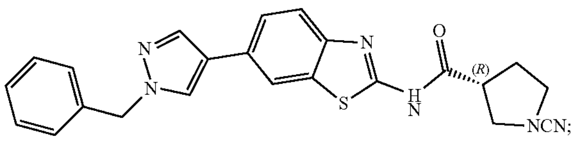

(4)

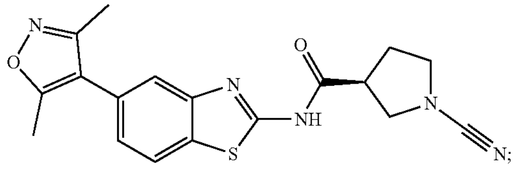

(5)

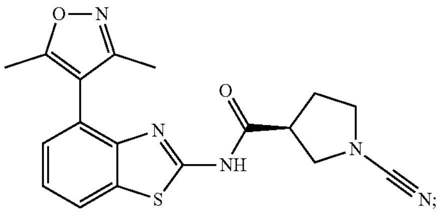

(6)

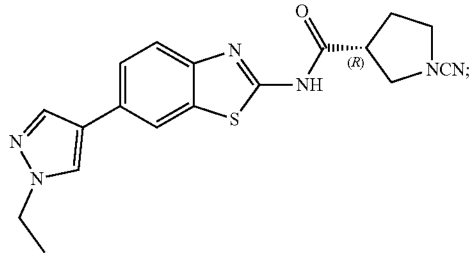

-continued (7)

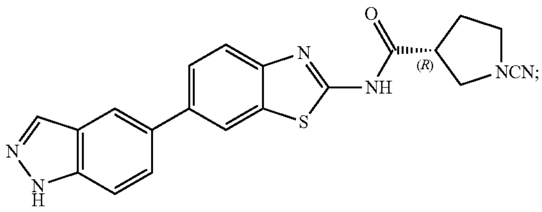

(8)

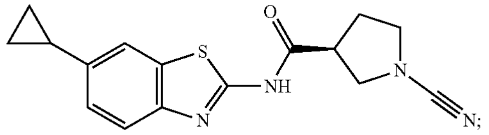

(9)

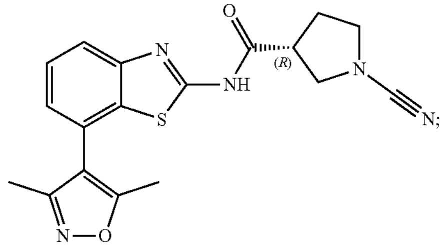

(10)

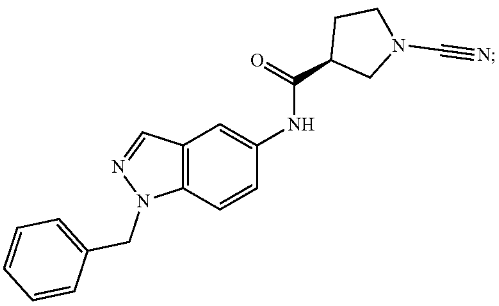

(11)

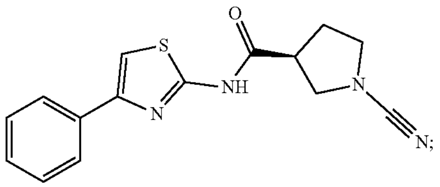

(12)

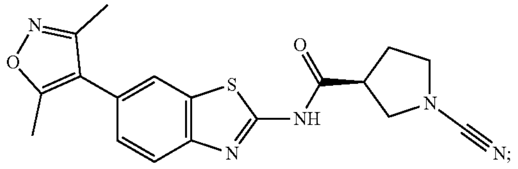

(13)

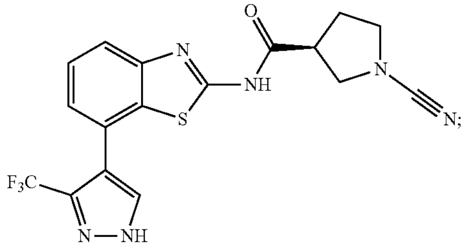

-continued
(14)
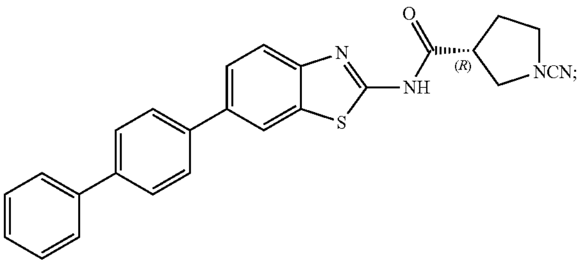
(15)
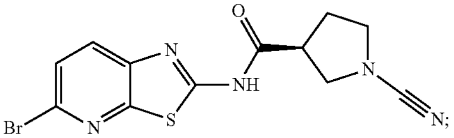
(16)
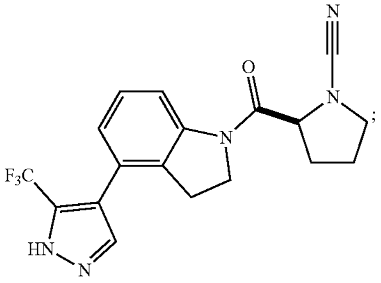
(17)
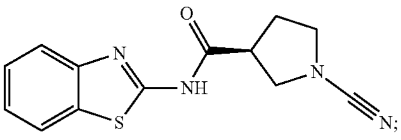
(18)
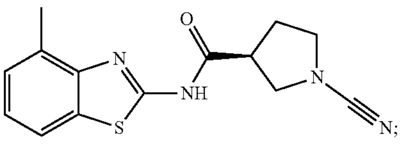
(19)
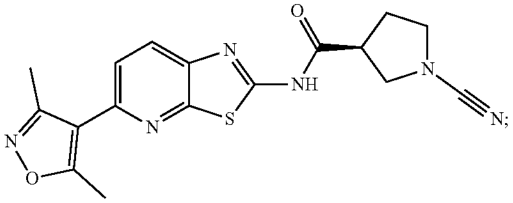
(20)
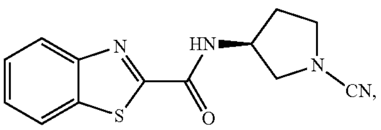
(21)
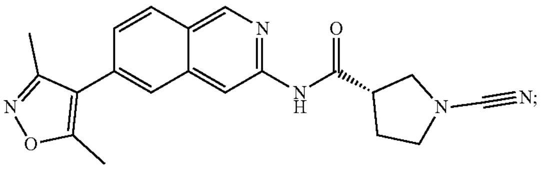
-continued
(22)
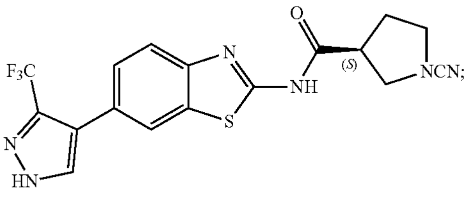
(23)
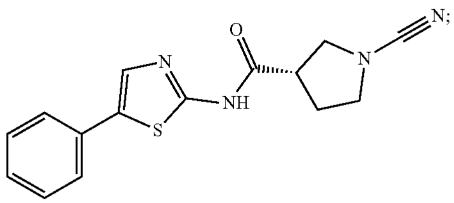
(24)
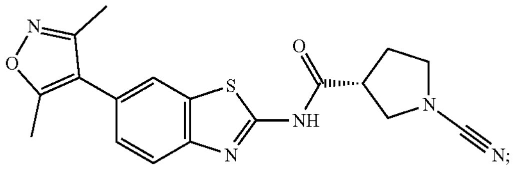
(25)
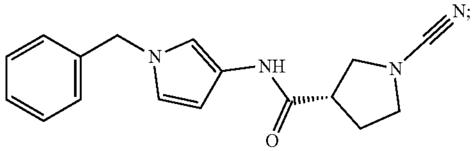
(26)
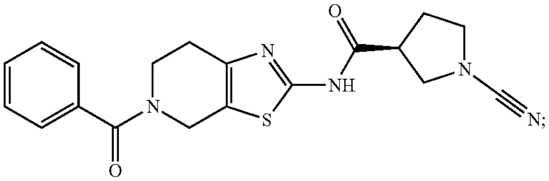
(27)
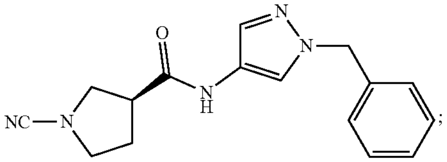
(28)
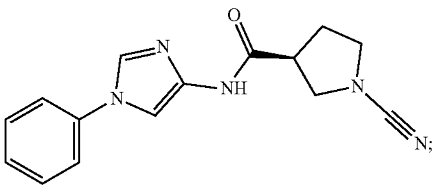
(29)
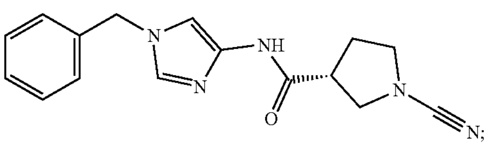

-continued
(30)
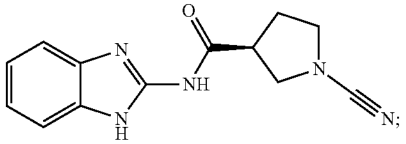
(31)
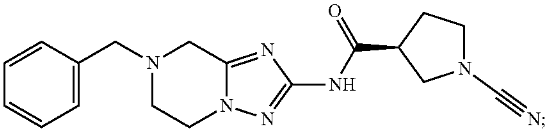
(32)
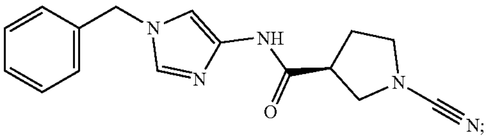
(33)
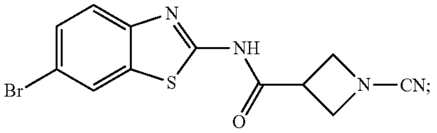
(34)
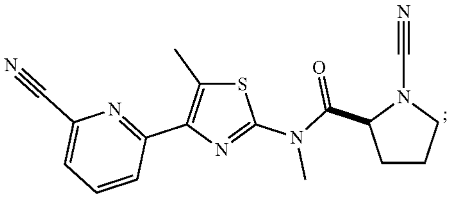
(35)
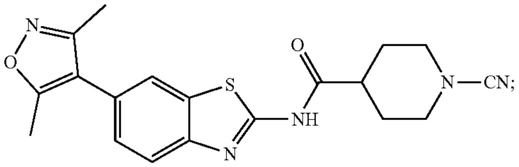
(36)
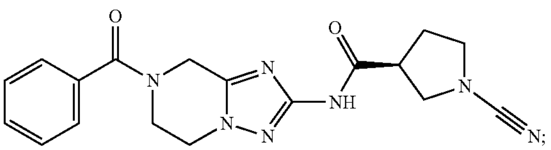
(37)
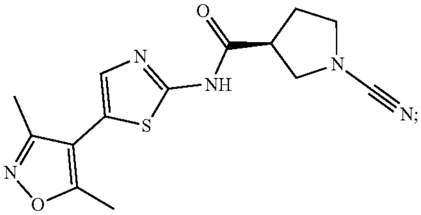
-continued
(38)
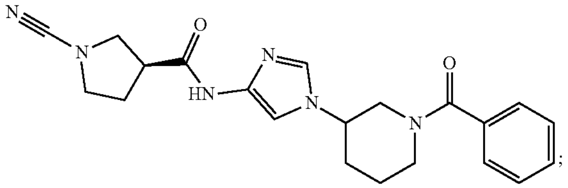
(39)
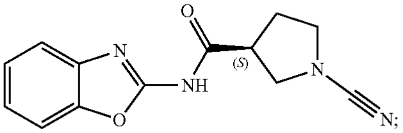
(40)
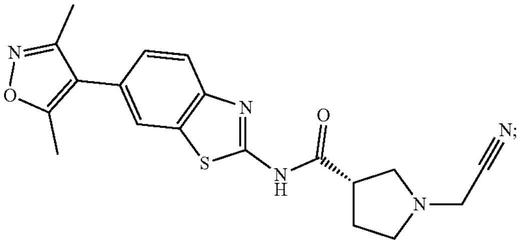
(41)
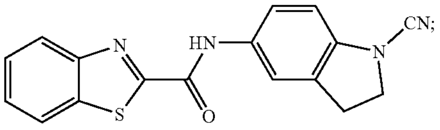
(42)
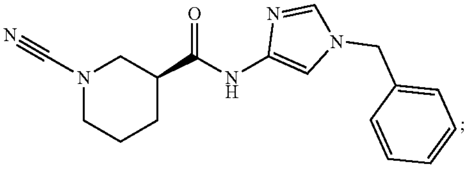
(43)
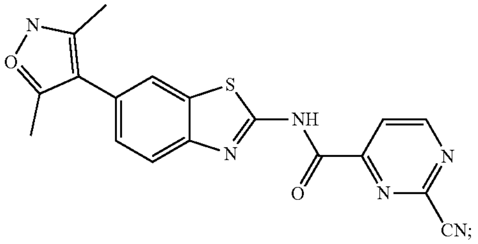
(44)
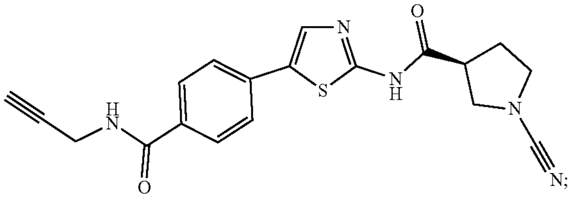

-continued
(45)
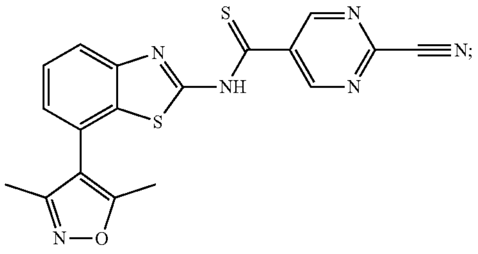
(46)
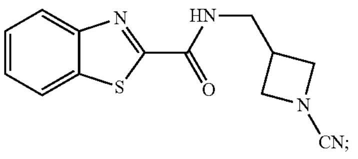
(47)
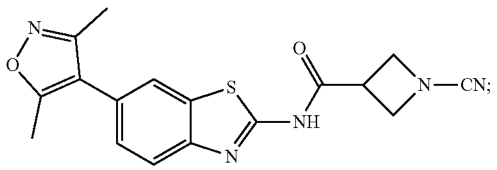
(48)
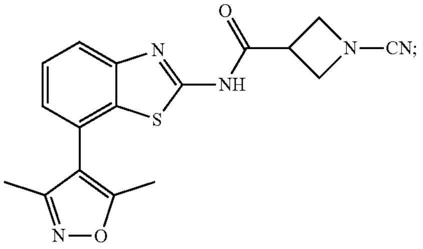
(49)
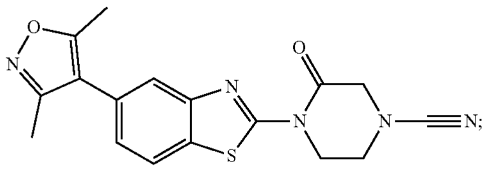
(50)
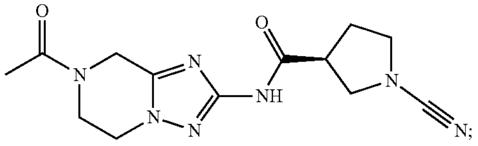
(51)
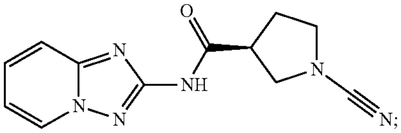
-continued
(52)
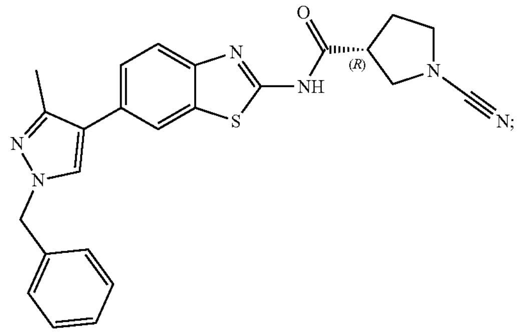
(53)
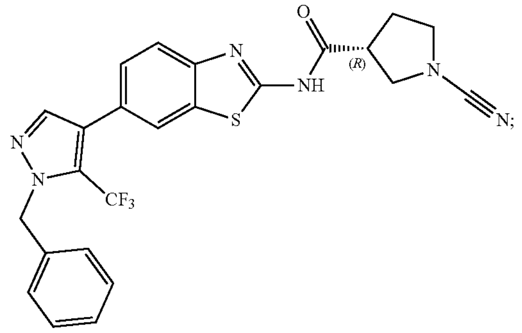
(54)
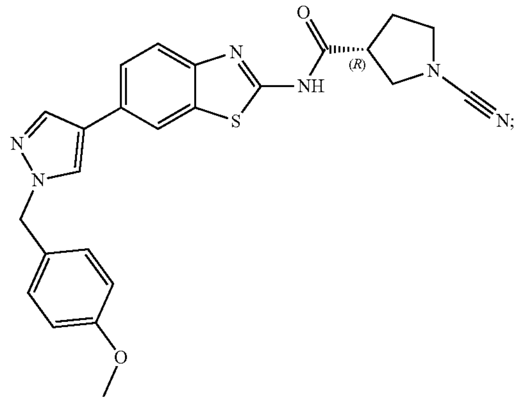
(55)
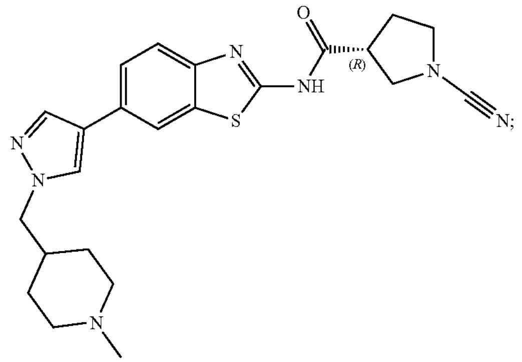

-continued
(56)
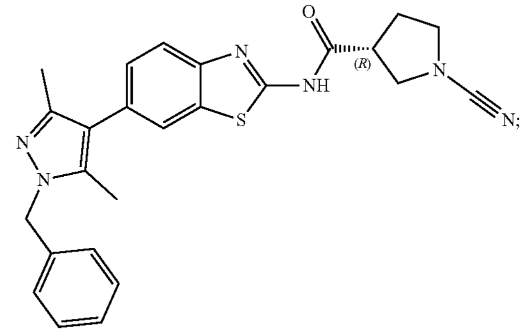
(57)
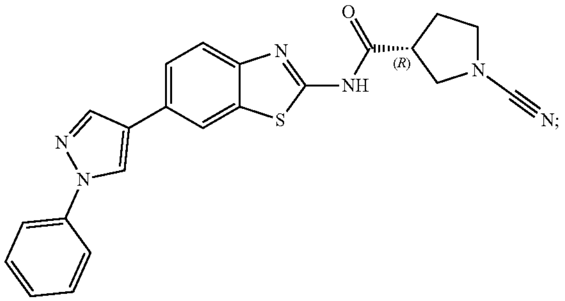
(58)
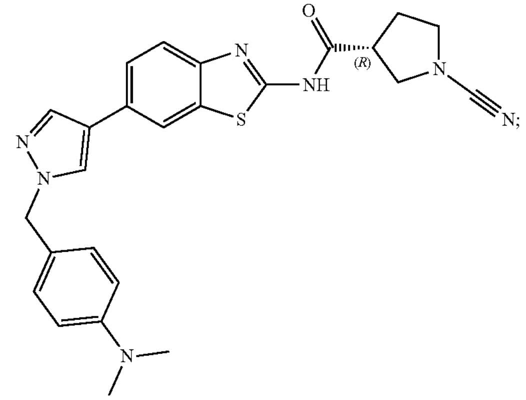
(59)
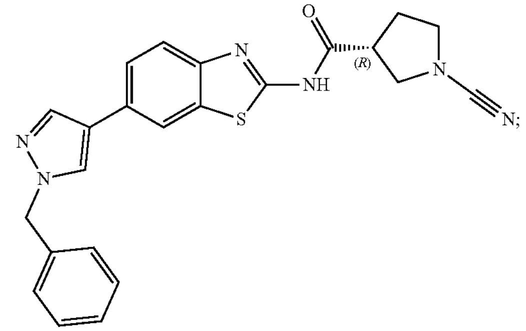
-continued
(60)
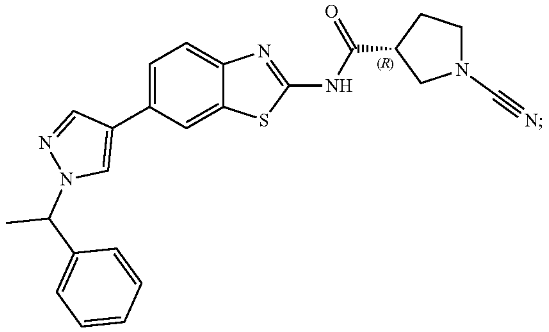
(61)
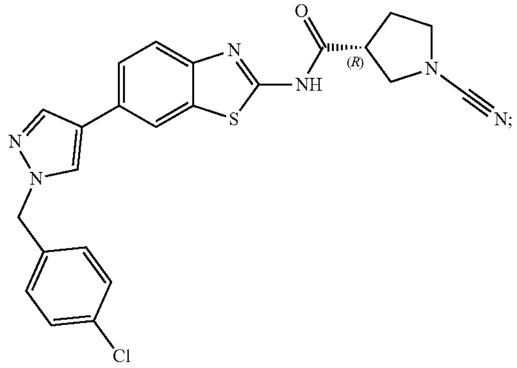
(62)
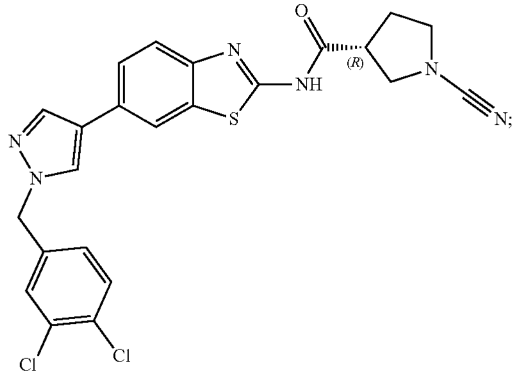
(63)
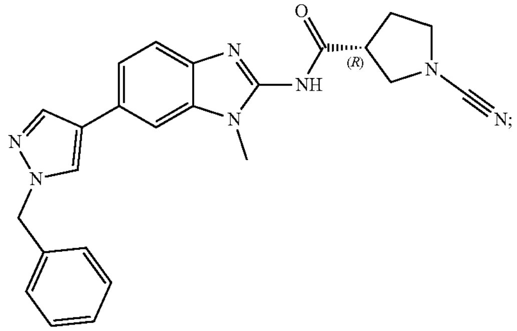

-continued (64)

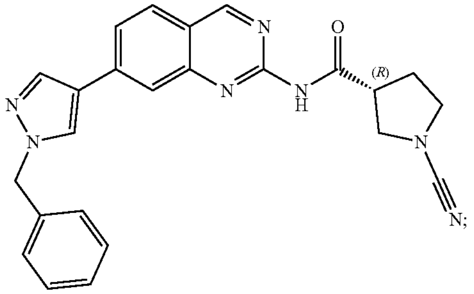

and (65)

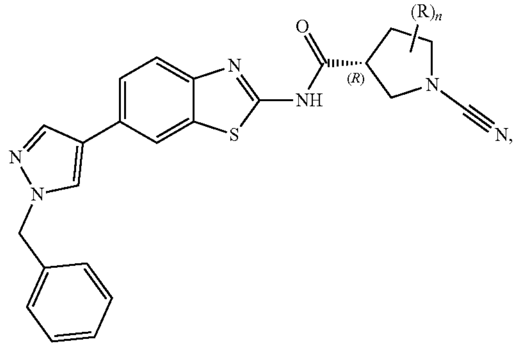

wherein R is methyl or halogen and n is an integer of 1-7, or a pharmaceutically acceptable salt or stereoisomer thereof.

In some embodiments, the compounds of the present disclosure are stable for several years. In some embodiments, the compounds are stable for a year. In some embodiments, the compounds are stable for more than one year. In some embodiments, the compounds are stable for at least two years. In some embodiments, the compounds are stable for two years to three years.

Compounds of the present disclosure may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present disclosure with a suitable acid or a base. Examples of pharmaceutically acceptable salts of the compounds of this disclosure include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the disclosure can form pharmaceutically acceptable salts with various organic bases such as lysine, arginine, guanidine, diethanolamine or metformin.

Compounds of the present disclosure may have at least one chiral center. Therefore, they may be in the form of a stereoisomer. As used herein, the term "stereoisomer" embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the compounds of the present disclosure may be made and used in the form of individual isomers and substantially free of other isomers, or in the form of a mixture of various isomers, e.g., racemic mixtures of stereoisomers.

In some embodiments, the compound of the present disclosure is an isotopic derivative in that it has at least one desired isotopic substitution of an atom, at an amount above the natural abundance of the isotope, i.e., enriched. In one embodiment, the compound includes deuterium or multiple deuterium atoms. As used herein, the term "compound" embraces isotopic derivatives.

In addition, compounds of the present disclosure may also be in the form of N-oxides, crystalline forms (also known as polymorphs), active metabolites of the compounds having the same type of activity, tautomers, and unsolvated as well as solvated and hydrated forms with pharmaceutically acceptable solvents such as water, ethanol, and the like, of the compounds. As used herein, the term "compound" embraces all these forms.

Methods of Synthesis

In some embodiments, the present disclosure is directed to a method for making compounds the present disclosure or a pharmaceutically acceptable salts or stereoisomers thereof. Broadly, the compounds of the disclosure or pharmaceutically-acceptable salts or stereoisomers thereof, may be prepared by any process known to be applicable to the preparation of chemically related compounds. The compounds of the present disclosure will be better understood in connection with the synthetic schemes that described in various working examples that illustrate non-limiting methods by which the compounds of the disclosure may be prepared.

Pharmaceutical Compositions

Another aspect of the present disclosure is directed to a pharmaceutical composition that includes a therapeutically effective amount of a compound of the present disclosure or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present disclosure to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may further include one or more pharmaceutically acceptable excipients.

Broadly, compounds of the present disclosure and their pharmaceutically acceptable salts and stereoisomers may be formulated into a given type of composition in accordance with conventional pharmaceutical practice such as conventional mixing, dissolving, granulating, dragee-making, levigating, emulsifying, encapsulating, entrapping and compression processes (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the compounds are formulated for oral or intravenous administration (e.g., systemic intravenous injection).

Accordingly, compounds of the present disclosure may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, compounds of the present disclosure may be formulated in a hard or soft gelatin capsule. Representative excipients that may be used include gelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include excipients such as wetting agents, suspending agents, coloring, sweetening, flavoring, and perfuming agents.

Injectable preparations may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, compounds of the present disclosure may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The compounds may be formulated for buccal or sublingual administration, examples of which include tablets, lozenges and gels.

The compounds may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Compounds of the present disclosure may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerin, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a compound of the present disclosure or a pharmaceutically acceptable salt or a stereoisomer thereof; or a composition including a compound of the present disclosure or a pharmaceutically acceptable salt or a stereoisomer thereof, effective in producing the desired therapeutic response in a particular patient suffering from a disease or disorder characterized or mediated by aberrant protein activity. The term "therapeutically effective amount" thus includes the amount of a compound of the disclosure or a pharmaceutically acceptable salt or a stereoisomer thereof, that when administered, induces a positive modification in the disease or disorder to be treated, or is sufficient to prevent development or progression of the disease or disorder, or alleviate to some extent, one or more of the symptoms of the disease or disorder being treated in a subject, or which simply kills or inhibits the growth of diseased (e.g., cancer (e.g., myeloproliferative neoplasm (MPN)) cells, or reduces the amount of aberrant proteins in diseased cells.

The total daily dosage of the compounds and usage thereof may be decided in accordance with standard medical practice, e.g., by the attending physician using sound medical judgment. The specific therapeutically effective dose for any particular subject may depend upon a variety of factors including the disease or disorder being treated and the severity thereof (e.g., its present status); the age, body weight, general health, sex and diet of the subject; the time of administration, route of administration, and rate of excretion of the specific compound employed; the duration of the treatment; drugs used in combination or coincidental with the compound; and like factors well known in the medical arts (see, for example, Goodman and Gilman's The Pharmacological Basis of Therapeutics, 10th Edition, A. Gilman, J. Hardman and L. Limbird, eds., McGraw-Hill Press, 155-173, 2001).

Compounds of the present disclosure and their pharmaceutically acceptable salts and stereoisomers may be effective over a wide dosage range. In some embodiments, the total daily dosage (e.g., for adult humans) may range from about 0.001 to about 1600 mg, from 0.01 to about 1600 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, and in yet other embodiments from about 10 to about 30 mg per day. Individual dosages may be formulated to contain the desired dosage amount depending upon the number of times the compound is administered per day. By way of example, capsules may be formulated with from about 1 to about 200 mg of a compound (e.g., 1, 2, 2.5, 3, 4, 5, 10, 15, 20, 25, 50, 100, 150, and 200 mg). In some embodiments, individual dosages may be formulated to contain the desired dosage amount depending upon the number of times the compound is administered per day.

Methods of Use

In some aspects, the present disclosure is directed to methods of treating diseases or disorders involving aberrant (e.g., dysfunctional or dysregulated) activity of JAK2 that entails administration of a therapeutically effective amount of a compound of the present disclosure or a pharmaceutically acceptable salt or stereoisomer thereof, to a subject in need thereof.

The diseases or disorders are characterized or mediated by aberrant activity of JAK2 (e.g., elevated levels of mutant JAK2 or otherwise functionally abnormal levels of mutant JAK2 relative to a non-pathological state). In some embodiments, the mutant JAK2 comprises a valine-to-phenylalanine (V617F) mutation. A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the animal's state of health.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present disclosure may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject is suffering from the disease or disorder. Thus, subjects suffering from, and suspected of suffering from, a specific disease or disorder are not necessarily two distinct groups.

In some embodiments, the compounds may be useful in the treatment of cell proliferative diseases and disorders (e.g., cancer or benign neoplasms). As used herein, the term "cell proliferative disease or disorder" refers to the conditions characterized by deregulated or abnormal cell growth, or both, including noncancerous conditions such as neoplasms, precancerous conditions, benign tumors, and cancer.

Exemplary types of non-cancerous (e.g., cell proliferative) diseases or disorders that may be amenable to treatment with the compounds of the present disclosure include inflammatory diseases and conditions, autoimmune diseases, neurodegenerative diseases, heart diseases, viral diseases, chronic and acute kidney diseases or injuries, metabolic diseases, and allergic and genetic diseases.

In some embodiments, the compounds of the disclosure may be useful in the treatment of autoimmune diseases and disorders (autoimmunity). As used herein, the term "autoimmune disease" refers to conditions where the immune system produces antibodies that attack normal body tissues. Representative examples of such diseases include autoimmune hematological disorders (e.g., hemolytic anemia, aplastic anemia, anhidrotic ectodermal dysplasia, pure red cell anemia and idiopathic thrombocytopenia), Sjogren's syndrome, Hashimoto thyroiditis, rheumatoid arthritis, juvenile (type 1) diabetes, polymyositis, scleroderma, Addison's disease, lupus, including systemic lupus erythematosus, vitiligo, pernicious anemia, glomerulonephritis, pulmonary fibrosis, celiac disease, polymyalgia rheumatica, multiple sclerosis, ankylosing spondylitis, alopecia areata, vasculitis, autoimmune uveoretinitis, lichen planus, bullous pemphigus, pemphigus vulgaris, pemphigus *foliaceus*, paraneoplastic pemphigus, myasthenia gravis, immunoglobulin A nephropathy, Wegener granulomatosis, autoimmune oophoritis, sarcoidosis, rheumatic carditis, ankylosing spondylitis, Grave's disease, autoimmune thrombocytopenic purpura, psoriasis, psoriatic arthritis, dermatitis herpetiformis, ulcerative colitis, and temporal arteritis.

In other embodiments, the methods are directed to treating subjects having cancer. Broadly, the compounds of the present disclosure may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Adult tumors/cancers and pediatric tumors/cancers are included. The cancers may be vascularized, or not yet substantially vascularized, or non-vascularized tumors.

Representative examples of cancers include adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (nonmelanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), cholangiocarcinoma, germ cell tumor, ovarian germ cell tumor, head and neck cancer, neuroendocrine tumors, Hodgkin's lymphoma, Ann Arbor stage III and stage IV childhood Non-Hodgkin's lymphoma, ROS1-positive refractory Non-Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, renal cell carcinoma), liver cancer, lung cancer (e.g., non-small cell lung cancer and small cell lung cancer), ALK-positive anaplastic large cell lymphoma, ALK-positive advanced malignant solid neoplasm, Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, metastatic anaplastic thyroid cancer, undifferentiated thyroid cancer, papillary thyroid cancer, pituitary tumor, plasma cell neoplasm/multiple myeloma, pleuropulmonary blastoma, prostate cancer, retinoblastoma, rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, juvenile xanthogranuloma, transitional cell cancer of the renal pelvis and ureter and other urinary organs, urethral cancer, gestational trophoblastic tumor, vaginal cancer, vulvar cancer, hepatoblastoma, rhabdoid tumor, and Wilms tumor.

Sarcomas that may be treatable with the compounds of the present disclosure include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue), mesenchymous or mixed mesodermal tumor (mixed connective tissue types), and histiocytic sarcoma (immune cancer).

In some embodiments, methods of the present disclosure entail treatment of subjects having cell proliferative diseases or disorders of the hematological system, liver, brain, lung, colon, pancreas, prostate, ovary, breast, skin, and endometrium.

As used herein, "cell proliferative diseases or disorders of the hematological system" include lymphoma, leukemia, myeloid neoplasms, mast cell neoplasms, myelodysplasia, benign monoclonal gammopathy, lymphomatoid papulosis, polycythemia vera, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the liver may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), adenocarcinoma, small cell carcinoma, large cell carcinoma, squamous cell carcinoma, and mesothelioma. Lung cancer can include "scar carcinoma", bronchoalveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, a compound of the present disclosure may be used to treat non-metastatic or metastatic lung cancer (e.g., NSCLC, ALK-positive NSCLC, NSCLC harboring ROS1 rearrangement, lung adenocarcinoma, and squamous cell lung carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the endometrium. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

In some embodiments, the cancer is a myeloproliferative neoplasm (MPN). In some embodiments, the MPN is Polycythemia Vera (PV), Essential Thrombocythemia (ET), Idiopathic Myelofibrosis (IM), Chronic Myeloid Leukemia (CML), or Primary Myelofibrosis (ML). In some embodiments, the myeloproliferative neoplasm is myeloid neoplasm. In some embodiments, the myeloid neoplasm is myelodysplastic syndrome (MDS), chronic myelomonocytic leukemia (CMML), or acute myeloid leukemia (AML).

The compounds may be administered to a patient, e.g., a cancer patient, as a monotherapy or by way of combination therapy. Therapy may be "front/first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which were unsuccessful or partially successful but who became intolerant to the particular treatment. Therapy may also be given as an adjuvant treatment, i.e., to prevent reoccurrence of cancer in patients with no currently detectable disease or after surgical removal of a tumor. Thus, in some embodiments, the compounds of the present disclosure may be administered to a patient who has received another therapy, such as chemotherapy, radioimmunotherapy, surgical therapy, immunotherapy, radiation therapy, targeted therapy or any combination thereof, or to a patient in preparation for or in maintenance therapy after a hematopoietic stem cell transplant for MPN or AML. HSCT as a treatment for MPN or AML is known in the art. See, e.g., Rondelli et al., 2005, Blood, 105(10):4115-9; Kroger et al., 2009, Blood 114(26):5264-70; Alchalby et al., 2010, Blood 116(18):3572-81; and Raj et al., 2019, Biol. Blood Marrow Transplant, 25(3):522-528.

The methods of the present disclosure may entail administration of the compounds or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails a 28-day cycle which includes daily administration for 3 weeks (21 days) followed by a 7-day "off" period. In other embodiments, the compound may be dosed twice a day (BID) over the course of two and a half days (for a total of 5 doses) or once a day (QD) over the course of two days (for a total of 2 doses). In other embodiments, the compound of the present disclosure may be dosed once a day (QD) over the course of five days.

Combination Therapy

Therapies of the present disclosure and their pharmaceutically acceptable salts and stereoisomers may be used in combination or concurrently with at least one other active agent, e.g., anti-cancer agent or regimen, in treating diseases and disorders. The terms "in combination" and "concurrently" in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically) to provide an increased benefit than if they were administered otherwise. For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of an compound of the present disclosure with one or more additional therapeutics known for use in treating the disease or condition (e.g., cancer). The dosage of the additional anticancer therapeutic may be the same or even lower than known or recommended doses. See, Hardman et al., eds., *Goodman & Gilman's The Pharmacological Basis Of Basis Of Therapeutics,* 10th ed., McGraw-Hill, New York, 2001; Physician's Desk Reference 60th ed., 2006. For example, anti-cancer agents that may be suitable for use in combination with the compounds are known in the art. See, e.g., U.S. Pat. No. 9,101,622 (Section 5.2 thereof) and U.S. Pat. No. 9,345,705 B2 (Columns 12-18 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bifunctional antibodies) and CAR-T therapy.

In some embodiments, the treatment regimen may include administration of a compound of the present disclosure with a therapeutically effective amount of a chemotherapy or targeted therapy in preparation for or in maintenance therapy after a hematopoietic stem cell transplant for MPN or AML. The term "maintenance therapy" as used herein refers to a therapeutic regimen that is given to reduce the likelihood of disease or disorder recurrence or progression. Maintenance therapy can be provided for any length of time, including extended time periods up to the lifespan of the subject. Maintenance therapy can be provided after an initial therapy of a compound of the present disclosure or in conjunction with initial therapy of a compound of the present disclosure or in conjunction with additional combination therapies. Dosages used for maintenance therapy can vary and can include diminished dosages as compared to dosages used for other types of therapy (i.e., non-maintenance). In some embodiments, maintenance therapy is provided for at least 3 weeks, at least 4 weeks, at least 6 weeks, at least 9 weeks, at least 12 weeks, at least 24 weeks, at least 48 weeks, at least 64 weeks after completion of therapy with a compound of the present disclosure, optionally concurrently a combination therapy. In other embodiments, maintenance therapy is provided for at least 36 weeks, at least 48 weeks after completion of therapy with a compound of the present disclosure concurrently with 9 weeks or 18 weeks of a combination therapy.

In some embodiments, a compound of the present disclosure and the additional (e.g., anticancer) therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more (e.g., anticancer) therapeutics may be administered within the same patient visit.

In some embodiments involving cancer treatment, the compound of the present disclosure and the additional anti-cancer agent or therapeutic are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

In some embodiments, the compounds of the present disclosure may be co-administered with a therapeutically effective amount of an FDA approved chemotherapy (e.g., doxorubicin, daunorubicin, cytarabine, cladribine, fludarabine, mitoxantrone, etoposide, 6-thioguanine, methotrexate, azacytidine, all trans retinoic acid, arsenic trioxide, and decitabine), or targeted therapy comprising a poly adenosine diphosphate-ribose polymerase (PARP) inhibitor (e.g., Olaparib (Lynparza®), rucaparib (Rubraca®), niraparib (Zejula®), veliparib, and talazoparib (Talzenna®)), or a targeted therapy comprising inhibitors of provability signaling molecules (e.g., venetoclax (Venclexta®) and navitoclax), and/or a JAK2 inhibitor (e.g., ruxolitinib (Jakafi®), fedratinib (Inrebic®), momelotinib, and barcitinib (Olumiant®)) or any analog or derivative variant of the foregoing and also combinations thereof.

Additional chemotherapies involving mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and chimeric antigen receptor T cell (CAR-T) therapy are applicable to the combination therapies contemplated herein. In specific embodiments, chemotherapy for a subject is employed before, during and/or after administration of a compound of the present disclosure.

In some embodiments, the therapies of the present disclosure may be combined with a therapy directed to mitigate MPN symptoms; for example, blood withdrawals, plateletpheresis, and splenectomy. In some embodiments, the compounds of the present disclosure may be combined with a therapeutically effective amount of a drug therapy directed to mitigate MPN symptoms; for example, selective serotonin reuptake inhibitors (e.g., paroxetine (Brisdelle®, Paxil®, and Pexeva®) or fluoxetine (Prozac®, Sarafem®, and Selfemra®)) red blood cell reducers (e.g., Hydroxyruea (Droxia®, Hydrea®), Interferon alfa-2b (Intron A®), peginterferon alfa-2a (Pegasys®), Ruxolitinib (Jakafi®), or Busulfan (Busulfex®, Myleran®)), Anagrelide (Agrylin®), danazol (Danocrine®), prednisone anagrelide (Agrylin®), lenalidomide (Reylimid®), bisphosphonate zoledronic acid (Zometa®), Androgen therapy, Thalidomide (Thalomid®), lenalidomide (Reylimid®), decitabine (Dacogen®), and decitabine/cedazuridine combination (Ingovi®).

In some embodiments, the therapies of the present disclosure may be combined with a therapy directed to treat or mitigate CML including asciminib hydrochloride (Scemblix®), bosutinib (Bosulif®), busulfan (Busulfex®, Myleran®), cyclophosphamide, cytarabine, dasatinib (Sprycel®), dexamethasone, imatinib mesylate (Gleevec®), hydroxyurea (Hydrea®), ponatinib hydrochloride (Iclusig®), nilotinib (Tasigna®), and omacetaxine mepesuccinate (Synribo®).

In some embodiments, the therapies of the present disclosure may be combined with a therapy directed to treat or mitigate AML including arsenic trioxide (Trisenox®), azacitidine (Onureg®), cyclophosphamide, cytarabine, daunorubicin (Cerubidine®, Rubidomycin®), daunorubicin hydrochloride and cytarabine liposome (Vyxeos®), dexamethasone, doxorubicin hydrochloride, enasidenib mesylate (Idhifa®), gemtuzumab ozogamicin (Mylotarg®), gilteritinib fumarate (Xospata®), glasdegib maleate (Daurismo®), idarubicin (Idamycin PFS®), ivosidenib (Tibsovo®), midostaurin (Rydapt®), mitoxantrone, prednisone, thioguanine (Tabloid®), venetoclax (Venclexta®), and vincristine sulfate.

In some embodiments, the compounds of the present disclosure may be combined with a radiation-based, DNA-damaging treatments. Combination radiotherapies include what are commonly known as gamma-rays, X-rays, and/or the directed delivery of radioisotopes to tumor cells. Other forms of radiotherapies are also contemplated such as microwaves and UV-irradiation. It is most likely that all of these therapies cause a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

Pharmaceutical Kits

The present compounds and/or compositions containing them may be assembled into kits or pharmaceutical systems. Kits or pharmaceutical systems according to this aspect of the disclosure include a carrier or package such as a box, carton, tube or the like, having in close confinement therein one or more containers, such as vials, tubes, ampoules, or bottles, which contain a compound of the present disclosure or a pharmaceutical composition thereof. The kits or pharmaceutical systems of the disclosure may also include printed instructions for using the compounds and compositions.

These and other aspects of the present disclosure will be further appreciated upon consideration of the following Examples, which are intended to illustrate certain particular embodiments of the disclosure but are not intended to limit its scope, as defined by the claims.

EXAMPLES

Example 1: Materials and Methods

Chemical compounds and biologic reagents. DUB inhibitors, compounds 1 and 2, were designed and synthesized in-house (synthesis described in). Results of ultra performance liquid chromatography-mass spectrometry (UPLC-MS) analysis were consistent with reported purity and molecular weight. Ruxolitinib was provided by Dr. Jinhua Wang and Dr. Nathanael Gray (Dana-Farber Cancer Institute, Boston, MA). Inhibitors were dissolved in DMSO to obtain 10 mM stock solutions. Serial dilutions were then made, to obtain final dilutions for cellular assays with a final concentration of DMSO between 0.2 and 0.5%. Cycloheximide (CHX) and MG132 were purchased from Sigma-Aldrich®.

Cell lines and cell culture. Ba/F3 (interleukin [IL]-3-dependent murine pro-B) cells engineered to express EPOR and EPOR-JAK2-V617F were developed as previously described (Wernig, et al., 2008, Blood, 111(7):3751-9). K562 and KU812F (wt JAK2-expressing leukemia lines) were obtained from American Type Culture Collection (ATCC). The human JAK2-V617F-positive acute myeloid leukemia (AML) lines, HEL, SET2 and MUTZ-8, were purchased from the ATCC (Manassas, VA, USA). The HEL-FLAG/HA-JOSD1 cell line was constructed by infecting HEL with retroviral FLAG/HA-JOSD1 (Addgene®, #22547) followed by monoclonal cell selection and expansion.

All cell lines were cultured with 5% $CO_2$ at 37° C., at a concentration of 2×105 to 5×105 in RPMI (Thermo Fisher Scientific, Waltham, MA) with 10% fetal bovine serum (FBS) and 1% penicillin/streptomycin. Parental Ba/F3 cells were cultured in Roswell Park Memorial Institute (RPMI) medium with 10% FBS and 1% penicillin/streptomycin and supplemented with 20% WEHI (used as a source of IL-3). SET-2 cells were cultured in RPMI with 20%-25% FBS and 1% penicillin/streptomycin. MUTZ-8 cells were cultured in alpha-Minimum Essential Medium (MEM) with 20% FBS and 1% penicillin/streptomycin and supplemented with 20 ng/ml GM-CSF. Human cell lines were authenticated within 6 months of manuscript preparation through cell line short tandem repeat (STR) profiling (Molecular Diagnostics Laboratory, Dana-Farber Cancer Institute). All cell lines tested matched >80% with lines listed in the ATCC or DSMZ Cell Line Bank STR and were confirmed to be virus- and *mycoplasma*-free Cell Transfection. HEK-293T cells were cultured in DMEM containing 10% FBS, with 5% $CO_2$ at 37° C., and transfected using Polyethylenimine (PEI) (Polysciences) according to the manufacturer's instructions. The plasmids used were: JAK2-V617F (Addgene®, #64610), FLAG/HA-JOSD1 (Addgene, #22547), and FLAG/HA-pCDNA3.1 (Addgene®, #52535).

Immunoblotting and Immunoprecipitation. Protein lysate preparation, immunoblotting, and immunoprecipitation were carried out as previously described (Lamberto, et al., 2017 Cell Chem Biol., 224(12):1490-500 e11). Briefly, $0.7\times10^6$ cells were treated with compounds 1 and 2 at 0, 5, 10, and 20 μM for 16 or 24 hours, cells were collected, and lysate was prepared in radioimmunoprecipitation assay (RIPA) buffer, JAK family and downstream signaling protein levels were detected by western blotting with the indicated antibodies. For immunoprecipitation, 1 mg protein for each sample was prepared and 1 μg antibody was used, immunoglobulin G (IgG) was added in same amount as nontargeting control.

Proliferation and Drug Combination Studies. Proliferation and drug combination studies were carried out as previously described (Yang, et al., 2020, British Journal of Cancer, 122:1175-84).

Clustered regularly interspaced short palindromic repeats (CRISPR) Knock Out (KO) Assay. The CRISPR KO assay was performed using the CRISPR-CAS9 system. JOSD1 sgRNAs were designed and inserted into a pLentiCRISPR V2 vector (Addgene®, #52961) following the protocol of the Feng Zheng Laboratory. HEL cells were infected with Lentiviral single guide RNA (sgRNA)s and selected for puromycin resistance (1 μg/mL) after 72-hour (h) infection. Cells were collected after 3-5 days of selection, and protein as well as messenger RNA (mRNA) levels were determined by immunoblotting and quantitative reverse transcription (qRT)-polymerase chain reaction (PCR) (n=3). KO of USP30 was also performed using the CRISPR-CAS9 system. GFP-CAS9-expressing HEL cells were generated through infection with lentiviral GFP-CAS9, and GFP-sorted single cells were expanded to obtain a monoclonal population. Cells were infected with Lentiviral gRNAs (targeting USP30) (Thermo Fisher Scientific) and selected for puromycin resistance (1 μg/mL) after 72 h infection. Cells were collected after 3-5 days of selection, and protein as well as mRNA levels were determined by immunoblotting. The sequences of the sgRNAs used are as follows:

TABLE 1

Sequences for used sgRNAs.

| | | |
|---|---|---|
| Josd1-EXON3_sgRNA1F | CACCGTGAAGCCCATGACGTTAGTG | SEQ ID NO: 3 |
| Josd1-EXON3_sgRNA1R | AAACCACTAACGTCATGGGCTTCAC | SEQ ID NO: 4 |
| Josd1-EXON3_sgRNA2F | CACCGCACTGGATCTGTGTTCGAG | SEQ ID NO: 5 |
| Josd1-EXON3_sgRNA2R | AAACCTCGAACACAGATCCAGTGC | SEQ ID NO: 6 |
| Josd1-EXON3_sgRNA3F | CACCGATTGCCCTCACTAACGTCAT | SEQ ID NO: 7 |
| Josd1-EXON3_sgRNA3R | AAACATGACGTTAGTGAGGGCAATC | SEQ ID NO: 8 |
| Josd1-EXON3_sgRNA4F | CACCGCTGGATCTGTGTTCGAGAGG | SEQ ID NO: 9 |
| Josd1-EXON3_sgRNA4R | AAACCCTCTCGAACACAGATCCAGC | SEQ ID NO: 10 |
| Josd1-EXON2_sgRNA5F | CACCGCGCTGCAAGAGATTTTCCAG | SEQ ID NO: 11 |
| Josd1-EXON2_sgRNA5R | AAACCTGGAAAATCTCTTGCAGCGC | SEQ ID NO: 12 |
| USP30-T1 | GGATAAATACTGGTGTGAGG | SEQ ID NO: 13 |

TABLE 1-continued

| Sequences for used sgRNAs. | | |
|---|---|---|
| USP30-T2 | GTTCACCTCCCAGTACTCCA | SEQ ID NO: 14 |
| USP30-T3 | TAGCAGGGAGTTCATGAAGC | SEQ ID NO: 15 |

Knock Down (KD) Assay. pLKO.1 puro lentiviral short hairpin RNA (shRNA) vector particles against JOSD1 were purchased from Sigma-Aldrich® (St. Louis, MO). Cells were incubated with the viral particles in the presence of 5 gig/mL Polybrene for 24 h, and then fresh medium was added. After 72 h, the cells were selected with 0.5-1 μg/mL puromycin for 72 h. Following selection, cells were used for the studies as described. The sequences of the shRNAs used are as follows:

TABLE 2

| Sequences for used shRNAs. | | |
|---|---|---|
| 61804 | CCGGCCTCGACTCCAAACTCAAGATCTCGAGA TCTGAGTTTGGAGTCGAGGTTTTTG | SEQ ID NO: 16 |
| 61806 | CCGGCTACGATGTGAATGTCATTATCTCGAGA TAAGACATTCACATCGTAGTTTTTG | SEQ ID NO: 17 |
| 369909 | CCGGTTGCGAGGAAAGAACTGTGAACTCGAG TTCACAGTTCTTTCCTCGCAATTTTTG | SEQ ID NO: 18 |
| 376514 | CCGGAGACGTGTGGACTGTTATAAGCTCGAGC TTATAACAGTCCACACGTCTTTTTG | SEQ ID NO: 19 |

JOSD1 KD studies in HEL, SET-2, and MUTZ-8 cells. Viral particles were produced by co-transfecting pLKO.1 containing scramble (SCR) shRNA as a control or JOSD1 shRNA (purchased from Sigma-Aldrich®) together with psPAX2 (Addgene®, #12260) and pMD2.G (Addgene®, #12259), and concentrated using LENTI-X™ concentrator (Clontech®). HEL, SET-2, and MUTZ-8 cells were then infected in the presence of 5 μg/mL polybrene and selection was started 48 h post-infection using 0.5-1 μg/mL puromycin. For monoclonal cell selection: Cells were diluted to a concentration of 30 cells per 20 mL complete medium with puromycin, followed by mixing well and transferring into a 96 well plate (flat). Cells were then cultured in a 5% CO2 incubator at 37° C. for 1-2 weeks.

In vitro JOSD1 activity assay & Ubiquitin-7-amido-4-methylcoumarin (AMC) assay. In vitro JOSD1 activity assay was carried out with Ubiquitin-AMC assay. The Ubiquitin-AMC assay was carried out as previously described (Wernig, et al., 2008 Blood, 111(7):3751-9). Human JOSD1 protein was purified according to standard protocols. Recombinant JOSD1 was tested for activity in a Ubiquitin-AMC assay in the presence or absence of inhibitors. For this assay, 10 nM JOSD1 was pre-incubated with different concentrations of inhibitors or DMSO as a control in 50 mM 4-(2-hydroxyethyl)-1-piperazineethanesulfonic acid (HEPES) pH 7.6, 0.5 mM ethylenediaminetetraacetic acid (EDTA), 11 μM ovalbumin, 5 mM dithiothreitol (DTT). The reaction was incubated for 6 hours at room temperature prior to the addition of 2 μM Ubiquitin-AMC (Boston Biochem) substrate. The initial rate of the reaction was measured by collecting fluorescence data at one-minute intervals over a 30-minute period using a Clariostar® fluorescence plate reader at excitation and emission wavelengths of 345 and 445 nm, respectively. The calculated initial rate values were plotted against inhibitor concentrations to determine $IC_{50}$ values.

Target engagement assay. HEL-FLAG/HA-JOSD1 cells were treated with the indicated concentrations of compound for 16 hours, lysed, and incubated with 0.25 μg UbiQ-057 (PA-Ub) probe for 30 minutes at room temperature. The ability of compounds to block JOSD1 labeling by PA-Ub probe was visualized by western blotting.

Flow cytometry. Flow cytometry was carried out as previously described, according to standard protocols (Lamberto, et al., 2017, Cell Chem Biol., 224(12):1490-500 e11). Briefly, JOSD1 was knocked down in SET-2 cells. After 3 days of selection with puromycin, cells were collected and fixed, protein levels of JAK2 were detected by flow-cytometry with JAK2 primary antibody (4° C., overnight) and PE-staining (1 hour, room temperature). A FACSCanto™ flow cytometry machine equipped with FACSDiva™ analytical software was used for analyzing the percentage of JAK2-positive cells.

Comprehensive selectivity profiling. Comprehensive selectivity profiling was carried out as previously described (Lamberto, et al., 2017, Cell Chem Biol., 224(12):1490-500 e11). Briefly, comprehensive selectivity profiling of each compound was performed by utilizing purified enzyme biochemical assays and chemical proteomics. Selectivity was analyzed against a panel of 41 purified DUB enzymes, using ubiquitin-AMC as substrate.

Activity Based Protein Profiling (ABPP) assay. DUB targets were investigated using competitive ABPP with quantitative mass spectrometry. The ability to block labeling of 50 DUBs by ubiquitin-based DUB activity-based probes was quantitatively measured in HEK-293T lysates.

DUB ABPP of Compound Targets. Activity-based probes biotin-Ub-PA (UbiQ-076) and biotin-Ub-VME (UbiQ-054) were obtained from UbiQ Bio. DUB Activity based protein profiling was performed using conditions modified from those in Schauer, et al., 2020, Scientific Reports, 10:1-15, based on work by Lawson, et al., 2017 Oncotarget, 8:51296-316. HEK 293T cells were lysed (50 mM Tris pH 8.0, 150 mM NaCl, 5 mM $MgC_2$, 0.5 mM EDTA, 0.5% NP-40, 10% glycerol, 1 mM tris(2-carboxyethyl)phosphine (TCEP), protease and phosphatase inhibitors) and the lysate was clarified by centrifugation, then diluted to 10 mg/mL. 200 μL aliquots were incubated at the indicated compound concentrations or DMSO for 5 hours at room temperature, final DMSO concentration 0.5%. Afterwards, the treated lysates were incubated with 1 μM each of Biotin-Ub-PA and Biotin-Ub-VME for 90 minutes at room temperature. 25 μL magnetic streptavidin Sepharose® slurry was added to each sample, followed by incubation at room temperature for 30 minutes with end-to-end rotation. After immobilizing the beads using a magnetic rack, the supernatant was subjected to an additional streptavidin pulldown as described above, and the pooled beads were washed (3×0.2% sodium dodecyl sulfate (SDS), 3× phosphate-buffered saline (PBS), 2× double distilled water (dd$H_2O$)). After the final wash, supernatant was removed, and the resin was flash frozen and stored at −80° C.

Antibodies. The following antibodies were purchased from Cell Signaling Technology™ (Danvers, MA): JAK1 (mouse, #50996), JAK2 (rabbit, #3230S), JAK3 (rabbit, #8827), Tyrosine Kinase 2 (TYK2) (rabbit, #14193), phospho-signal transducer and activator of transcription 3 (pSTAT3) (rabbit, #9131), STAT3 (rabbit, #4904), pSTAT5 (rabbit, #4322), STAT5 (mouse, #4807), pAKT (rabbit, #13038), AKT (rabbit, #9272) (mouse, #2920), phospho-p44/42 mitogen-activated protein kinase (MAPK)(Erk1/2) Thr202/Tyr204 (rabbit, #4370), p44/42 MAPK (Erk1/2) (rabbit, #4695), MCL-1 (rabbit, #5453), UCHL1 (rabbit, #13179), and anti-GAPDH (14C10) (rabbit monoclonal antibody (mAb), #2118). All antibodies were used at 1:1000 for immunoblotting, with the exception of anti-glyceraldehyde 3-phosphate dehydrogenase (GAPDH), which was used at 1:5000. JOSD1 antibodies were purchased from Abcam® (rabbit, Ab178341) and Thermo Fisher (rabbit, PA5-71125). Hemagglutinin (HA)-tag, suppressor of cytokine signaling 1 (SOCS1) and USP30 antibodies were purchased from Abcam® (HA-tag (mouse, ab49969), SOCS1 (goat, ab9870), and USP30 (rabbit, ab235299)). Antibodies were used at 1:1000 for immunoblotting. FLAG®-tag antibody was obtained from Thermo Fisher (rat, MAI-142) and used at 1:1000 for immunoblotting. Ubiquitin (P4D1) (sc-8017) was purchased from Santa Cruz Biotechnology®, Inc. and used at 1:1000 for immunoblotting.

Quantitative real-time polymerase chain reaction (qPCR). Following the loss of JOSD1 via genetic knockdown (KD) or knockout (KO), mRNA was extracted using the RNeasy® Mini Kit (Qiagen®) and converted to cDNA using SuperScript® III reverse transcriptase (ThermoFisher). Real-time PCR was carried out in a 96-well plate using TaqMan® probes and a 7500 FAST Real-Time PCR system (ThermoFisher). Relative gene expression was calculated by comparison to a GAPDH reference probe. The TaqMan® probes for qPCR were purchased from ThermoFisher: JAK2 (Hs01078136_ml), JOSD1 (Hs00208420_ml), GAPDH (Hs02786624_g1).

Protein expression and purification. A construct of full-length human JOSD1 (residues 1-202) in the pET28b vector was over-expressed in *E. coli* BL21 (DE3) in LB medium in the presence of 50 mg/mL of kanamycin. Cells were grown at 37° C. to an OD of 0.8, cooled to 16° C., induced with 500 mM isopropyl-1-thio-D-galactopyranoside, incubated overnight at 16° C., collected by centrifugation, and stored at −80° C. Cell pellets were sonicated in lysis buffer (25 mM Tris (pH 8.0), 1 M NaCl, and 10 mM 2-mercaptoethanol (BME)), and the resulting lysate was centrifuged at 30,000 g for 30 minutes. Nickel-nitrilotriacetic acid (Ni-NTA) beads (Qiagen®) were mixed with lysate supernatant for 30 minutes and washed with buffer A. Beads were washed with wash buffer (25 mM Tris (pH 8.0), 1 M NaCl, 10 mM BME, and 25 mM imidazole) and eluted with elution buffer (25 mM Tris (pH 8.0), 1 M NaCl, 10 mM BME, and 300 mM imidazole). The eluent was concentrated and passed through a Superdex® 200 10/300GL column (GE Healthcare) in a buffer containing 25 mM HEPES (pH 7.5), 200 mM NaCl, and 1 mM TCEP. Fractions were pooled, concentrated to 20 mg/mL, and frozen at −80° C.

In vitro JOSD1 activity assay. Recombinant full-length JOSD1 was tested for activity in a Ubiquitin-AMC assay in the presence or absence or inhibitors. For this assay, 10 nM JOSD1 was pre-incubated with different concentrations of inhibitors or DMSO as a control in 50 mM Tris 8.0, 0.5 mM EDTA, 10 mM ovalbumin, 5 mM DTT. The reaction was incubated for 6 h at room temperature prior to the addition of 2 mM Ubiquitin-AMC (Boston Biochem) substrate. The initial rate of the reaction was measured by collecting fluorescence data at one-minute intervals over a 30-minute period using a CLARIOstar® fluorescence plate reader at excitation and emission wavelengths of 345 and 445 nm, respectively. The calculated initial rate values were plotted against inhibitor concentrations to determine $IC_{50}$ values.

Normal bone marrow liquid culture proliferation and colony assay studies. Human bone marrow cells from healthy donors were obtained from STEMCELL Technologies™ INC., Vancouver, British Columbia, Canada. Normal bone marrow was investigated for sensitivity to targeted Josd1 inhibitor treatment in liquid culture (Iscove's Modified Dulbecco's Medium (MDM)) (STEMCELL Technologies™ INC., Vancouver, British Columbia, Canada) (cat #36150), supplemented with 20% FBS and StemSpan™ CC100 (100×) serum-free culture supplement for expansion of human hematopoietic cells (STEMCELL Technologies™ INC., Vancouver, British Columbia, Canada).

Normal human bone marrow was also analyzed in a colony assay: 24-well plates seeded with 200 cells/well in MethoCult™ H4434 Classic (methylcellulose-based medium with recombinant cytokines for human cells) (STEMCELL Technologies™ INC., Vancouver, British Columbia, Canada). The plates contained targeted JOSD1 inhibitors at the indicated concentrations. Plates were incubated at 37° C. in 5% $CO_2$ for >1 week, and then myeloid and erythroid colonies (early progenitors with erythroid and myeloid components: colony-forming unit for granulocytes and macrophages (CFU-GM), CFU-erythroid (E), BFU-E, and CFU-granulocyte, erythroid, macrophage, megakaryocyte (GEMM) were counted on an inverted microscope.

AML liquid culture proliferation and colony assay studies. Frozen vials of bone marrow from AML patients identified as harboring JAK2-V617F were previously Ficoll®-purified to obtain mononuclear cells and thawed prior to use in studies. AML cells were investigated for sensitivity to targeted JOSD1 inhibitor treatment in liquid culture (Iscove's Modified Dulbecco's Medium (MDM) (STEMCELL Technologies® INC., Vancouver, British Columbia, Canada) (cat #36150), supplemented with 20% FBS. All bone marrow samples from AML patients were obtained under approval of the Dana-Farber Cancer Institute Institutional Review Board.

Sample Prep for Mass Spectrometry (MS) Analysis. Streptavidin beads were resuspended in 95 μL 100 mM Tris pH 8.0. Each sample was denatured with 0.1% RapiGest™, reduced (10 mM dithiothreitol), alkylated (22.5 mM iodoacetamide), and digested with trypsin at 37° C. overnight. The next day, beads were captured using a magnetic rack, and supernatants were acidified with 10% TFA, incubated at 37° C. for 30 minutes, and centrifuged at 14,000 rpm for 15 minutes at 4° C. to remove rapigest. Peptides were then desalted by C18 and dried by vacuum centrifugation.

Dried peptides were reconstituted in 40 μL 50 mM pH 8.0 tetraethylammonium bromide (TEAB), and ¼ unit of Tandem Mass Tag™ (TMT™) reagent was added and reactions incubated at room temperature for 1 h. TMT™ reactions were pooled and treated with hydroxylamine according to the manufacturer's instructions. Peptide mixtures were then dried, reconstituted in 100 mM ammonium bicarbonate and desalted by SP3 buffer (Hughes, et al., 2014, Molecular systems biology, 10:757). Eluted peptides were then analyzed by nanoscale liquid chromatography coupled to tandem mass spectrometry (nanoLC-MS) as described in Ficarro, et al., 2009, Anal Chem, 81:3440-47 with a NanoAcquity UPLC® system (Waters®, Milford, MA) interfaced to a QExactive™ HF mass spectrometer (Thermofisher Scientific, San Jose, CA). TMT™ labeled peptides were injected onto a precolumn (4 cm POROS™ 10R2, Applied Biosystems®, Framingham, MA), resolved on an analytical column (30 μm I.D.×50 cm packed with 5 μm Monitor C18) and introduced to the mass spectrometer by electrospray ionization (ESI) (spray voltage=3.5 kV, flow rate ~30 nL/min). The mass spectrometer was operated in data dependent mode such that the 15 most abundant ions in each MS scan (m/z 300-2000, 120K resolution, target=3E6, lock mass for 445.120025 enabled) were subjected to MS/MS (m/z 100-2000, 30K resolution, target=1E5, max fill time=100 ms). Dynamic exclusion was selected with a repeat count of 1 and an exclusion time of 30 seconds. MS/MS data was extracted to .mgf using multipliers scripts (Alexander, et al., 2017, Proteomics 17:15-16; Askenazi, et al., 2009, Nat Methods, 6:240-41 and searched against a forward-reverse human NCBI refseq database using Mascot version 2.6.2. Search parameters specified fixed cysteine carbamidomethylation, fixed N-terminal and lysine TMT™ labelling, and variable methionine oxidation. Additional multipliers scripts were used to filter results to 1% false discovery rate (FDR) and derive protein-level aggregate reporter ion intensities using peptides mapping uniquely into the genome.

Statistical Analysis. Data are presented as mean t standard deviation (S.D.) or standard error of the mean (SEM) as indicated. A student's t test was used to determine statistically significant differences (*$p<0.05$, **$p<0.01$) using GraphPad Prism software.

Example 2: Synthesis of compound (S)-1-cyano-N-(6-(3,5-dimethylisoxazol-4-yl)benzo[d]thiazol-2-yl) pyrrolidine-3-carboxamide (1)

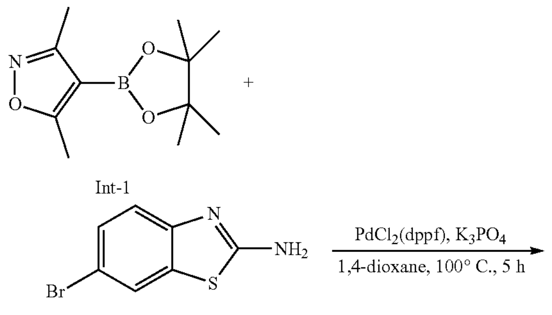

Int-1

Int-2

-continued

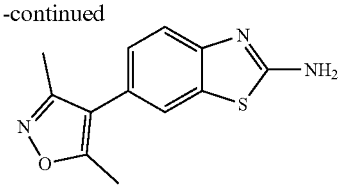

Int-3

A mixture of 6-bromobenzo[d]thiazol-2-amine (Int-2, 1.36 g, 5.9 mmol), 3,5-dimethyl-4-(4,4,5,5-tetramethyl-1,3,2-dioxaborolan-2-yl)isoxazole (Int-1, 1.324 g, 5.9 mmol), $PdCl_2$(dppf) (484 mg, 0.6 mmol) and $K_3PO_4$ (3.780 g, 17.8 mmol) in 1,4-dioxane (80 mL) was stirred at 100° C. under $N_2$ for 5 h. The mixture was concentrated under vacuum. The residue was diluted with water (100 mL) and extracted with ethyl acetate (150 mL×3), the combined organic was washed with brine (100 mL×3), dried over anhydrous $Na_2SO_4$, filtered, concentrated under vacuum, and purified by column chromatography on silica gel (petroleum ether (PE)/ethyl acetate (EtOAc)=1/1) to get intermediate Int-3 as light yellow solid (350 mg, yield 24.07%).

LCMS (m/z): 246.0$[M+H]^+$.

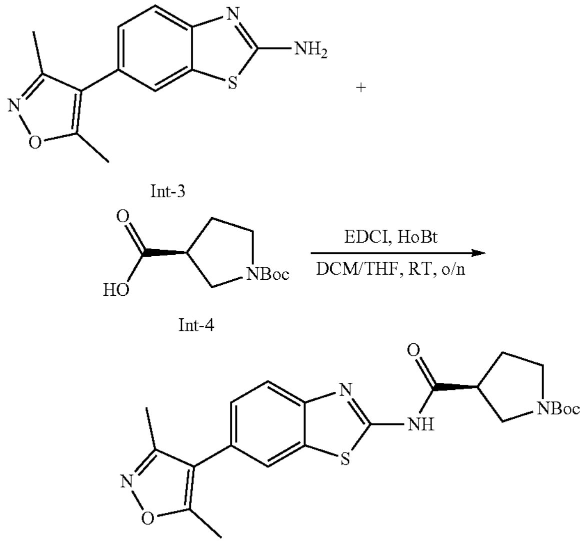

Int-3

Int-4

Int-5

A mixture of (S)-1-(tert-butoxycarbonyl)pyrrolidine-3-carboxylic acid (Int-4, 527 mg, 2.4 mmol), 1-ethyl-3-(3-dimethylaminopropyl)carbodiimide (EDCI) (469 mg, 2.4 mmol) and hydroxybenzotriazole (HOBt) (248 mg, 1.8 mmol) in DCM (20 mL) was stirred at room temperature for 10 minutes, and then intermediate Int-3 (300 mg, 1.2 mmol) was added. The mixture was stirred at room temperature overnight, subsequently diluted with water (100 mL), and extracted with ethyl acetate (50 mL×3). The combined organic layers were washed with brine (50 mL×3), dried over anhydrous $Na_2SO_4$, filtered, concentrated under vacuum, and purified by preparative thin-layer chromatography (TLC) to get intermediate Int-5 as light yellow solid (310 mg, yield 57.34%).

LCMS (m/z): 443.0 $[M+H]^+$.

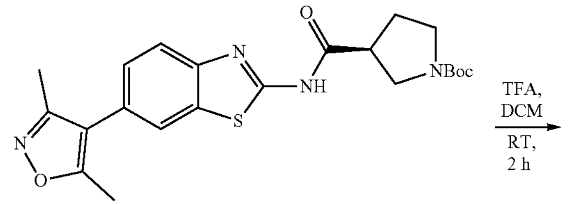

Int-5

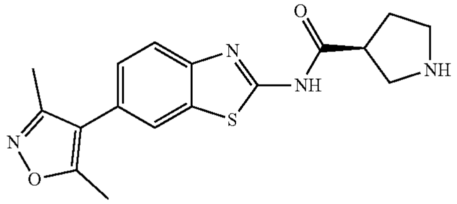

Int-6

A mixture of intermediate Int-5 (150 mg, 0.3 mmol) and TFA (3 mL) in DCM (5 mL) was stirred at room temperature for 2 hours, the mixture was concentrated under vacuum to leave crude intermediate Int-6 as light brown oil (80 mg, yield 69%).

LCMS (m/z): 343.0 $[M+H]^+$.

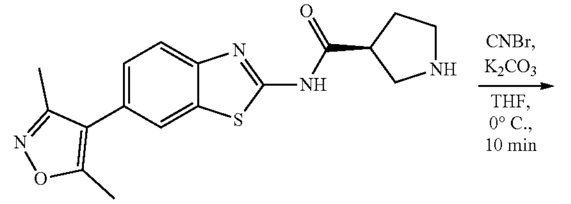

Int-6

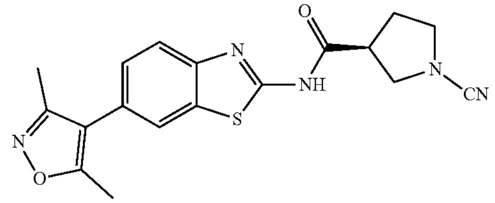

1

To a mixture of intermediate 6 (80 mg, 0.2 mmol) and $K_2CO_3$ (229 mg, 0.7 mmol) in THF (5 mL) was added BrCN (74 mg, 0.7 mmol), the mixture was stirred at 0° C. for 10 minutes and filtered, the filtrate was purified by prep-TLC (PE/EtOAc=5/1) followed by preparative high-performance liquid chromatography (prep-HPLC) to afford compound 1 as white solid (41.39 mg, yield 48.20%).

LCMS (m/z): 368.0 $[M+H]^+$.

$^1H$ NMR ($CDCl_3$, 400 MHz): δ 7.822 (d, J=8.4 Hz, I H), 7.72 (d, J=1.2 Hz, 1H), 7.36 (dd, $J_1$=1.6 Hz, $J_2$=8.0 Hz, 1H), 3.84-3.64 (m, 3H), 3.57-3.50 (m, 1H), 3.30-3.22 (m, 1H), 2.45 (s, 3H), 2.38-2.27 (m, 5H).

Example 3: Synthesis of (S)-1-cyano-N-(7-(3,5-dimethylisoxazol-4-yl)benzo[d]thiazol-2-yl)pyrrolidine-3-carboxamide (2)

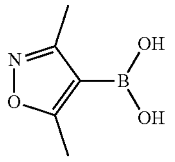

+

Int-7

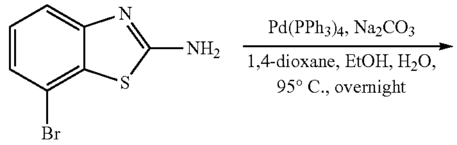

Int-8

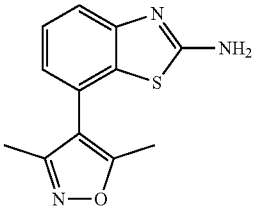

Int-9

2-amino-7-bromobenzothiazole (Int-8, 0.69 g, 3.0 mmol), 3,5-dimethylisoxazole-4-boronic acid (Int-7, 0.64 g, 4.0 mmol), sodium carbonate (0.63 g, 6.0 mmol) were mixed in a solution of 1,4-dioxane, EtOH, and $H_2O$ (16 mL/4 mL/2 mL). $N_2$ was bubbled through the suspension for 10 to 15 minutes, followed by addition of tetrakis(triphenylphosphine)palladium (0) ($Pd(PPh_3)_4$) (10 mol %, 0.34 g, 0.3 mmol). The mixture was purged with $N_2$ for another 5 minutes before stirring at 95° C. overnight under $N_2$. Then the mixture was concentrated under reduced pressure, diluted with EtOAc (100 mL), and washed with saturated $NH_4Cl$ (100 mL×2). Combined aqueous layers were extracted with EtOAc (100 mL). Combined organic layers were washed once with brine (100 mL), dried over anhydrous $Na_2SO_4$, filtered, and evaporated under reduced pressure to afford a crude material, which was further purified by flash chromatography (50% EtOAc in hexanes) to afford intermediate Int-9 (0.39 g, yield 52.3%).

LC/MS (ESI) m/z 245.88 $[M+H]^+$; calcd for $C_{12}H_{12}N_3OS^+$: 246.07.

$^1H$ NMR (500 MHz, DMSO) δ 7.99 (s, 2H), 7.41 (dd, J=8.0, 1.1 Hz, 1H), 7.36 (t, J=7.7 Hz, 1H), 7.01 (dd, J=7.3, 1.1 Hz, 1H), 2.29 (s, 3H), 2.12 (s, 3H).

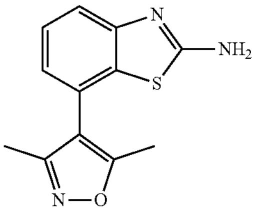

+

Int-9

-continued

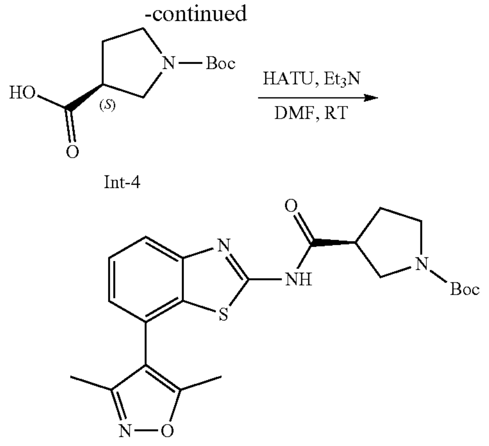

Int-4

Int-10

7-(3,5-dimethylisoxazol-4-yl)benzo[d]thiazol-2-amine (Int-9, 0.05 g, 0.2 mmol) and (S)-1-Boc-pyrrolidine-3-carboxylic acid (Int-4, 0.06 g, 0.25 mmol) were added into a mixture of DCM/DMF (2 mL/0.5 mL) with $Et_3N$ (0.14 mL, 1.0 mmol). Hexafluorophosphate azabenzotriazole tetramethyl uronium (HATU) (0.12 g, 0.3 mmol) was added to the mixture in one portion, and the resulting solution was stirred at room temperature overnight. The crude was then directly purified by flash chromatography (80% EtOAc in hexanes) to afford desired product intermediate Int-10 (0.072 g, quantitative yield (quant.)).

LC/MS (ESI) m/z 387.27 (M-t-Butyl); $[M+H]^+$ calcd for $C_{22}H_{27}N_4O_4S^+$: 443.54.

$^1H$ NMR (500 MHz, DMSO) δ 7.81 (d, J=7.8 Hz, 1H), 7.55 (t, J=7.8 Hz, 1H), 7.26 (d, J=7.0 Hz, 1H), 3.53 (t, J=9.0 Hz, 1H), 3.41 (m, 1H), 2.30 (s, 3H), 2.23-2.13 (m, 1H), 2.11 (s, 3H), 2.06 (m, H), 1.40 (s, 9H).

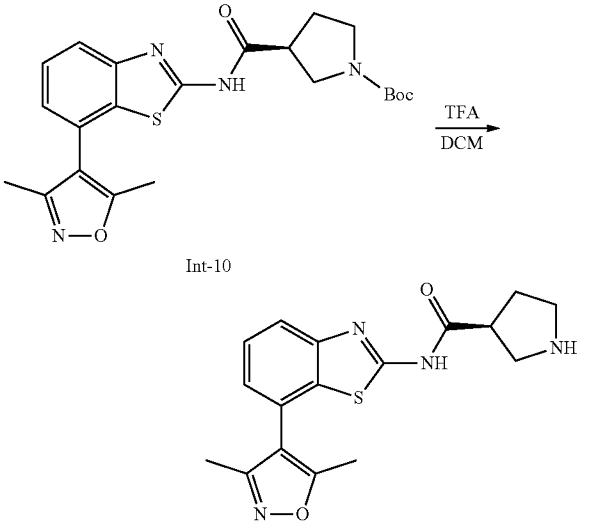

Int-10

Int-11 tert-Butyl (S)-3-((7-(3,5-dimethylisoxazol-4-yl) benzo[d] thiazol-2-yl) carbamoyl) pyrrolidine-1-carboxylate (Int-10, 0.09 g, 0.2 mmol) was dissolved in DCM (1 mL), prior to the addition of TFA (2 mL). The resulting solution was stirred at room temperature for 2 h, then concentrated under reduced pressure. The crude material was flushed through flash chromatography to remove excess TFA and afford free amine intermediate Int-11 (0.07 g, quant.), which was used without further purification.

LC/MS (ESI) m/z 343.17. $[M+H]^+$ calcd for $C_{17}H_{19}N_4O_2S^+$: 343.42.

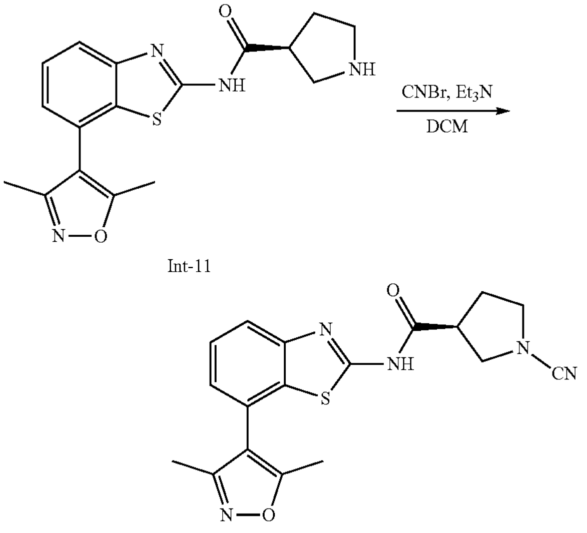

Int-11

2

(S)—N-(7-(3,5-dimethylisoxazol-4-yl) benzo[d]thiazol-2-yl) pyrrolidine-3-carboxamide (11, 0.07 g, 0.2 mmol) was dissolved in anhydrous DCM (2 mL) under nitrogen. $Et_3N$ (0.062 mL, 0.4 mmol) was added, and the solution was stirred at 0° C. prior to the addition of 3 M solution of CNBr in DCM (0.1 mL, 0.3 mmol) was added drop wise. The reaction mixture was then slowly warmed up to room temperature and stirred for 1 h. The mixture was directly purified by flash chromatography (20% to 50% EtOAc in hexanes), followed by prep-HPLC (MeCN/$H_2O$ with 0.0425% TFA) to afford compound 2 (0.029 g, yield 39.5%).

LC/MS (ESI) m/z 367.97; $[M+H]^+$ calcd for $C_{18}H_{18}N_5O_2S^+$: 368.12.

$^1H$ NMR (500 MHz, DMSO) δ 7.82 (dd, J=8.1, 0.9 Hz, 1H), 7.61-7.51 (m, 1H), 7.28 (dd, J=7.4, 0.9 Hz, 1H), 3.68-3.60 (m, 1H), 3.56 (dd, J=9.7, 5.9 Hz, 1H), 3.48-3.41 (m, 2H), 3.39 (dd, J=13.5, 6.8 Hz, 1H), 2.31 (s, 3H), 2.21 (tt, J=12.8, 6.4 Hz, 1H), 2.14-2.04 (m, 4H).

Example 4: General Synthetic Procedure 1

Step 1: Amines (1.0 eq.), carboxylic acids (1.2 eq.) $Et_3N$ (5.0 eq.) and HATU (1.5 eq.) were added into DMF (3-5 mL). The mixture was stirred at room temperature overnight. If necessary, the mixture was diluted with EtOAc (50 mL), and washed with brine (30 mL×2) to remove excess DMF. Organic layer was dried over anhydrous sodium sulfate ($Na_2SO_4$), filtered, and concentrated under reduced pressure. The crude material was then purified by flash column chromatography (hexanes/EtOAc/MeOH).

Step 2: Products from last step were dissolved in DCM (2-3 mL) and treated with TFA (2-3 mL). The mixtures were stirred at room temperature until the tert-butyloxycarbonyl protecting group was cleaved tracking by UPLC-MS. The mixture was concentrated and flushed by flash column chromatography (EtOAc/MeOH/0.5% $Et_3N$).

Step 3: Products from last step were dissolved in a mixture of DCM (2-3 mL) and $Et_3N$ (2 eq.) at 0° C. Chloroacetyl chloride (1.2 eq.), or acryloyl chloride (1.2 eq.), or cyanogen bromide (1.2 eq) was added dropwise. The mixture was then stirred at 0° C. for 1 h, and directly purified by flash chromatography (hexanes/EtOAc/MeOH) followed by preparative HPLC (MeOH or $CH_3CN/H_2O$ with 0.0425% TFA) to afford the target products.

Example 5: Synthesis of Compound N N-(6-bromobenzo[d]thiazol-2-yl)-1-cyanoazetidine-3-carboxamide (33)

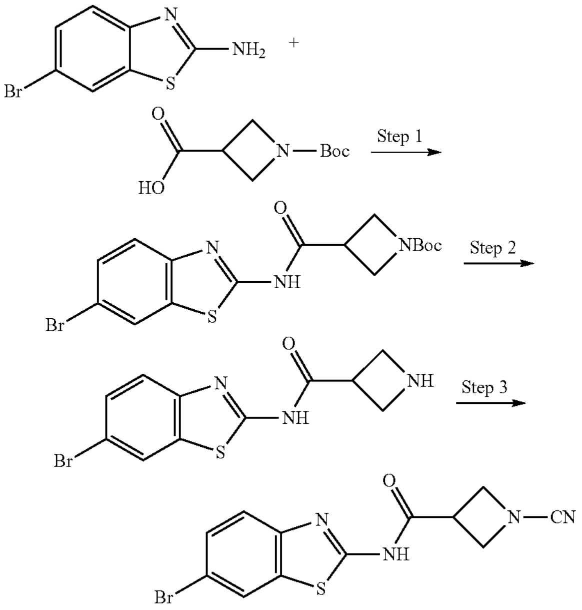

33

Step 1 was preformed according to the procedure in Example 17 with 6-bromobenzo[d]thiazol-2-amine (0.39 g, 1.7 mmol) and 1-(tert-butoxycarbonyl)azetidine-3-carboxylic acid (0.42 g, 2.1 mmol) to afford desired compound (tert-butyl 3-((6-bromobenzo[d]thiazol-2-yl)carbamoyl)azetidine-1-carboxylate (0.21 g, yield 30%).

LC/MS (ESI) m/z 356.07 (M+H-t-butyl); $[M+H]^+$ calcd for $C_{16}H_{19}BrN_3O_3S^+$: 412.03.

Step 2 was performed according to the procedure in Example 17 with tert-butyl 3-((6-bromobenzo[d]thiazol-2-yl)carbamoyl)azetidine-1-carboxylate (0.21 g, 0.5 mmol) to afford N-(6-bromobenzo[d]thiazol-2-yl)azetidine-3-carboxamide was obtained (0.18 g, quant.).

33

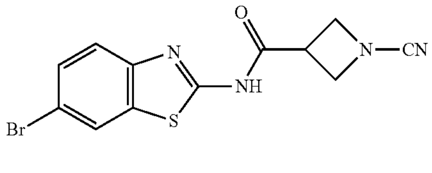

Step 3 was performed according the procedure in Example 17 with N-(4-phenylthiazol-2-yl)azetidine-3-carboxamide (0.06 g, 0.17 mmol) and cyanogen bromide (0.02 g, 0.2 mmol) to afford 33 (36 mg, yield 63%).

$^1H$ NMR (500 MHz, DMSO) δ 12.56 (s, 1H), 8.27 (t, J=4.2 Hz, 1H), 7.68 (d, J=8.6 Hz, 1H), 7.58 (dd, J=8.6, 2.1 Hz, 1H), 4.34 (dt, J=14.0, 7.8 Hz, 4H), 3.82 (tt, J=8.9, 6.3 Hz, 1H).

LC/MS (ESI) m/z 336.77, $[M+H]^+$; calcd for $C_{12}H_{10}BrN_4OS^+$: 336.98.

Example 6: Synthesis of (R)—N-(6-(1-benzyl-1H-pyrazol-4-yl)benzo[d]thiazol-2-yl)-1-cyanopyrrolidine-3-carboxamide (3)

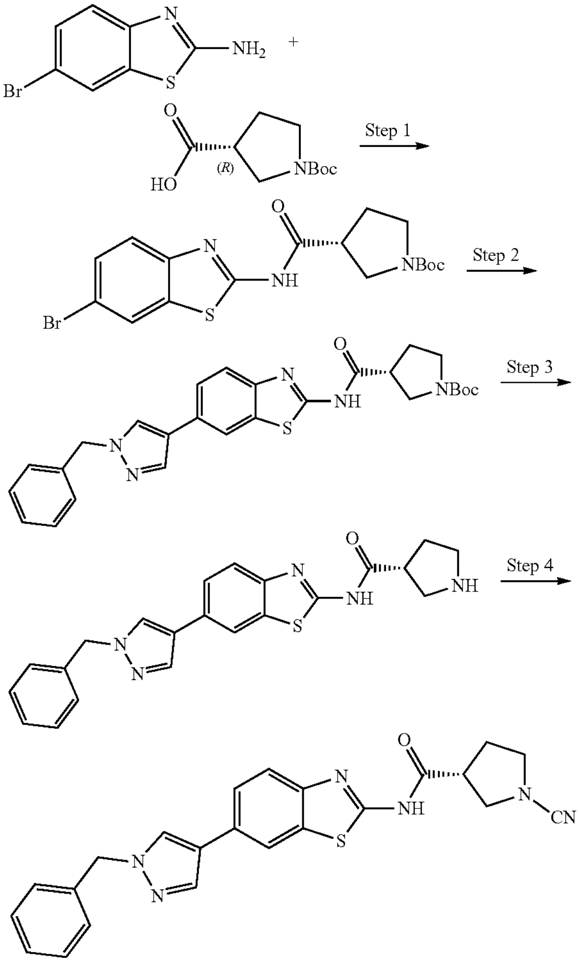

3

Step 1: 6-bromobenzo[d]thiazol-2-amine (0.41 g, 1.8 mmol), (R)-1-(tert-butoxycarbonyl)pyrolidine-3-carboxylic acid (0.47 g, 2.2 mmol), $Et_3N$ (1.2 mL, 9.0 mmol) and HATU (1.03 g, 2.7 mmol) were added sequentially to anhydrous DMF (5 mL). The mixture was stirred at room temperature overnight. The mixture was then diluted with EtOAc (50 mL), and washed with brine (30 mL-2) to remove excess DMF. Organic layer was dried over anhydrous sodium sulfate ($Na_2SO_4$), filtered, and concentrated under reduced pressure. The crude material was then purified by flash column chromatography (hexanes/EtOAc/MeOH) to afford tert-butyl (R)-3-((6-bromobenzo[d]thiazol-2-yl)carbamoyl)pyrrolidine-1-carboxylate (0.72 g, yield 94%).

LC/MS (ESI) m/z 426.27; $[M+H]^+$ calcd for $C_{17}H_{21}BrN_3O_3S^+$: 426.05.

Step 2: tert-Butyl (R)-3-((6-bromobenzo[d]thiazol-2-yl)carbamoyl)pyrrolidine-1-carboxylate (0.064 g, 0.15 mmol) was dissolved in 1,4-dioxane and $H_2O$ (4 mL, 3:1) followed by the addition of 1-benzyl-4-(4,4,5,5-tetramethyl-1,3,2-dioxaborolan-2-yl)-1H-pyrazole (0.09 g, 0.45 mmol), potassium carbonate (0.062 g, 0.45 mmol) and $Pd(PPh_3)_4$ (0.035 g, 0.03 mmol). The mixture was degassed by bubbling through $N_2$ for 10 min, and then heated and stirred at 95° C. for 2-8 h. The reaction was then allowed to cool to room temperature, diluted with EtOAc (50 mL), and washed with saturated ammonium chloride (30 mL×2). The aqueous layer was then extracted with EtOAc (50 mL). The combined organic layers were washed with brine, dried over anhydrous sodium sulfate ($Na_2SO_4$), filtered, and concentrated under reduced pressure to afford a crude material, which was then purified by flash chromatography (hexanes/EtOAc/MeOH) to afford tert-butyl (R)-3-((6-(1-benzyl-1H-pyrazol-4-yl)benzo[d]thiazol-2-yl)carbamoyl)pyrrolidine-1-carboxylate (0.01 g, 13%).

LC/MS (ESI) m/z 503.88; $[M+H]^+$ calcd for $C_{27}H_{30}N_5O_3S^+$: 504.21.

Step 3: tert-Butyl (R)-3-((6-(1-benzyl-1H-pyrazol-4-yl)benzo[d]thiazol-2-yl)carbamoyl)pyrrolidine-1-carboxylate from last step was dissolved in DCM (1 mL) and treated with TFA (1 mL). The mixture was stirred at room temperature until the reaction reached completion, which was monitored by UPLC-MS. The crude mixture was concentrated under reduced pressure and purified by flash column chromatography (EtOAc/MeOH/0.5% $Et_3N$) to afford (R)—N-(6-(1-benzyl-1H-pyrazol-4-yl)benzo[d]thiazol-2-yl)pyrrolidine-3-carboxamide.

3

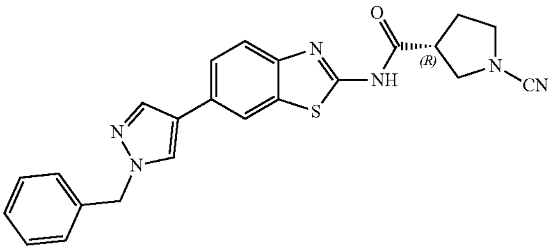

Step 4: (R)—N-(6-(1-Benzyl-1H-pyrazol-4-yl)benzo[d]thiazol-2-yl)pyrrolidine-3-carboxamide from the last step (0.008 g, 0.02 mmol) was dissolved in a mixture of DCM (2 mL) and $Et_3N$ (14 μL, 0.1 mmol) at 0° C. before the addition of 3M cyanogen bromide in DCM (13 μL, 0.04 mmol). The reaction mixture was then stirred at 0° C. for 1 h, and the resulting crude product was directly purified by flash chromatography (hexanes/EtOAc/MeOH) followed by preparative HPLC (MeOH or $CH_3CN/H_2O$ with 0.0425% TFA) to afford compound 3 (4 mg, yield 47%).

$^1H$ NMR (500 MHz, DMSO) δ 12.52 (s, 1H), 8.32 (s, 1H), 8.19 (s, 1H), 7.97 (s, 1H), 7.71 (d, J=8.4 Hz, 1H), 7.65 (d, J=8.4 Hz, I H), 7.37 (m, 2H), 7.30 (m, 3H), 5.36 (s, 2H), 3.69-3.62 (m, 1H), 3.58 (dd, J=9.6, 6.1 Hz, 1H), 3.46 (m, 2H), 3.41-3.34 (m, 1H), 2.23 (dt, 1=13.1, 7.3 Hz, 1H), 2.11 (dt, J=19.7, 7.0 Hz, 1H).

LC/MS (ESI) m/z 428.87; $[M+H]^+$ calcd for $C_{23}H_{21}N_6OS^+$: 429.15.

Example 7: Synthesis of (R)—N-(6-(1-benzyl-1H-pyrazol-4-yl)benzo[d]thiazol-2-yl)-1-cyanopyrrolidine-3-carboxamide (7)

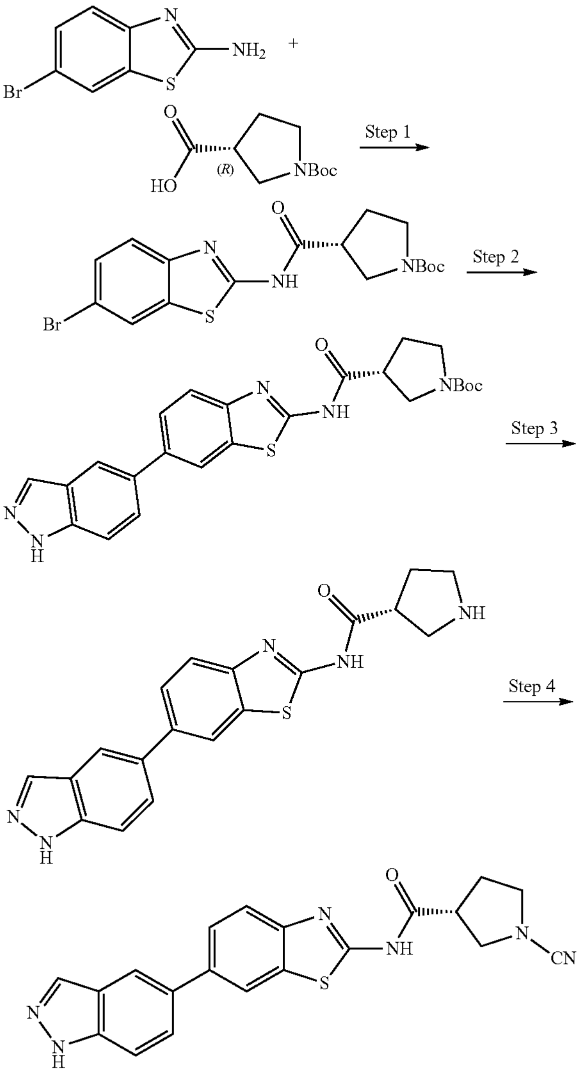

7

Step 1: 6-bromobenzo[d]thiazol-2-amine (0.41 g, 1.8 mmol), (R)-1-(tert-butoxycarbonyl)pyrrolidine-3-carboxylic acid (0.47 g, 2.2 mmol), $Et_3N$ (1.2 mL, 9.0 mmol) and HATU (1.03 g, 2.7 mmol) were added sequentially to anhydrous DMF (5 mL). The reaction mixture was stirred at room temperature overnight. The resulting mixture was then diluted with EtOAc (50 mL), and washed with brine (30 mL×2) to remove excess DMF. The organic layer was dried over anhydrous sodium sulfate ($Na_2SO_4$), filtered, and concentrated under reduced pressure. The crude material was then purified by flash column chromatography (hexanes/EtOAc/MeOH) to afford (R)-3-((6-bromobenzo[d]thiazol-2-yl)carbamoyl)pyrrolidine-1-carboxylate (0.72 g, yield 94%).

LC/MS (ESI) m/z 426.27: $[M+H]^+$ calcd for $C_{17}H_{21}BrN_3O_3S^+$: 426.05.

Step 2: tert-Butyl (R)-3-((6-bromobenzo[d]thiazol-2-yl)carbamoyl)pyrrolidine-1-carboxylate from step 1 (0.064 g, 0.15 mmol) was dissolved in 1,4-dioxane and $H_2O$ (4 mL, 3:1) before the addition of (1H-indazol-5-yl)boronic acid (0.073 g, 0.45 mmol), potassium carbonate (0.062 g, 0.45 mmol), and $Pd(PPh_3)_4$ (0.035 g, 0.03 mmol). The resulting mixture was degassed by bubbling through $N_2$ for 10 min, and then was heated and stirred at 95° C. for 2-8 h. The reaction was then allowed to cool to room temperature, diluted with EtOAc (50 mL), and washed with saturated ammonium chloride (30 mL×2). The aqueous layer was then extracted with EtOAc (50 mL). The combined organic layers were washed with brine, dried over anhydrous sodium sulfate ($Na_2SO_4$), filtered, and concentrated under reduced pressure to afford crude material, which was then purified by flash chromatography (hexanes/EtOAc/MeOH) to afford tert-butyl (R)-3-((6-(1H-indazol-5-yl)benzo[d]thiazol-2-yl)carbamoyl)pyrrolidine-1-carboxylate (0.15 g, quant.).

Step 3: (R)-3-((6-(1H-indazol-5-yl)benzo[d]thiazol-2-yl)carbamoyl)pyrrolidine-1-carboxylate from last step was dissolved in DCM (1 mL) and treated with TFA (1 mL). The mixture was stirred at room temperature until the reaction reached completion, which was monitored by UPLC-MS. The crude mixture was concentrated under reduced pressure and was purified by flash column chromatography (EtOAc/MeOH/0.5% $Et_3N$) to afford (R)—N-(6-(1H-indazol-5-yl)benzo[d]thiazol-2-yl)pyrrolidine-3-carboxamide.

7

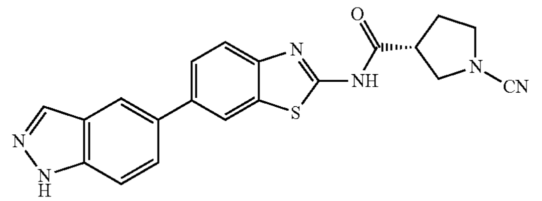

Step 4: (R)—N-(6-(1H-Indazol-5-yl)benzo[d]thiazol-2-yl)pyrrolidine-3-carboxamide from the last step (0.12 g, 0.34 mmol) was dissolved in a mixture of DCM/DMSO (2 mL) and $Et_3N$ (240 μL, 1.7 mmol) at 0° C. before the addition of 3M cyanogen bromide (170 μL, 0.52 mmol). The reaction mixture was then stirred at 0° C. for 1 h, and the resulting crude product was directly purified by flash chromatography (hexanes/EtOAc/MeOH) followed by preparative HPLC (MeOH or $CH_3CN/H_2O$ with 0.0425% TFA) to afford compound 7.

LC/MS (ESI) m z 388.97; $[M+H]^+$ calcd for $C_{20}H_{17}N_6OS^+$: 389.12.

Example 8: Synthesis of (R)—N-(6-([1,1'-biphenyl]-4-yl)benzo[d]thiazol-2-yl)-1-cyanopyrrolidine-3-carboxamide (14)

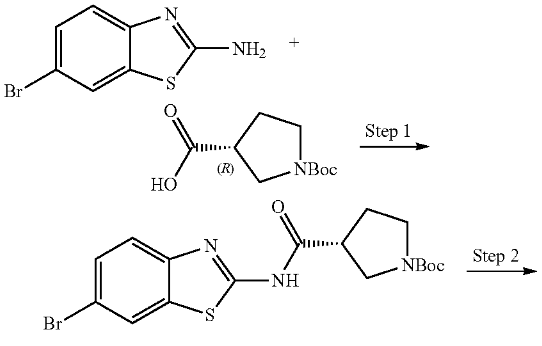

-continued

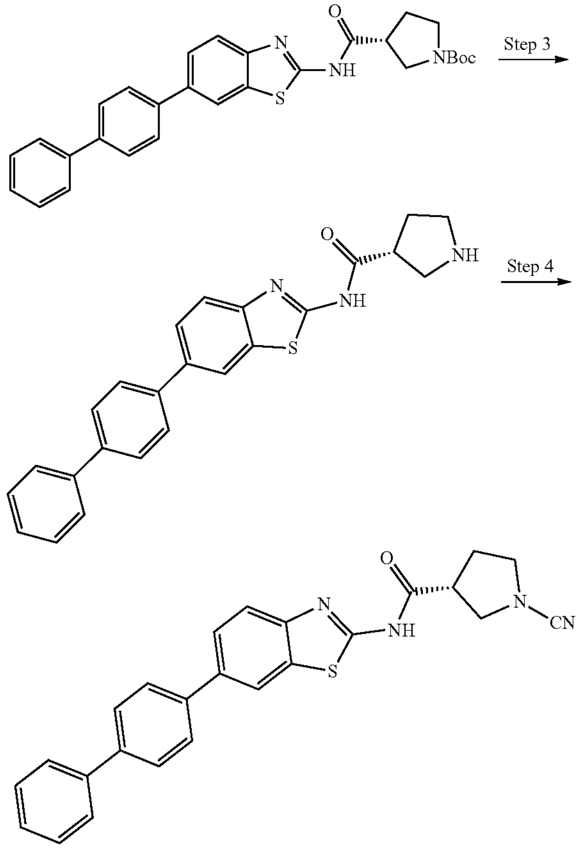

14

Step 1: 6-bromobenzo[d]thiazol-2-amine (0.41 g, 1.8 mmol), (R)-1-(tert-butoxycarbonyl)pyrrolidine-3-carboxylic acid (0.47 g, 2.2 mmol), $Et_3N$ (1.2 mL, 9.0 mmol) and HATU (1.03 g, 2.7 mmol) were added sequentially to anhydrous DMF (5 mL). The reaction mixture was stirred at room temperature overnight. The resulting mixture was then diluted with EtOAc (50 mL), and washed with brine (30 mL×2) to remove excess DMF. The organic layer was dried over anhydrous sodium sulfate ($Na_2SO_4$), filtered, and concentrated under reduced pressure. The crude material was then purified by flash column chromatography (hexanes/EtOAc/MeOH) to afford (R)-3-((6-bromobenzo[d]thiazol-2-yl)carbamoyl)pyrrolidine-1-carboxylate (0.72 g, yield 94%).

LC/MS (ESI) m/z 426.27; $[M+H]^+$ calcd for $C_{17}H_{21}BrN_3O_3S^+$: 426.05.

Step 2: The isolated product tert-butyl (R)-3-((6-bromobenzo[d]thiazol-2-yl)carbamoyl)pyrrolidine-1-carboxylate from step 1 (0.064 g, 0.15 mmol) was dissolved in 1,4-dioxane and $H_2O$ (4 mL, 3:1) before the addition of [1,1'-biphenyl]-4-ylboronic acid (0.089 g, 0.45 mmol), potassium carbonate (0.062 g, 0.45 mmol), and $Pd(PPh_3)_4$ (0.035 g, 0.03 mmol). The resulting mixture was degassed by bubbling through $N_2$ for 10 min, and then was heated and stirred at 95° C. for 2-8 h. The reaction was then allowed to cool to room temperature, diluted with EtOAc (50 mL), and washed with saturated ammonium chloride (30 mL×2). The aqueous layer was then extracted with EtOAc (50 mL). The combined organic layers were washed with brine, dried over anhydrous sodium sulfate ($Na_2SO_4$), filtered, and concentrated under reduced pressure to afford crude material, which was then purified by flash chromatography (hexanes/EtOAc/

MeOH) to afford tert-butyl (R)-3-((6-([1,1'-biphenyl]-4-yl) benzo[d]thiazol-2-yl)carbamoyl)pyrrolidine-1-carboxylate (0.07 g, yield 99/a).

Step 3: tert-Butyl (R)-3-((6-([1,1'-biphenyl]-4-yl)benzo [d]thiazol-2-yl)carbamoyl)pyrrolidine-1-carboxylate from last step was dissolved in DCM (1 mL) and treated with TFA (1 mL). The mixture was stirred at room temperature until the reaction reached completion, which was monitored by UPLC-MS. The crude mixture was concentrated under reduced pressure and was purified by flash column chromatography (EtOAc/MeOH/0.5% $Et_3N$) to afford (R)—N-(6-([1,1'-biphenyl]-4-yl)benzo[d]thiazol-2-yl)pyrrolidine-3-carboxamide.

14

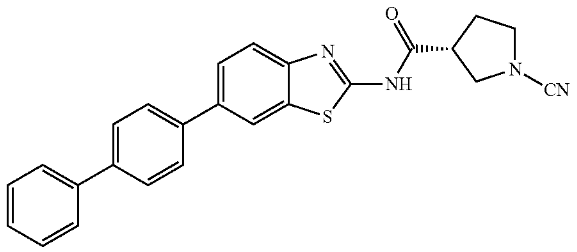

Step 4: (R)—N-(6-([1,1'-Biphenyl]-4-yl)benzo[d]thiazol-2-yl)pyrrolidine-3-carboxamide from the last step (0.056 g, 0.14 mmol) was dissolved in a mixture of DCM (2 mL) and $Et_3N$ (98 μL, 0.7 mmol) at 0° C. before the addition of 3M cyanogen bromide (170 μL, 0.52 mmol). The reaction mixture was then stirred at 0° C. for 1 h, and the resulting crude product was directly purified by flash chromatography (hexanes/EtOAc/MeOH) followed by preparative HPLC (MeOH or $CH_3CN/H_2O$ with 0.0425% TFA) to afford compound 14.

LC/MS (ESI) m/z 425.17; $[M+H]^+$ calcd for $C_{25}H_{21}N_4OS^+$: 425.14.

Example 9: Synthesis of (R)-1-cyano-N-(6-(1-ethyl-1H-pyrazol-4-yl)benzo[d]thiazol-2-yl)pyrrolidine-3-carboxamide (6)

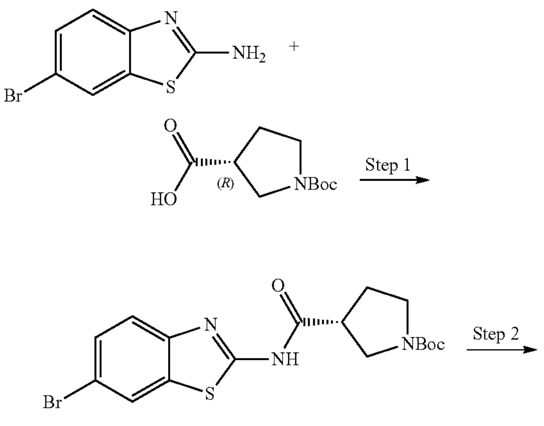

-continued

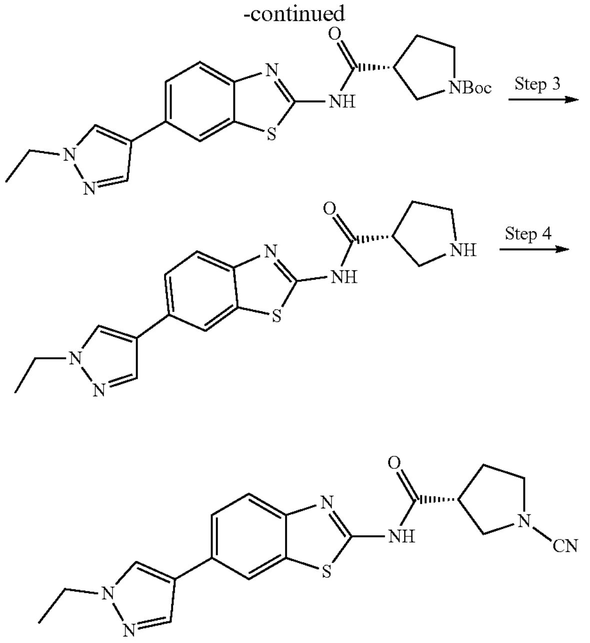

6

Step 1: 6-bromobenzo[d]thiazol-2-amine (0.41 g, 1.8 mmol), (R)-1-(tert-butoxycarbonyl)pyrrolidine-3-carboxylic acid (0.47 g, 2.2 mmol), $Et_3N$ (1.2 mL, 9.0 mmol) and HATU (1.03 g, 2.7 mmol) were added sequentially to anhydrous DMF (5 mL). The reaction mixture was stirred at room temperature overnight. The resulting mixture was then diluted with EtOAc (50 mL), and washed with brine (30 mL×2) to remove excess DMF. The organic layer was dried over anhydrous sodium sulfate ($Na_2SO_4$), filtered, and concentrated under reduced pressure. The crude material was then purified by flash column chromatography (hexanes/EtOAc/MeOH) to afford (R)-3-((6-bromobenzo[d]thiazol-2-yl)carbamoyl)pyrrolidine-1-carboxylate (0.72 g, yield 94%).

LC/MS (ESI) m/z 426.27: $[M+H]^+$ calcd for $C_{17}H_{21}BrN_3O_3S^+$: 426.05.

Step 2: The isolated product tert-butyl (R)-3-((6-bromobenzo[d]thiazol-2-yl)carbamoyl)pyrrolidine-1-carboxylate from step 1 (0.064 g, 0.15 mmol) was dissolved in 1,4-dioxane and $H_2O$ (4 mL, 3:1) before the addition of 1-ethyl-4-(4,4,5,5-tetramethyl-1,3,2-dioxaborolan-2-yl)-1H-pyrazole (0.1 g, 0.45 mmol), potassium carbonate (0.062 g, 0.45 mmol) and $Pd(PPh_3)_4$ (0.035 g, 0.03 mmol). The resulting mixture was degassed by bubbling through $N_2$ for 10 min, and then was heated and stirred at 95° C. for 2-8 h. The reaction was then allowed to cool to room temperature, diluted with EtOAc (50 mL), and washed with saturated ammonium chloride (30 mL×2). The aqueous layer was then extracted with EtOAc (50 mL). The combined organic layers were washed with brine, dried over anhydrous sodium sulfate ($Na_2SO_4$), filtered, and concentrated under reduced pressure to afford crude material, which was then purified by flash chromatography (hexanes/EtOAc/MeOH) to afford tert-butyl (R)-3-((6-(1-ethyl-1H-pyrazol-4-yl)benzo[d]thiazol-2-yl)carbamoyl)pyrrolidine-1-carboxylate (0.05 g, yield 76%).

LC/MS (ESI) m/z 441.88, $[M+H]^+$ calcd for $C_{22}H_{28}N_5O_3S^+$: 442.19.

6

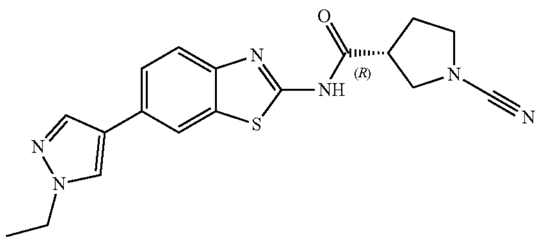

Step 3: tert-Butyl (R)-3-((6-(1-ethyl-1H-pyrazol-4-yl)benzo[d]thiazol-2-yl)carbamoyl)pyrrolidine-1-carboxylate from last step was dissolved in DCM (1 mL) and treated with TFA (1 mL). The mixture was stirred at room temperature until the reaction reached completion, which was monitored by UPLC-MS. The crude mixture was concentrated under reduced pressure and was purified by flash column chromatography (EtOAc/MeOH/0.5% $Et_3N$) to afford (R)—N-(6-(I-ethyl-1H-pyrazol-4-yl)benzo[d]thiazol-2-yl)pyrrolidine-3-carboxamide.

Step 4: (R)—N-(6-(1-ethyl-1H-pyrazol-4-yl)benzo[d]thiazol-2-yl)pyrrolidine-3-carboxamide from the last step (0.041 g, 0.12 mmol) was dissolved in a mixture of DCM (2 mL) and $Et_3N$ (84 μL, 0.6 mmol) at 0° C. before the addition of 3M cyanogen bromide (170 μL, 0.52 mmol). The reaction mixture was then stirred at 0° C. for 1 h, and the resulting crude product was directly purified by flash chromatography (hexanes/EtOAc/MeOH) followed by preparative HPLC (MeOH or $CH_3CN/H_2O$ with 0.0425% TFA) to afford compound 6 (10 mg, 23%).

$^1H$ NMR (500 MHz, DMSO) δ 12.53 (s, 1H), 8.23 (s, 1H), 8.19 (d, J=1.5 Hz, 1H), 7.92 (d, J=0.6 Hz, 1H), 7.72 (d, J=8.4 Hz, 1H), 7.68-7.64 (dd, J=1.7, 8.5 Hz, 1H), 4.21-4.11 (q, J=7.4 Hz, 2H), 3.65 (dd, J=9.6, 7.7 Hz, 1H), 3.59 (dd, J=9.6, 6.0 Hz, 1H), 3.52-3.42 (m, 2H), 3.42-3.35 (m, 1H), 2.24 (dt, J=13.4, 7.5 Hz, 1H), 2.11 (dt, J=14.3, 6.9 Hz, 1H), 1.42 (t, J=7.3 Hz, 3H). LC/MS (ESI) m/z 366.87; $[M+H]^+$ calcd for $C_{18}H_{19}N_6OS^+$: 367.13

Example 10: Synthesis of (S)-1-cyano-N-(4-(3,5-dimethylisoxazol-4-yl)benzo[d]thiazol-2-yl)pyrrolidine-3-carboxamide (5)

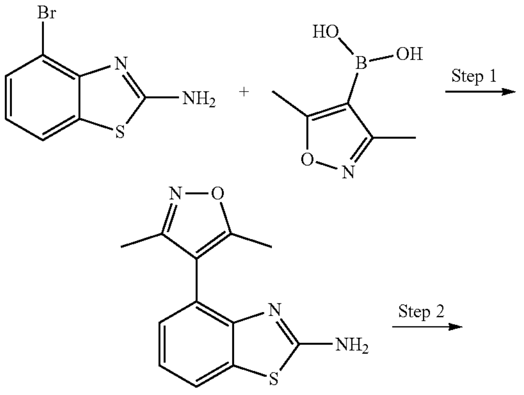

-continued

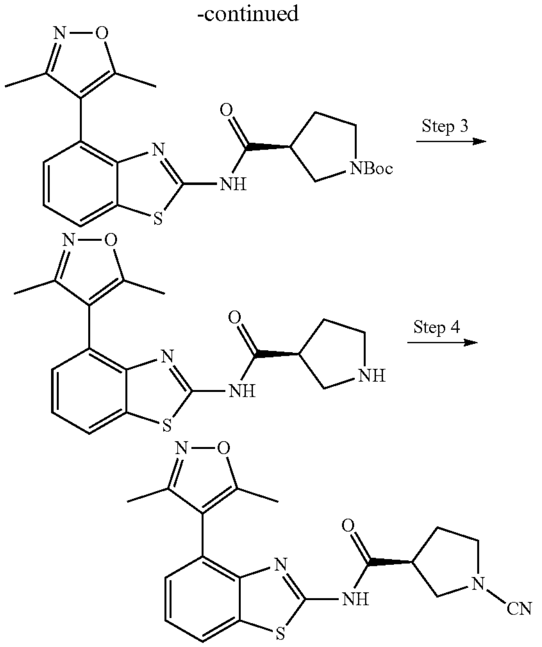

5

Step 1 was performed according to step 1 in Example 22 with 2-amino-4-bromobenzothiazole (0.69 g, 3.0 mmol) and (3,5-dimethylisoxazol-4-yl)boronic acid to afford desired products (4-(3,5-dimethylisoxazol-4-yl)benzo[d]thiazol-2-amine (0.6 g, yield 82%).

LC/MS (ESI) m z 245.98; $[M+H]^+$ calcd for $C_{12}H_{12}N_3OS$: 246.07.

Step 2 was performed according to step 2 in Example 22 with (4-(3,5-dimethylisoxazol-4-yl)benzo[d]thiazol-2-amine (0.05 g, 0.2 mmol) to afford (tert-butyl (S)-3-((4-(3,5-dimethylisoxazol-4-yl)benzo[d]thiazol-2-yl)carbamoyl)pyrrolidine-1-carboxylate (0.092 g, yield 84%).

LC/MS (ESI) m/z 443.08; [M+H]+ calcd for $C_{22}H_{27}N_4O_4S^+$: 443.17.

Step 3 was performed according to step 2 in Example 22 with (tert-butyl (S)-3-((4-(3,5-dimethylisoxazol-4-yl)benzo[d]thiazol-2-yl)carbamoyl)pyrrolidine-1-carboxylate to afford desired product ((S)—N-(4-(3,5-dimethylisoxazol-4-yl)benzo[d]thiazol-2-yl)pyrrolidine-3-carboxamide (0.08 g, quant.)

Step 4 was performed according to step 2 in Example 22 with ((S)—N-(4-(3,5-dimethylisoxazol-4-yl)benzo[d]thiazol-2-yl)pyrrolidine-3-carboxamide (0.072 g, 0.21 mmol) to afford compound 5 (0.026 g, yield 34%).

5

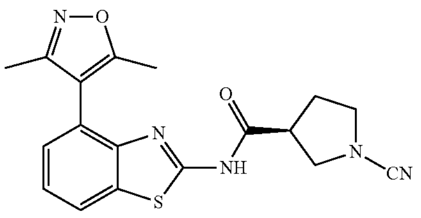

$^1H$ NMR (500 MHz, DMSO) δ 12.60 (s, 1H), 8.10-7.99 (m, 1H), 7.45-7.35 (m, 2H), 3.63 (dd, J=9.6, 7.8 Hz, 1H), 3.57 (dd, J=9.7, 6.0 Hz, 1H), 3.51-3.40 (m, 2H), 3.37 (dd, J=13.8, 6.9 Hz, 1H), 2.31 (s, 3H), 2.27-2.16 (m, 1H), 2.16-2.03 (m, 4H).

LC/MS (ESI) m/z 367.77, $[M+H]^+$ calcd for $C_{18}H_{18}N_5O_2S^+$ 368.12.

Example 11: Synthesis of (S)-1-cyano-N-(5-(3,5-dimethylisoxazol-4-yl)benzo[d]thiazol-2-yl)pyrrolidine-3-carboxamide (4)

4

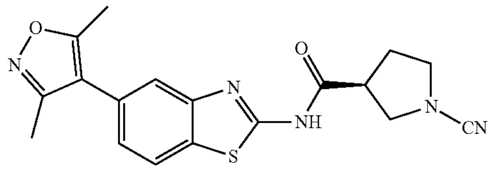

Compound 4 was synthesized in an analogous manner to compound 5 in Example 10 from 2-amino-5-bromobenzothiazole (0.022 g, yield 29%).

$^1$H NMR (500 MHz, DMSO) δ 12.59 (s, 1H), 8.09 (d, J=8.2 Hz, 1H), 7.74 (s, 1H), 7.31 (dd, J=19.8, 9.9 Hz, 1H), 3.70-3.63 (m, 1H), 3.60 (dd, J=9.6, 6.1 Hz, 1H), 3.52-3.37 (m, 3H), 2.43 (s, 3H), 2.28-2.21 (m, 4H), 2.12 (td, J=14.1, 7.1 Hz, 1H).

LC/MS (ESI) m/z 367.87; $[M+H]^+$ calcd for $C_{18}H_{18}N_5O_2S^+$: 368.12.

Example 12: Synthesis of (S)-1-cyano-N-(7-(3,5-dimethylisoxazol-4-yl)benzo[d]thiazol-2-yl)pyrrolidine-3-carboxamide (2)

2

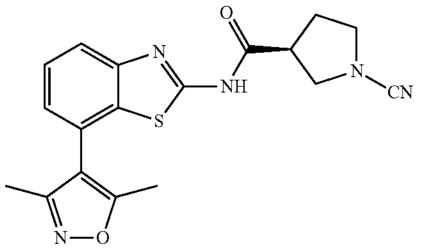

Compound 2 was synthesized in an analogous manner to compound 5 in Example 10 from 2-amino-7-bromobenzothiazole (0.029 g, yield 40%).

$^1$H NMR (500 MHz, DMSO) δ 7.82 (dd, J=8.1, 0.9 Hz, 1H), 7.61-7.51 (m, 1H), 7.28 (dd, J=7.4, 0.9 Hz, 1H), 3.68-3.60 (m, 1H), 3.56 (dd, J=9.7, 5.9 Hz, 1H), 3.48-3.41 (m, 2H), 3.39 (dd, J=13.5, 6.8 Hz, 1H), 2.31 (s, 3H), 2.21 (tt, J=12.8, 6.4 Hz, 1H), 2.14-2.04 (m, 4H).

LC/MS (ESI) m/z 367.97; $[M+H]^+$ calcd for $C_{18}H_{18}N_5O_2S^+$: 368.12.

Example 13: Synthesis of (R)-1-cyano-N-(6-cyclopropylbenzo[d]thiazol-2-yl)pyrrolidine-3-carboxamide (8)

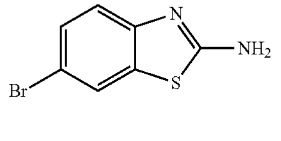

+

-continued

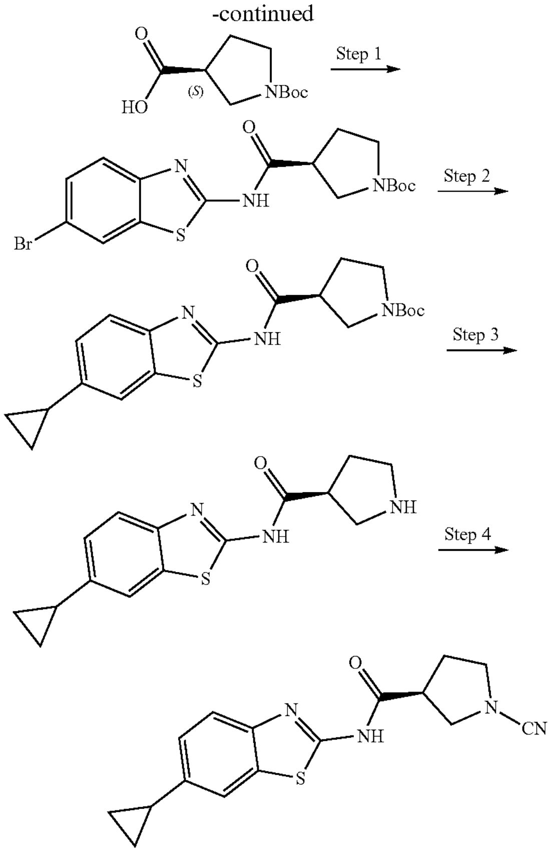

8

Step 1: 6-bromobenzo[d]thiazol-2-amine (0.41 g, 1.8 mmol), (S)-1-(tert-butoxycarbonyl)pyrrolidine-3-carboxylic acid (0.47 g, 2.2 mmol), $Et_3N$ (1.2 mL, 9.0 mmol) and HATU (1.03 g, 2.7 mmol) were added sequentially to anhydrous DMF (5 mL). The reaction mixture was stirred at room temperature overnight. The resulting mixture was then diluted with EtOAc (50 mL), and washed with brine (30 mL×2) to remove excess DMF. The organic layer was dried over anhydrous sodium sulfate ($Na_2SO_4$), filtered, and concentrated under reduced pressure. The crude material was then purified by flash column chromatography (hexanes/EtOAc/MeOH) to afford (S)-3-((6-bromobenzo[d]thiazol-2-yl)carbamoyl)pyrrolidine-1-carboxylate (0.75 g, yield 95%).

LC/MS (ESI) m/z 426.27; $[M+H]^+$ calcd for $C_{17}H_{21}BrN_3O_3S^+$: 426.05.

Step 2: The isolated product tert-butyl (S)-3-((6-bromobenzo[d]thiazol-2-yl)carbamoyl)pyrrolidine-1-carboxylate from step 1 (0.085 g, 0.2 mmol) was dissolved in toluene and $H_2O$ (4 mL/0.5 mL before the addition of potassium cyclopropyltrifluoroborate (0.06 g, 0.4 mmol), potassium carbonate (0.085 g, 0.4 mmol) and $Pd(OAc)_2$ (g, 0.02 mmol), and $P(Cy)_3$ (g, 0.04 mmol). The resulting mixture was degassed by bubbling through $N_2$ for 10 min, and then was heated and stirred at 95° C. for 2-8 h. The reaction was then allowed to cool to room temperature, diluted with EtOAc (50 mL), and washed with saturated ammonium chloride (30 mL×2). The aqueous layer was then extracted with EtOAc (50 mL). The combined organic layers were washed with brine, dried over anhydrous sodium sulfate ($Na_2SO_4$), filtered, and concentrated under reduced pressure to afford crude material, which was then purified by flash chromatography (hexanes/EtOAc/MeOH) to afford tert-butyl (S)-3-((6-cyclopropylbenzo[d]thiazol-2-yl)carbamoyl)pyrrolidine-1-carboxylate (0.05 g, yield 76%).

Step 3: tert-Butyl (S)-3-((6-cyclopropylbenzo[d]thiazol-2-yl)carbamoyl)pyrrolidine-1-carboxylate from last step was dissolved in DCM (1 mL) and treated with TFA (1 mL). The mixture was stirred at room temperature until the reaction reached completion, which was monitored by UPLC-MS. The crude mixture was concentrated under reduced pressure and was purified by flash column chromatography (EtOAc/MeOH/0.5% $Et_3N$) to afford (R)—N-(6-cyclopropylbenzo[d]thiazol-2-yl)pyrrolidine-3-carboxamide.

8

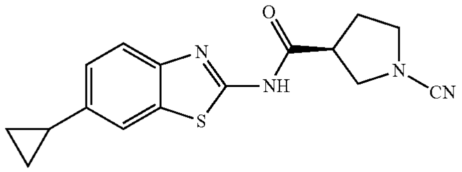

Step 4: (R)—N-(6-cyclopropylbenzo[d]thiazol-2-yl)pyrrolidine-3-carboxamide from the last step (0.062 g, 0.18 mmol) was dissolved in a mixture of DCM/DMSO (2 mL/0.2 mL) with $Et_3N$ (0.13 mL, 0.9 mmol) at 0° C. before the addition of 3M cyanogen bromide (0.12 mL, 0.36 mmol). The reaction mixture was then stirred at 0° C. for 1 h, and the resulting crude product was directly purified by flash chromatography (hexanes/EtOAc/MeOH) followed by preparative HPLC (MeOH or $CH_3CN/H_2O$ with 0.0425% TFA) to afford compound 8 (17 mg, yield 30%).

LCMS ESI (m/z): 317.87: $[M+H]^+$ calcd for $C_{16}H_7N_4OS^+$: 313.11

Example 14. Synthesis of Synthesis of ((S)—N-(benzo[d]thiazol-2-yl)-1-cyanopyrrolidine-3-carboxamide (17)

17

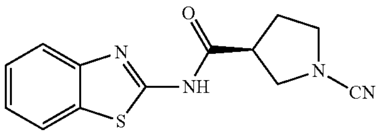

Compound 7 was synthesized in an analogous manner to compound 8 in Example 13 (20 mg, yield 41%).

LCMS ESI (m/z): 272.97: $[M+H]^+$ calcd for $C_{13}H_{13}N_4OS^+$: 273.08.

Example 15: Synthesis of 4-(5-(3,5-dimethylisoxazol-4-yl)benzo[d]thiazol-2-yl)-3-oxopiperazine-1-carbonitrile (49)

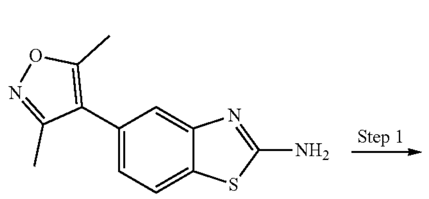

-continued

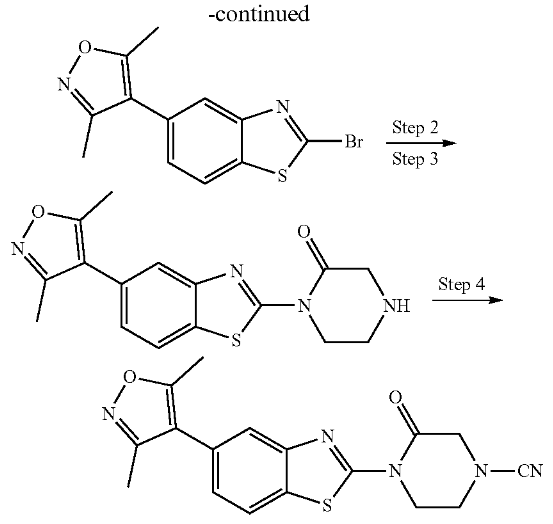

49

Step 1: To a solution of 5-(3,5-dimethylisoxazol-4-yl)benzo[d]thiazol-2-amine, which was synthesized in step 1 of General Procedure 4 (0.075 g, 0.3 mmol) anhydrous MeCN (3 mL), $CuBr_2$ (0.065 g, 0.45 mmol) and t-butyl nitrite (0.046 g, 0.45 mmol) were added at 0° C. The mixture was allowed to warm to room temperature, and then heated to 65° C. and stirred for 4 h. The reaction mixture was allowed to cool to room temperature before dilution with water (30 mL). The resulting mixture was acidified with 12M HCl to pH 2 and extracted with EtOAc (30 mL×2). The combined organic layers were washed with brine, dried over anhydrous $Na_2SO_4$, filtered, and concentrated under reduced pressure to afford a crude product, which was purified by flash chromatography (hexanes/EtOAc/MeOH) to afford a mixture of desired product and chloride-substituted analog, which was used directly in the next step.

LC/MS (ESI) m/z 264.77; $[M+H]^+$; calcd for $C_{12}H_{10}ClN_2OS^+$: 265.02.

Step 2: Products from the last step (0.14 g, 0.5 mmol), 1-Boc-3-oxopiperazine (0.2 g, 1.0 mmol), cesium carbonate (0.65 g, 2.0 mmol), $Pd_2(dba)_3$ (0.046 g, 0.05 mmol), and Xantphos (0.058 g, 0.1 mmol) were dissolved in 1,4-dioxane (5 mL). The resulting mixture was degassed by bubbling through $N_2$ for 10-15 min before heating overnight at 95° C. The reaction mixture was allowed to cool to room temperature before dilution with EtOAc (30 mL). The organic layer was washed with 20% citric acid (20 mL×2), and the combined aqueous layers were extracted with EtOAc (30 mL). The combined organic layers were washed with brine, dried over anhydrous $Na_2SO_4$, filtered and concentrated under reduced pressure to afford a crude product, which was purified by flash chromatography (hexanes/EtOAc/MeOH) to afford the desired product (0.12 g).

LC/MS (ESI) m/z 428.87; $[M+H]^+$; calcd for $C_{21}H_{25}N_4O_4S^+$: 429.16

Step 3: The purified product from last step was dissolved in DCM (2-3 mL) and treated with TFA (2-3 mL). The mixture was stirred at room temperature until the reaction reached completion, which was monitored by UPLC-MS. The crude mixture was concentrated under reduced pressure and was purified by flash column chromatography (EtOAc/MeOH/0.5% $Et_3N$) to afford 1-(5-(3,5-dimethylisoxazol-4-yl)benzo[d]thiazol-2-yl)piperazin-2-one.

49

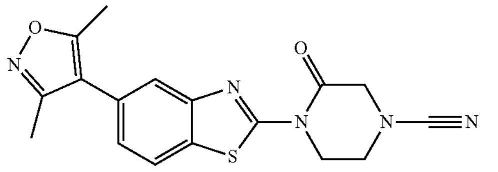

Step 4: 1-(5-(3,5-Dimethylisoxazol-4-yl)benzo[d]thiazol-2-yl)piperazin-2-one the last step (0.04 g, 0.1 mmol, 1.0 eq.) was dissolved in a mixture of DCM (3 mL) and $Et_3N$ (0.07 mL, 0.5 mmol, 5.0 eq.) at 0° C. before the dropwise addition of 3M cyanogen bromide (50 μL, 0.15 mmol, 1.5 eq). The reaction mixture was then stirred at 0° C. for 1 h, and the resulting crude product was directly purified by flash chromatography (hexanes/EtOAc/MeOH) followed by preparative HPLC (MeOH or $CH_3CN/H_2O$ with 0.0425% TFA) to afford compound 49 (16 mg, yield 45%).

$^1H$ NMR (500 MHz, DMSO) δ 8.13 (d, J=8.2 Hz, 1H), 7.86 (s, 1H), 7.38 (d, J=8.2 Hz, 1H), 4.36 (m, 4H), 3.85-3.72 (m, 2H), 2.44 (s, 3H), 2.27 (s, 3H).

LC/MS (ESI) m/z 353.87; $[M+H]^+$ calcd for $C_{17}H_{16}N_5O_2S^+$: 354.10

Example 16: Synthesis of N-((1-cyanoazetidin-3-yl) methyl)benzo[d]thiazole-2-carboxamide (46)

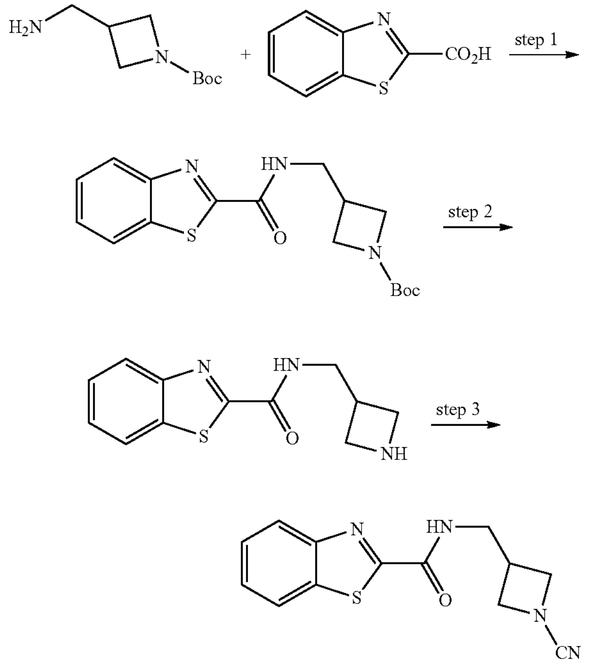

46

Step 1 was preformed according to General Procedure 1 in Example 17 with tert-butyl 3-(aminomethyl)azetidine-1-carboxylate (1.2 eq.), benzo[d]thiazole-2-carboxylic acid (1.0 eq.), $Et_3N$ (3.0 eq.), HATU (1.5 eq.) to afford tert-butyl 3-((benzo[d]thiazole-2-carboxamido)methyl)azetidine-1-carboxylate (0.27 g, yield 42%).

LCMS ESI (m/z): 292.02 (m-t-butyl); $[M+H]^+$ calcd for $C_{17}H_{21}N_3O_3S^+$: 347.43.

Step 2 was performed according to the General Procedure 1 in Example 17 with tert-butyl 3-((benzo[d]thiazole-2-carboxamido)methyl)azetidine-1-carboxylate using 4N HCl in dioxane. The crude reaction mixture was concentrated under reduced pressure to afford crude product N-(azetidin-3-ylmethyl)benzo[d]thiazole-2-carboxamide, which was used directly without any further purification.

46

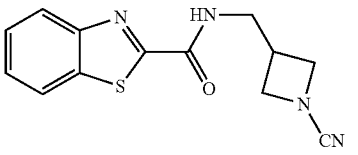

Step 3 was performed according to the General Procedure 1 in Example 17 with N-(azetidin-3-ylmethyl)benzo[d]thiazole-2-carboxamide (1.0 eq.) and cyanogen bromide (1.5 eq.) to afford compound 46 (3 mg, 8%).

$^1H$ NMR (500 MHz, DMSO-$d_6$) δ 9.44 (t, J=6.1 Hz, 1H), 8.24 (d, J=7.9, 1.2 Hz, 1H), 8.15 (d, 1H), 7.71-7.54 (m, 2H), 4.22 (t, J=8.0 Hz, 2H), 3.97 (dd, J=7.7, 5.7 Hz, 2H), 3.55 (t, J=6.5 Hz, 2H), 3.02-2.89 (m, 1H).

LCMS ESI (m/z): 272.97; $[M+H]^+$ calcd for $C_{13}H_{13}N_4OS^+$: 273.08.

Example 17: LCMS ESI Data

Results from LCMS ESI for the remaining compounds, which were synthesized according to above synthetic methods and methods known in the art.

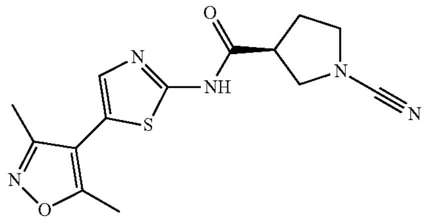 [SMILES: Cc1noc(C)c1-c1cnc(NC(=O)[C@H]2CCN(C#N)C2)s1]

(S)-1-cyano-N-(5-(3,5-dimethylisoxazol-4-yl)thiazol-2-yl)pyrrolidine-3-carboxamide (37)

LCMS ESI (m/z): 317.87; $[M+H]^+$ calcd for $C_{14}H_{16}N_5O_2S^+$: 318.10.

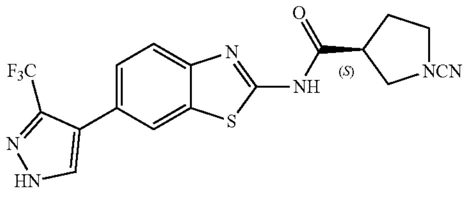

(S)-1-cyano-N-(6-(3-(trifluoromethyl)-1H-pyrazol-4-yl)benzo[d]thiazol-2-yl)pyrrolidine-3-carboxamide (22)

LCMS ESI (m/z): 406.77; $[M+H]^+$ calcd for $C_{17}H_{14}F_3N_6OS^+$: 407.09.

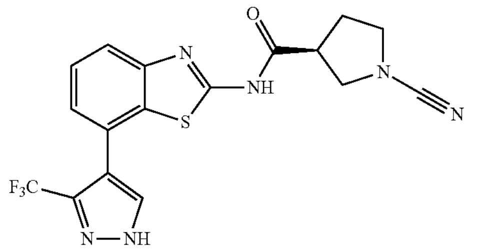 [SMILES: N#CN1CC[C@H](C(=O)Nc2nc3cccc(-c4c[nH]nc4C(F)(F)F)c3s2)C1]

(S)-1-cyano-N-(7-(3-(trifluoromethyl)-1H-pyrazol-4-yl)benzo[d]thiazol-2-yl)pyrrolidine-3-carboxamide (13)

LCMS ESI (m/z): 406.87; $[M+H]^+$ calcd for $C_{17}H_{14}F_3N_6OS^+$: 407.09

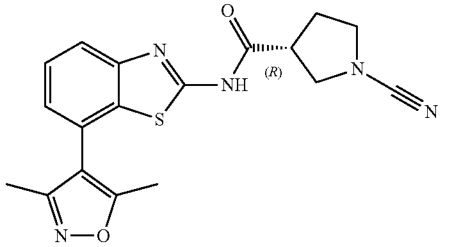

(R)-1-cyano-N-(7-(3,5-dimethylisoxazol-4-yl)benzo[d]thiazol-2-yl)pyrrolidine-3-carboxamide (9)

LCMS ESI (m/z): 367.87; $[M+H]^+$ calcd for $C_{19}H_{18}N_5O_2S^+$: 368.12.

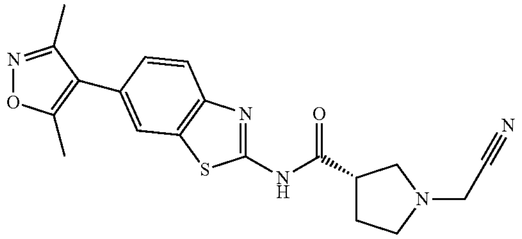 [SMILES: Cc1noc(C)c1-c1ccc2nc(NC(=O)[C@H]3CCN(CC#N)C3)sc2c1]

(S)-1-(cyanomethyl)-N-(6-(3,5-dimethylisoxazol-4-yl)benzo[d]thiazol-2-yl)pyrrolidine-3-carboxamide (40)

LCMS ESI (m/z): 382.17; $[M+H]^+$ calcd for $C_{19}H_{20}N_5O_2S^+$: 382.13.

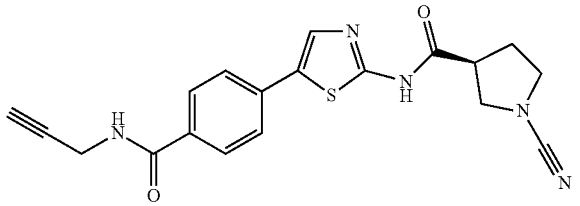 [SMILES: C#CCNC(=O)c1ccc(-c2cnc(NC(=O)[C@H]3CCN(C#N)C3)s2)cc1]

(S)-1-cyano-N-(5-(4-(prop-2-yn-1-ylcarbamoyl)phenyl)thiazol-2-yl)pyrrolidine-3-carboxamide (44)

LCMS ESI (m/z): 379.97: $[M+H]^+$ calcd for $C_{19}H_{18}N_5O_2S^+$: 380.12.

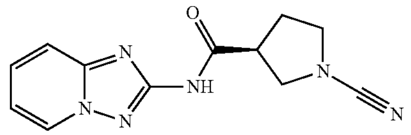 [SMILES: N#CN1CC[C@H](C(=O)Nc2nc3ccccn3n2)C1]

(S)—N-([1,2,4]triazolo[1,5-a]pyridin-2-yl)-1-cyano-pyrrolidine-3-carboxamide (51)

LCMS ESI (m/z): $[M+H]^+$ calcd for $C_{12}H_{13}N_6O$: 257.11.

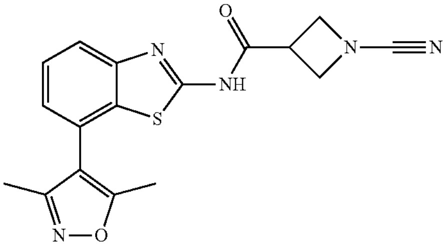 [SMILES: Cc1noc(C)c1-c1cccc2nc(NC(=O)C3CN(C#N)C3)sc12]

1-Cyano-N-(7-(3,5-dimethylisoxazol-4-yl)benzo[d]thiazol-2-yl)azetidine-3-carboxamide (48)

LCMS ESI (m/z): $[M+H]^+$ calcd for $C_{17}H_{16}N_5O_2S^+$: 354.10.

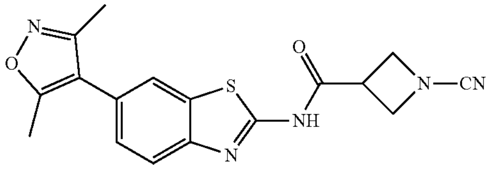 [SMILES: Cc1noc(C)c1-c1ccc2nc(NC(=O)C3CN(C#N)C3)sc2c1]

1-Cyano-N-(6-(3,5-dimethylisoxazol-4-yl)benzo[d]thiazol-2-yl)azetidine-3-carboxamide (47)

LCMS ESI (in a): 353.87: $[M+H]^+$ calcd for $C_{17}H_{16}N_5O_2S^+$: 354.10

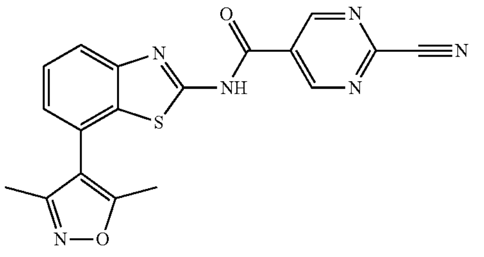 [SMILES: Cc1noc(C)c1-c1cccc2nc(NC(=O)c3cnc(C#N)nc3)sc12]

2-Cyano-N-(7-(3,5-dimethylisoxazol-4-yl)benzo[d]thiazol-2-yl)pyrimidine-5-carboxamide (45)

LCMS ESI (m/z): 376.87; $[M+H]^+$ calcd for $C_{18}H_{13}N_6O_2S^+$: 377.08

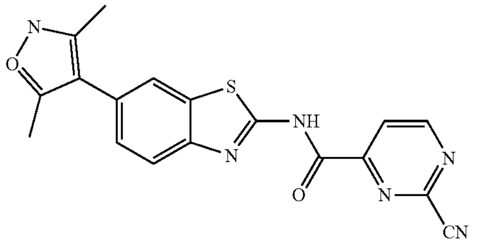

2-Cyano-N-(6-(3,5-dimethyl-1λ$^3$,2λ$^2$-isoxazol-4-yl)benzo[d]thiazol-2-yl)pyrimidine-4-carboxamide (43)

LCMS ESI (m/z): 376.87; $[M+H]^+$ calcd for $C_{18}H_{13}N_6O_2S^+$: 377.08

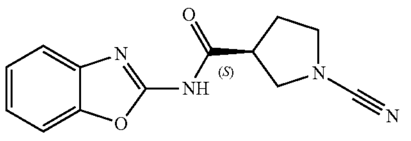

(S)—N-(benzo[d]oxazol-2-yl)-1-cyanopyrrolidine-3-carboxamide (39)

LCMS ESI (m/z): 256.97; $[M+H]^+$ calcd for $C_{13}H_{13}N_4O_2$: 257.10

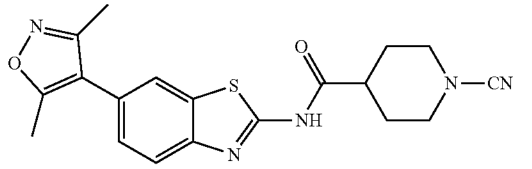 [SMILES: Cc1noc(C)c1-c1ccc2nc(NC(=O)C3CCN(C#N)CC3)sc2c1]

1-Cyano-N-(6-(3,5-dimethylisoxazol-4-yl)benzo[d]thiazol-2-yl)piperidine-4-carboxamide (35)

LCMS ESI (m/z):381.87; [M+H]+ calcd for $C_{19}H_{20}N_5O_2S^+$: 382.13

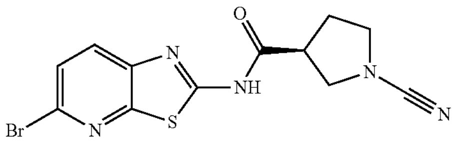 [SMILES: N#CN1CC[C@H](C(=O)Nc2nc3ccc(Br)nc3s2)C1]

(S)—N-(5-bromothiazolo[5,4-b]pyridin-2-yl)-1-cyanopyrrolidine-3-carboxamide (15)

LCMS ESI (m/z): 351.77; $[M+H]^+$ calcd for $C_{12}H_{11}BrN_5OS^+$: 351.99

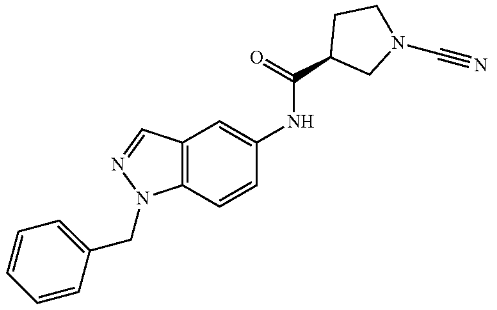 [SMILES: N#CN1CC[C@H](C(=O)Nc2ccc3c(cnn3Cc3ccccc3)c2)C1]

(S)—N-(1-benzyl-1H-indazol-5-yl)-1-cyanopyrrolidine-3-carboxamide (10)

LCMS ESI (m/z): 346.17; $[M+H]^+$ calcd for $C_{20}H_{20}N_5O^+$: 346.17

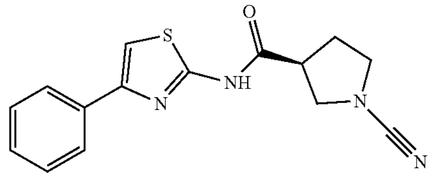 [SMILES: N#CN1CC[C@H](C(=O)Nc2nc(-c3ccccc3)cs2)C1]

(S)-1-cyano-N-(4-phenylthiazol-2-yl)pyrrolidine-3-carboxamide (11)

LCMS ESI (m/z): 298.97; [M+H]+ calcd for $C_{18}H_{15}N_4OS^+$: 299.10

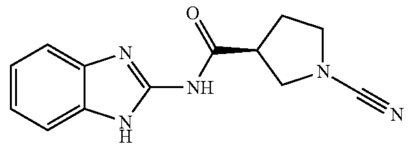 [SMILES: N#CN1CC[C@H](C(=O)Nc2nc3ccccc3[nH]2)C1]

(S)—N-(1H-benzo[d]imidazol-2-yl)-1-cyanopyrrolidine-3-carboxamide (30)

LCMS ESI (m/z): 256.17; $[M+H]^+$ calcd for $C_{13}H_{14}N_5O^+$: 256.12.

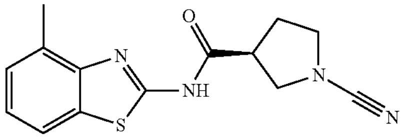 [SMILES: Cc1cccc2sc(NC(=O)[C@H]3CCN(C#N)C3)nc12]

(S)-1-cyano-N-(4-methylbenzo[d]thiazol-2-yl)pyrrolidine-3-carboxamide (18)

LCMS ESI (m/z): 287.07; $[M+H]^+$ calcd for $C_{14}H_{15}N_4OS^+$: 287.10

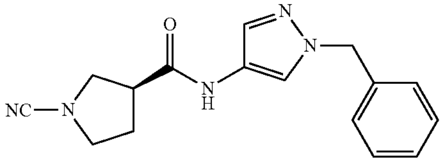 [SMILES: N#CN1CC[C@H](C(=O)Nc2cnn(Cc3ccccc3)c2)C1]

(S)—N-(1-benzyl-1H-pyrazol-4-yl)-1-cyanopyrrolidine-3-carboxamide (27)

LCMS ESI (m/z): 296.17; $[M+H]^+$ calcd for $C_{16}H_{18}N_5O^+$: 296.15

Figure 1B:
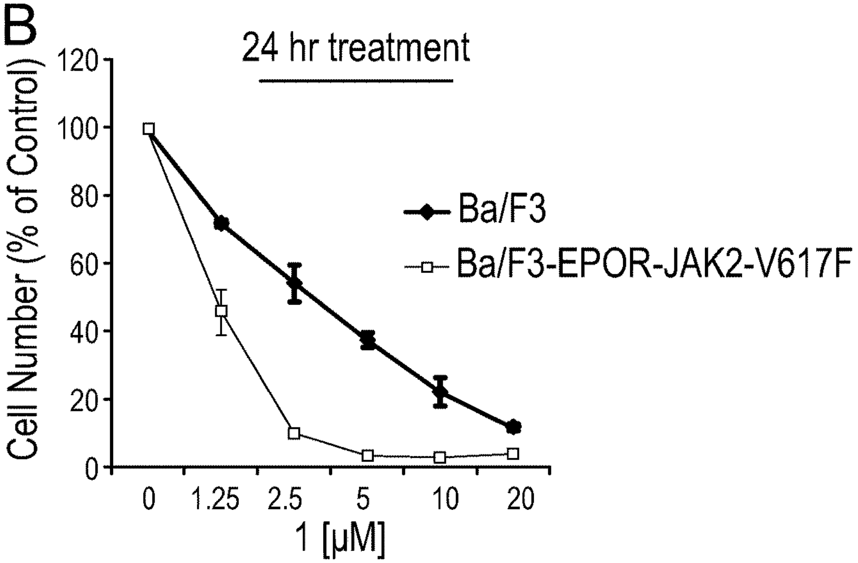
Figure 1C:
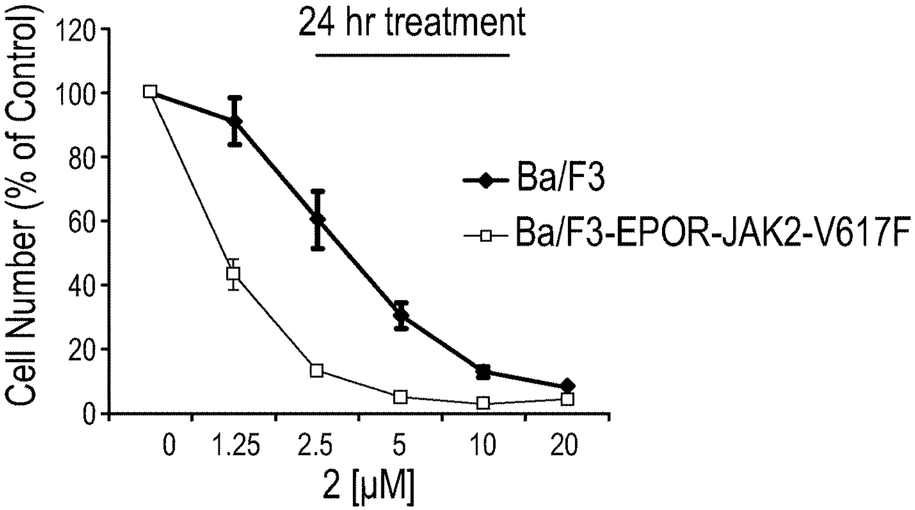
Figures 1D, 1E, 1F:
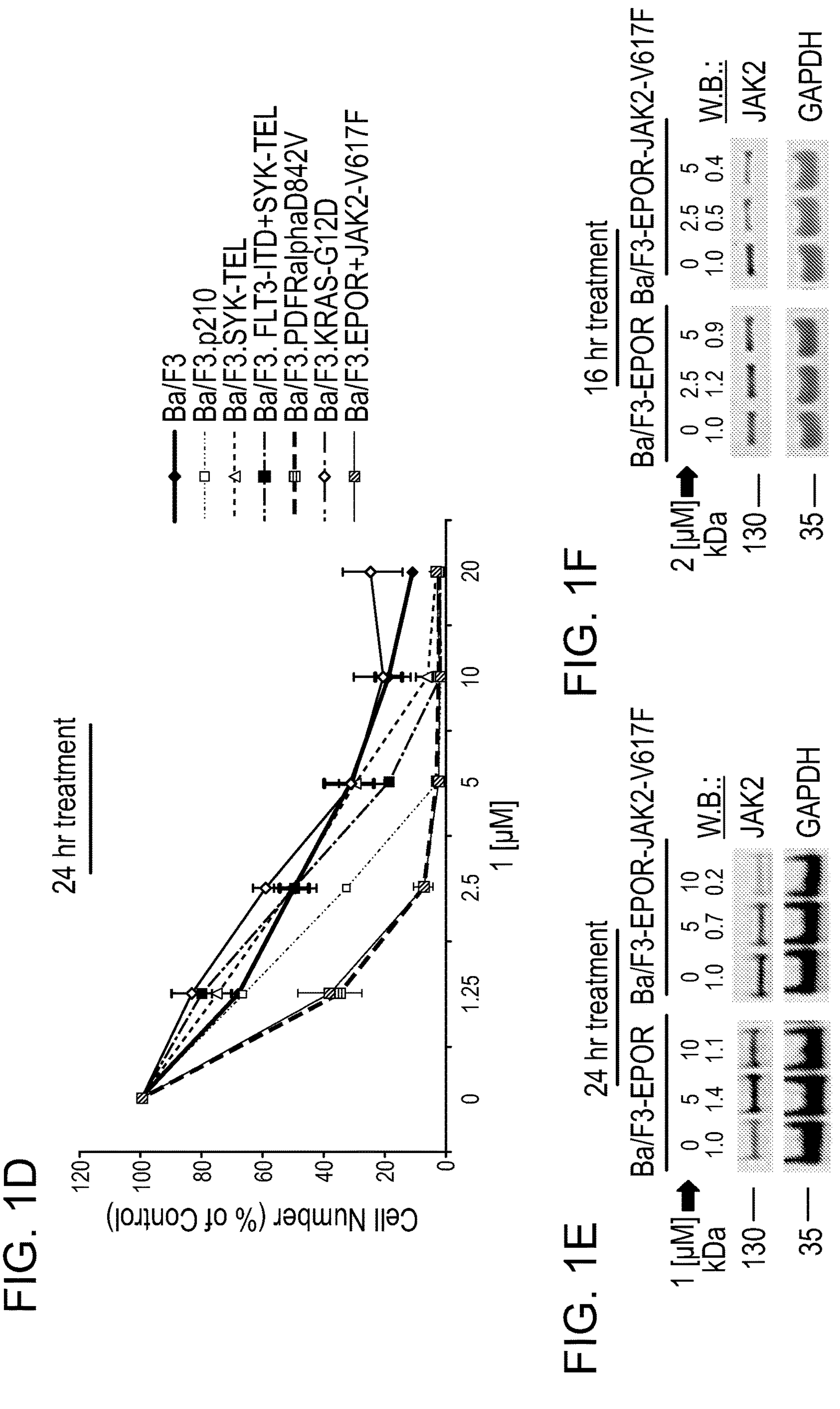

Example 18: Chemical Genetics Screen Identifies DUB Inhibitors that Lead to Selective Loss of JAK2-V617F Protein Over wt JAK2 Resulting in Growth Suppression As toxicities can result from small molecule targeting of both oncogenic mutated JAK2 as well as its non-mutated counterpart, a chemical genetics screen was designed and performed of a DUB-focused small molecule inhibitor library with the goal of leveraging crosstalk between phosphorylation and ubiquitination to identify DUB inhibitors able to selectively degrade mutant JAK2 while sparing wt JAK2. Of relevance, activated FLT3 can be selectively degraded over the wt enzyme by inhibition of the DUB, USP10, (Wernig, et al., 2008, Blood, 111(7):3751-9) and similar to FLT3, JAK2 is ubiquitinated in an activation-dependent manner. In brief, the library of known and novel DUB inhibitors was evaluated for ability to suppress growth of Ba/F3-EPOR-JAK2-V617F-expressing cells selectively over Ba/F3-EPOR cells growing in the presence of interleukin-3. Two structurally-related DUB inhibitors, compounds 1 and 2 (FIG. 1A), induced selective killing of Ba/F3-EPOR-JAK2-V617F-expressing cells, as compared to wt JAK2-expressing parental Ba/F3 cells (FIG. 1B-FIG. 1C). When compared to Ba/F3 cells engineered to overexpress other oncogenes, Ba/F3-EPOR-JAK2-V617F showed among the highest sensitivity to compound 1 (FIG. 1D). Consistent with the possibility that selective growth suppression resulted from selective degradation of the mutant enzyme, both compounds led to decreases in JAK2-V617F protein in Ba/F3-EPOR-JAK2-V617F-expressing cells while having little to no impact on JAK2 levels in Ba/F3-EPOR-JAK2 wt cells (FIG. 1E-FIG. 1F).

Figure 17A:
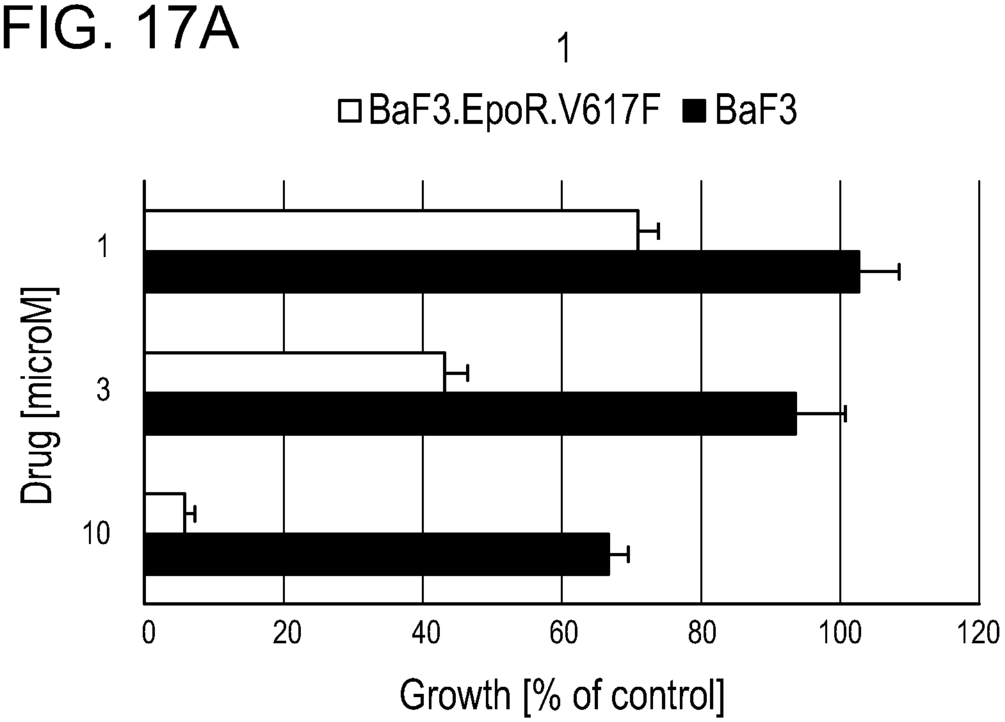
FIG. 17A-FIG. 17C is a series of bar plots and blots showing the effects of compounds 1 and 2 on cell growth.
Figure 17B:
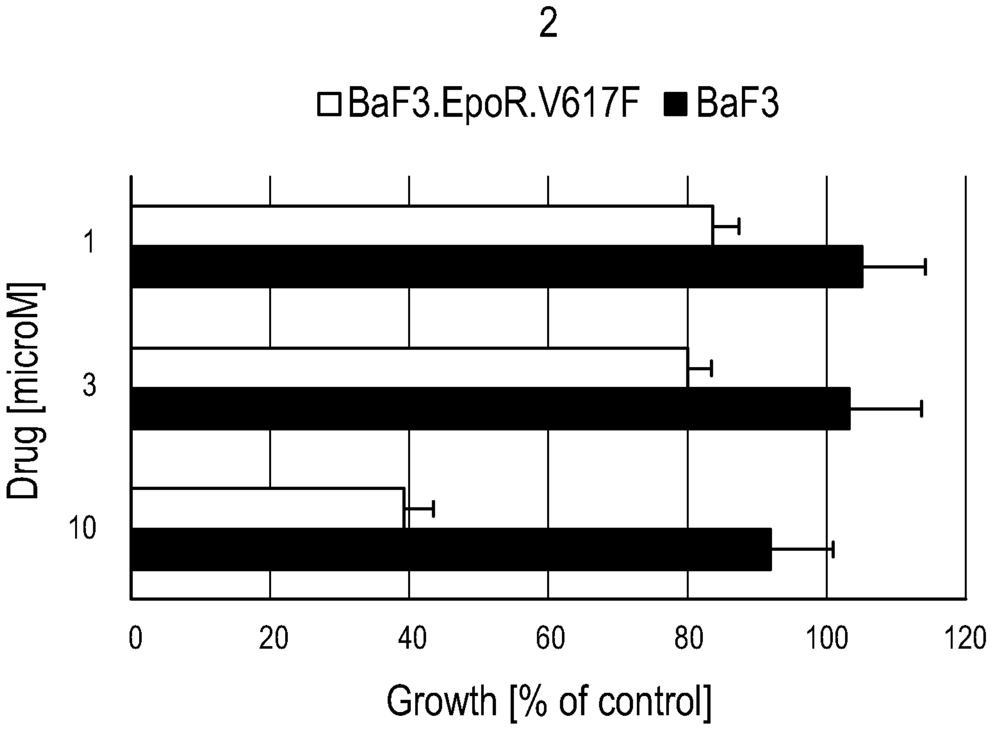
Figure 17C:
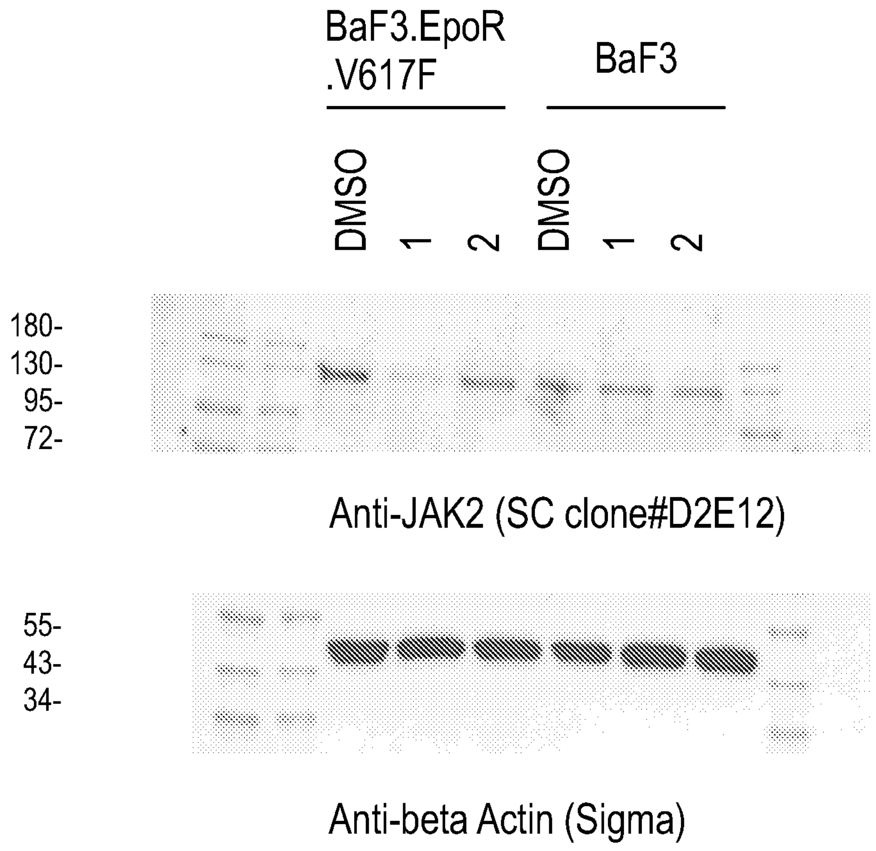
Figure 18A:
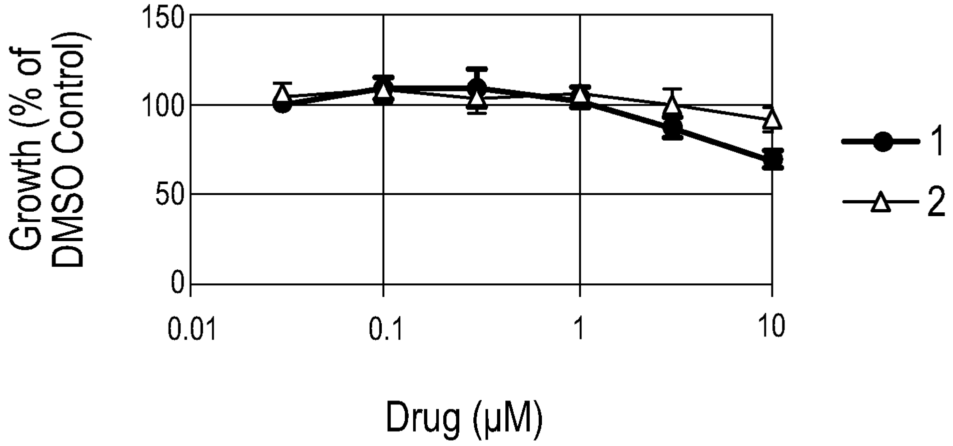
FIG. 18A-FIG. 18B is a series of line plots showing the effects of compound 1 or 2 on cell growth.
Figure 18B:
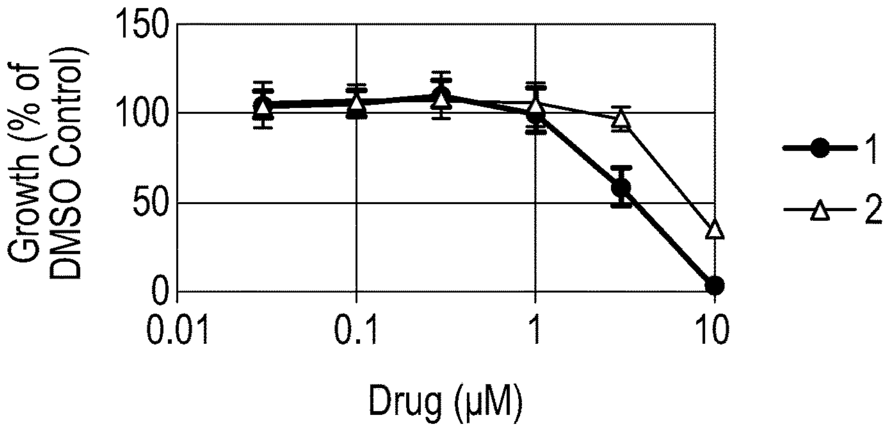

Additional, independent experiments of compounds 1 and 2 on Ba/F3-EPOR-JAK2-V617F-expressing cells and Ba/F3 parental cells confirmed the ability of both drugs to inhibit growth, particularly on Ba/F3-EPOR-JAK2-V617F-expressing cells (FIG. 17A-FIG. 17B). In addition, independent western blotting confirmed the degradation of JAK2 by compounds 1 and 2 (FIG. 17C). A broader range of compounds 1 and 2, including concentrations lower than 1 μM, were also tested on growth of EPOR-JAK2-V617F-expressing Ba/F3 cells and parental Ba/F3 EpoR+ cells (24 hours treatment on 4000 cells per well) (FIG. 18-FIG. 18B). Cell growth inhibition (FIG. 17A-FIG. 17B, FIG. 18A-FIG. 18B) was tested on Ba/F3-EPOR-JAK2-V617F (−IL-3/WEHI) and parental Ba/F3-EPOR cells (+IL-3/WEHI) plated at 2000 cells per well, at 1, 3 and 10 μM for 24 hours using the Promega CellTiter Glo® assay. Western blotting was performed after 18 hours of drug treatment of 10 μM of compound 1 or 5 μM of compound 2 in RIPA buffer.

Figure 19A:
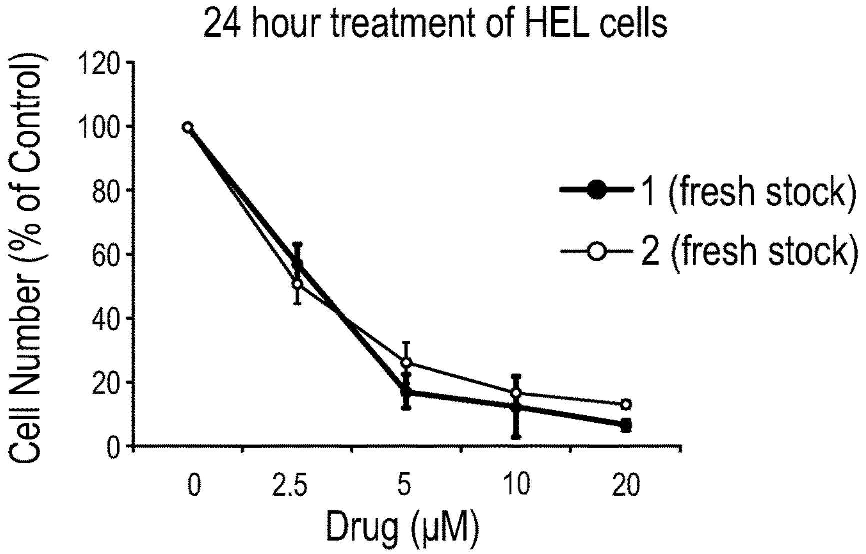
FIG. 19A-FIG. 19B is a series of line plots showing stability of compound 1 or 2 as measured by inhibition of cell growth.
Figure 19B:
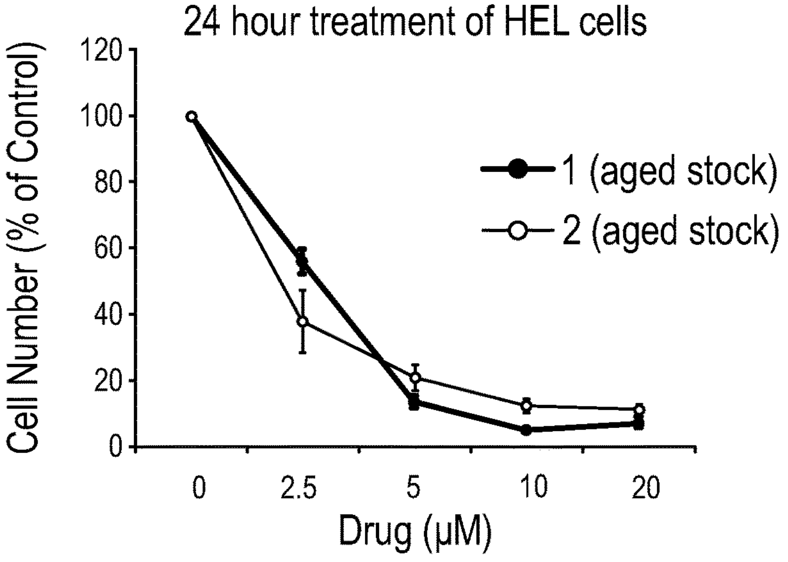

Furthermore, compounds 1 and 2 exhibit long term stability. Fresh or aged stocks of compounds 1 and 2 were tested for the ability to inhibit HEL cell growth at 2.5, 5, 10, and 20 μM of each drug after 24 hours (FIG. 19A-FIG. 19B). Aged stocks of both drugs showed comparable cell growth inhibition as compared to fresh stocks.

The CellTiter Glo® assay was performed using HEL cells seeded at 1000 cells/well of a 96-well plate. The “fresh” drug stocks were obtained frozen (stored at −20° Celsius) within days of executing the proliferation experiment for which results are shown. The “aged” drug stocks were obtained from freeze-thawed stocks serially diluted and stored at −20° Celsius in the laboratory. The “aged” stocks were stored between at least two years to three years at −20° Celsius with little to no freeze-thaw cycles prior to execution of the proliferation experiment for which results are shown. “Aged” stocks may be stored for several years (e.g., at least one year, at least two years, at least three years, at least four years or more) at −20° Celsius prior to use. These data illustrate that the compounds are stable for more than one year.

Figure 2A:
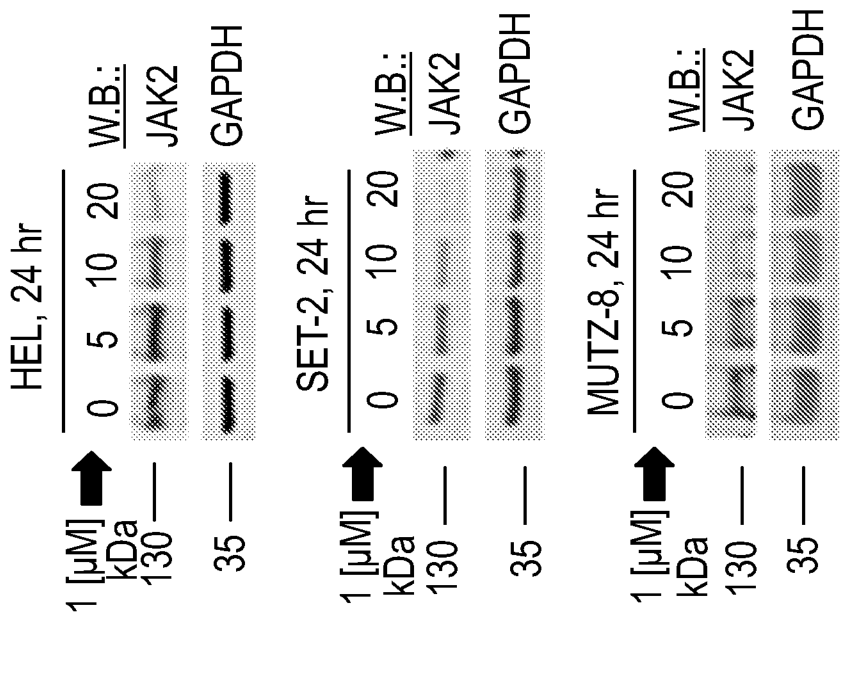
FIG. 2A-FIG. 2F is a series of blots and line graphs showing that compound 1 selectively degrades JAK2-V617F in human AML cells.
Figure 2B:
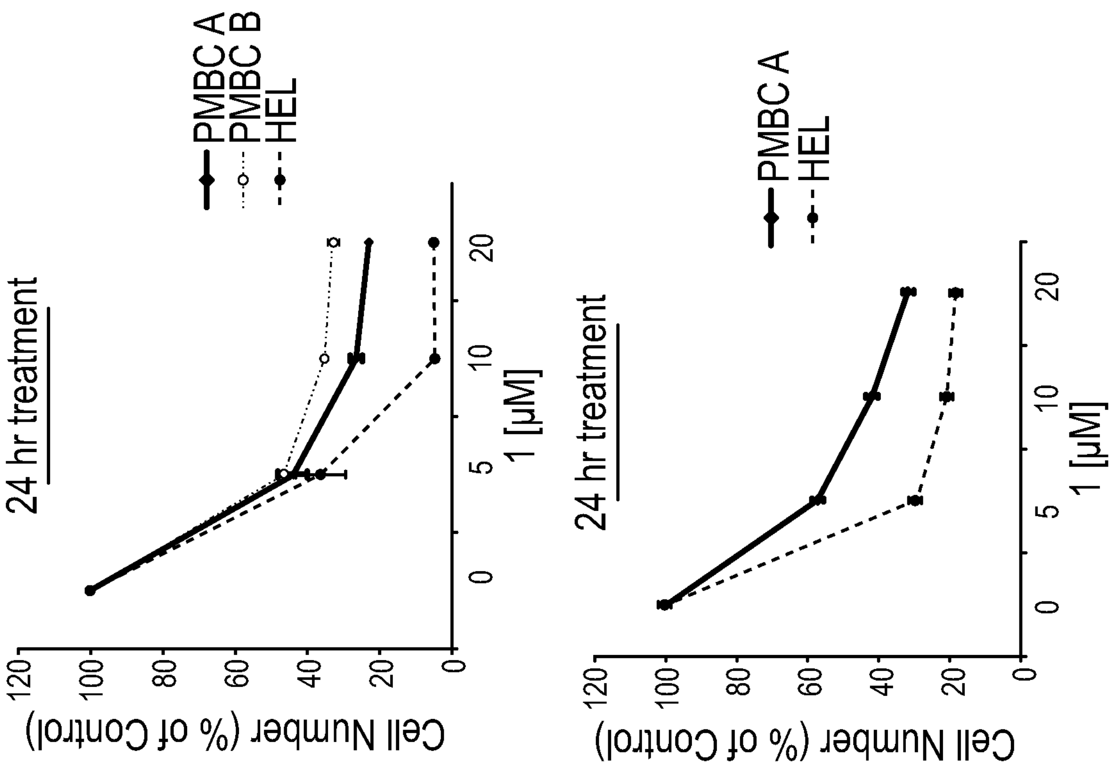
Figure 2D:
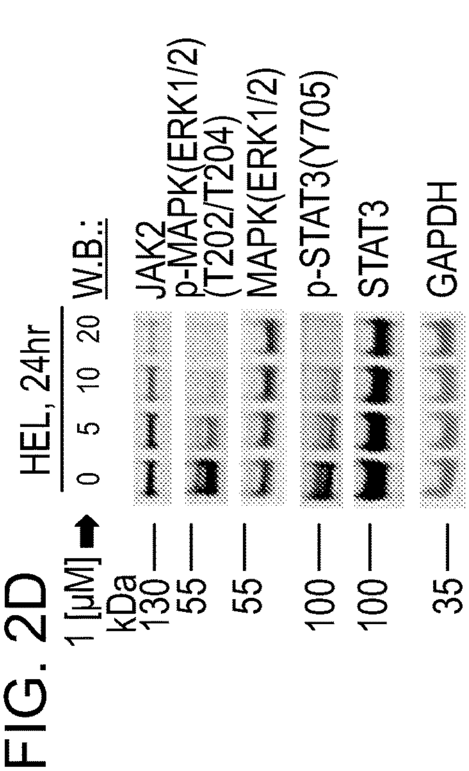
Figure 2F:
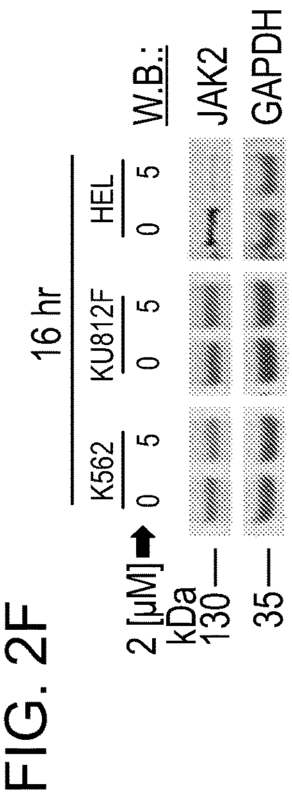
Figure 2C:
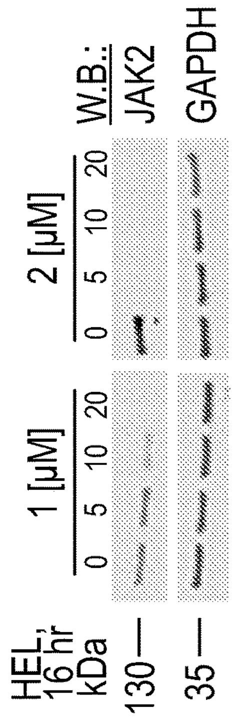
Figure 2E:
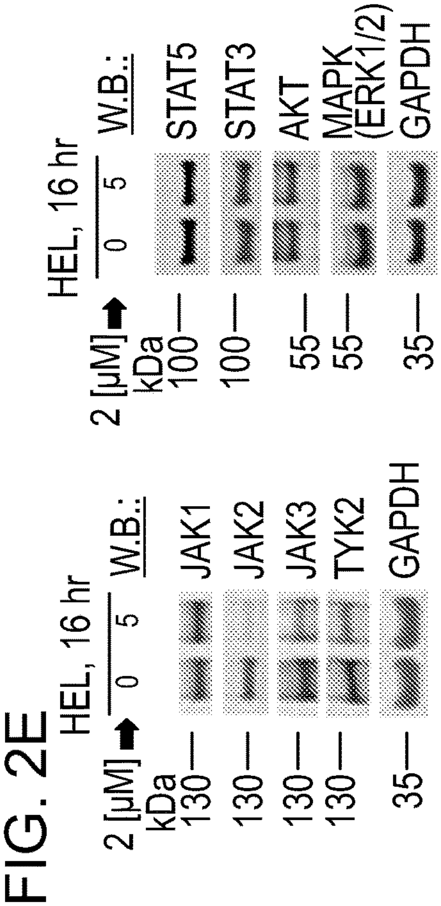
Figures 8A, 8B, 8C, 8D:
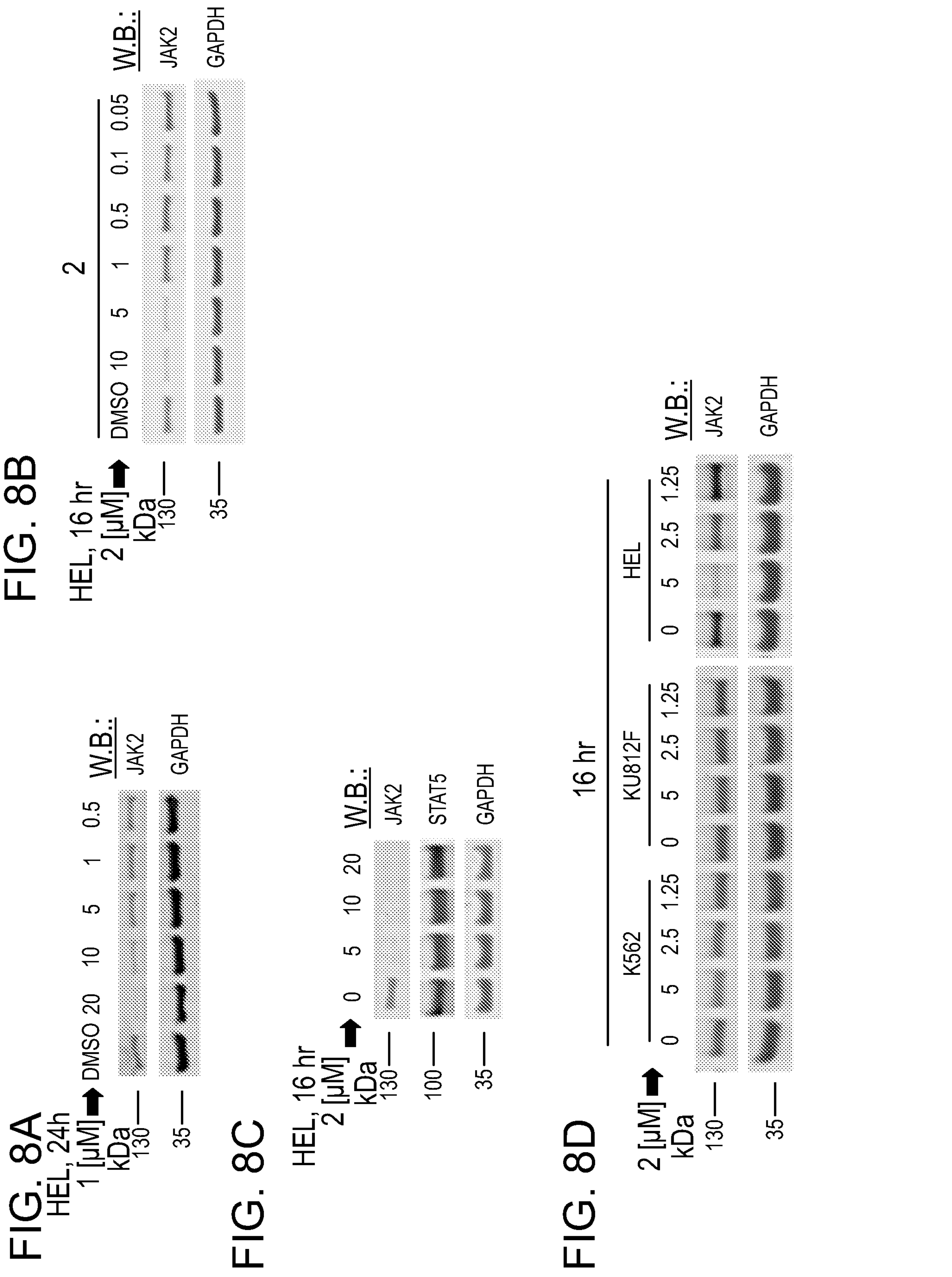
FIG. 8A-FIG. 8D is a series of blots showing the targeted effects of compound 1 and its potent analog compound 2.

The compound effects on JAK2-V617F-expressing cells were confirmed not to be unique to the Ba/F3 system. Treatment of JAK2-V617F-expressing human AML cell lines, HEL, SET-2 and MUTZ8, with the DUB inhibitors showed dose-dependent loss of JAK2 protein and selective inhibition of JAK2-V617F-positive cell growth over wt JAK2-expressing PBMCs, consistent with the Ba/F3 system (FIG. 2A-FIG. 2C, FIG. 8A-FIG. 8B). As expected, degradation of JAK2-V617F in HEL cells correlated with inhibition of JAK2 signaling including inhibition of phosphorylation of STAT3 and MAPK, however total STAT3, STAT5 and MAPK protein levels remained unchanged (FIG. 2D, FIG. 8C). Inhibitor treatment of HEL cells led to selective JAK2 loss with comparatively modest reduction of other JAK family members (JAK1, JAK3, and TYK2) (FIG. 2C, FIG. 2E, and FIG. 8B-FIG. 8C). As was observed in the Ba/F3 system, the effects were specific for mutant JAK2. DUB inhibitor treatment showed specificity for JAK2-V617F positive cells over wt JAK2-expressing leukemia cell lines, K562 and KU812F (FIG. 2F, FIG. 8D). Taken together, these results strongly support the selective induction of mutant JAK2 degradation by these DUB inhibitors.

Figure 3A:
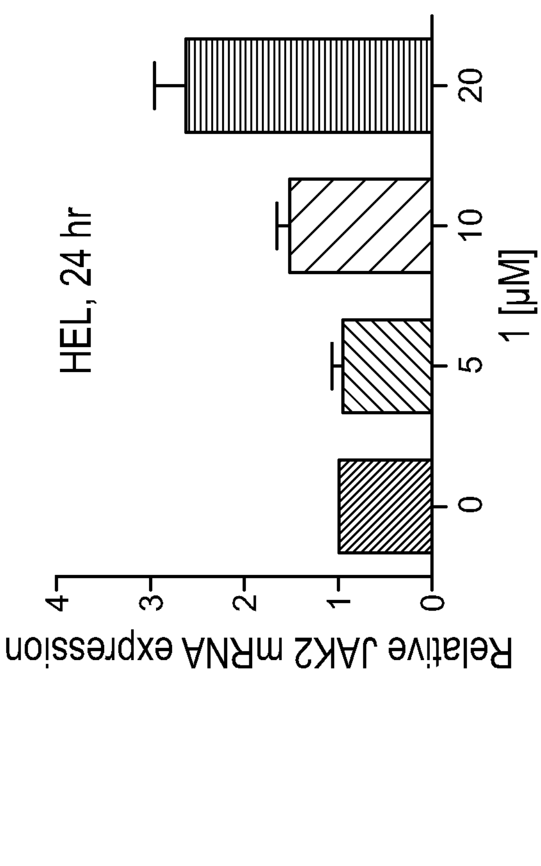
FIG. 3A-FIG. 3F is a bar graph, a series of blots, and a series of line graphs showing that compounds 1 and 2 promote ubiquitin-mediated proteasomal degradation of JAK2-V617F in human AML cells.
Figure 3B:
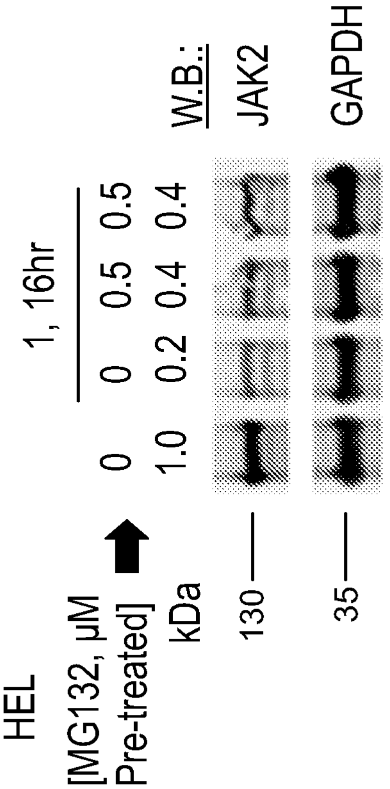
Figure 3C:
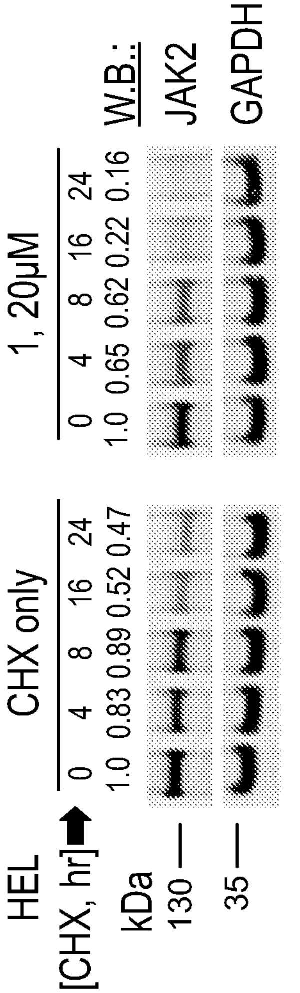
Figure 3D:
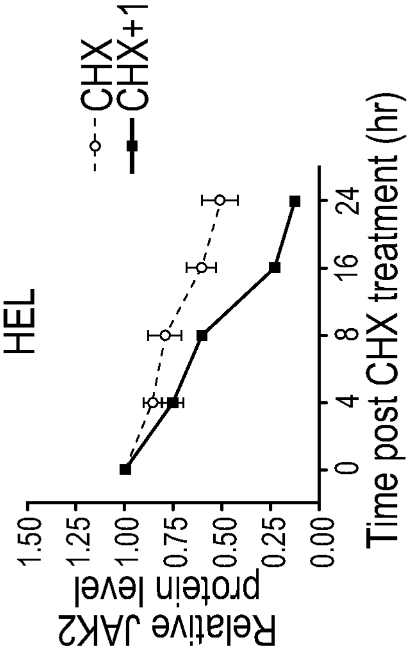
Figure 3E:
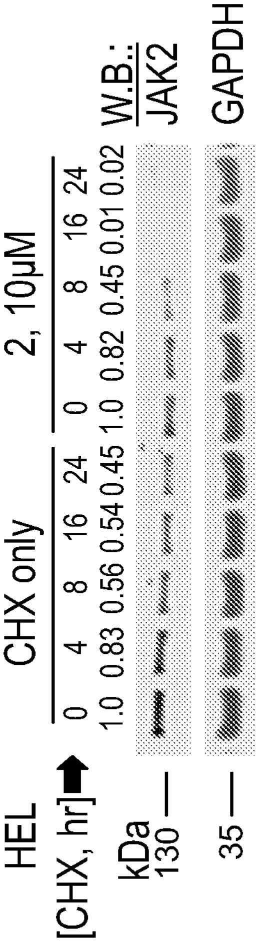
Figure 3F:
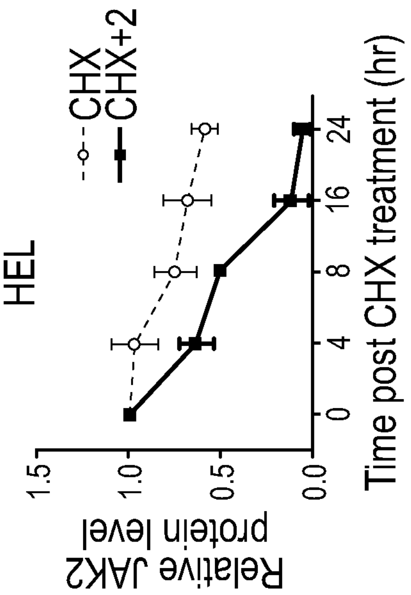
Figure 9A:
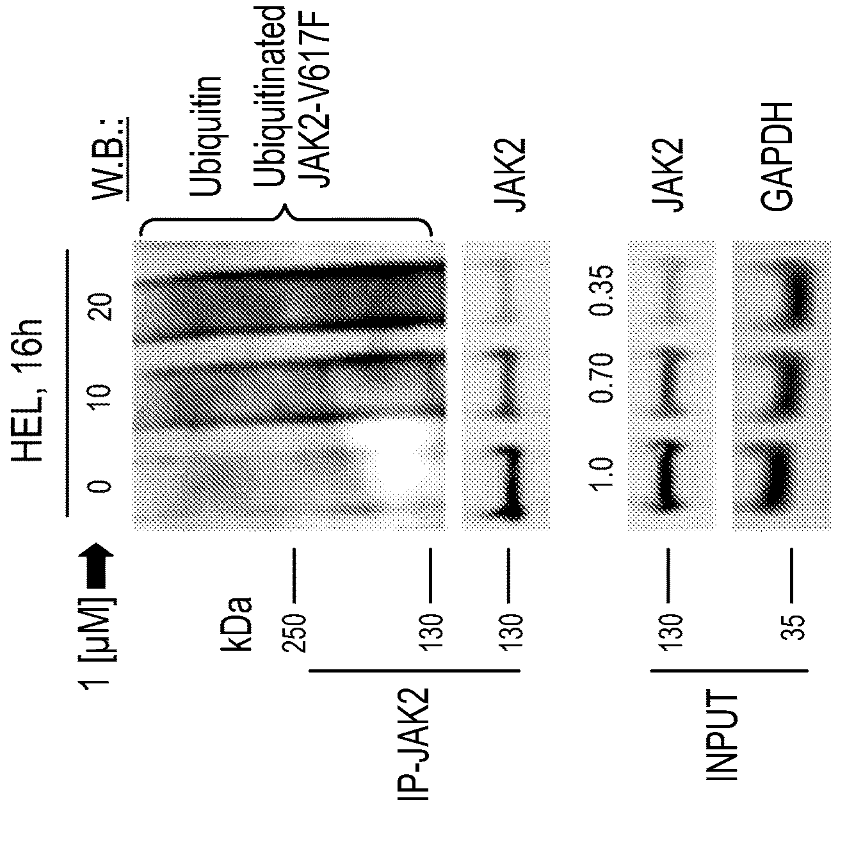
Figure 9B:
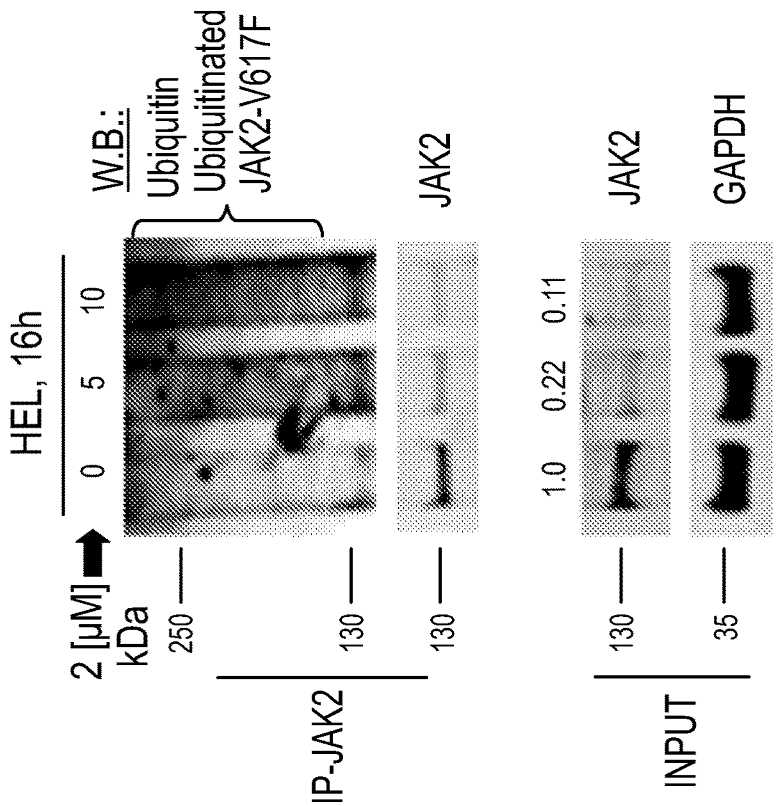

Example 19: Compounds 1 and 2 Promote Ubiquitin-Mediated Proteasomal Degradation of JAK2-V617F Protein loss occurred through ubiquitin-mediated proteasome degradation confirmed that the observed loss of mutant JAK2 protein likely resulted from DUB inhibition, and not an unknown activity of the compounds. First, the ubiquitination levels of mutant JAK2 in HEL cells was measured following compound 1 or 2 treatment. JAK2-V617F protein degradation correlated with JAK2 ubiquitination in response to compound 1 or 2 treatment (FIG. 9A-FIG. 9B). Real-time qPCR analysis confirmed that the inhibitor-induced reduction in JAK2 levels occurred at the protein level only with no decrease in gene transcription observed (FIG. 3A). Protein degradation was partially rescued by inhibition of the proteasome with MG132 (FIG. 9C-FIG. 9B), suggesting ubiquitin-mediated proteasomal degradation of JAK2-V617F. Both compounds were demonstrated to shorten JAK2-V617F protein half-life, as cycloheximide (CHX) and compound co-treatment of HEL cells revealed lower levels of JAK2-V617F as compared to CHX treatment alone (FIG. 3C-FIG. 3F). Consistent with these results, a drug-induced shortening of the protein half-life of JAK2-V617F but not wt JAK2 was observed in Ba/F3-derived cells (FIG. 9D and FIG. 9E). Taken together, these results suggest that compounds 1 and 2 degraded and selectively blocked the function of mutated JAK2 by promoting its ubiquitination.

Example 20: JOSD1 is Identified as a Novel Target of Compounds 1 and 2

To identify candidate DUBs that stabilize mutant JAK2, compounds 1 and 2 were comprehensively profiled against a panel of 41 purified DUBs and a panel of 60 native DUBs in cell lysates, which combined evaluated 72 DUBs (FIG. 4A). For purified enzyme profiling, the compounds were evaluated for biochemical inhibition of each DUB at a single concentration of 10 μM using DUB Profiler (Ubiquigent™). This approach confirmed UCHL1 as a target of the inhibitors and further identified USP30 and JOSD1 as potential additional targets (FIG. 4A). For profiling against native DUBs, competitive activity-based protein profiling was utilized (Altun, et al., 2011, Chemistry & Biology, 18(11):1401-12).

Figure 10A:
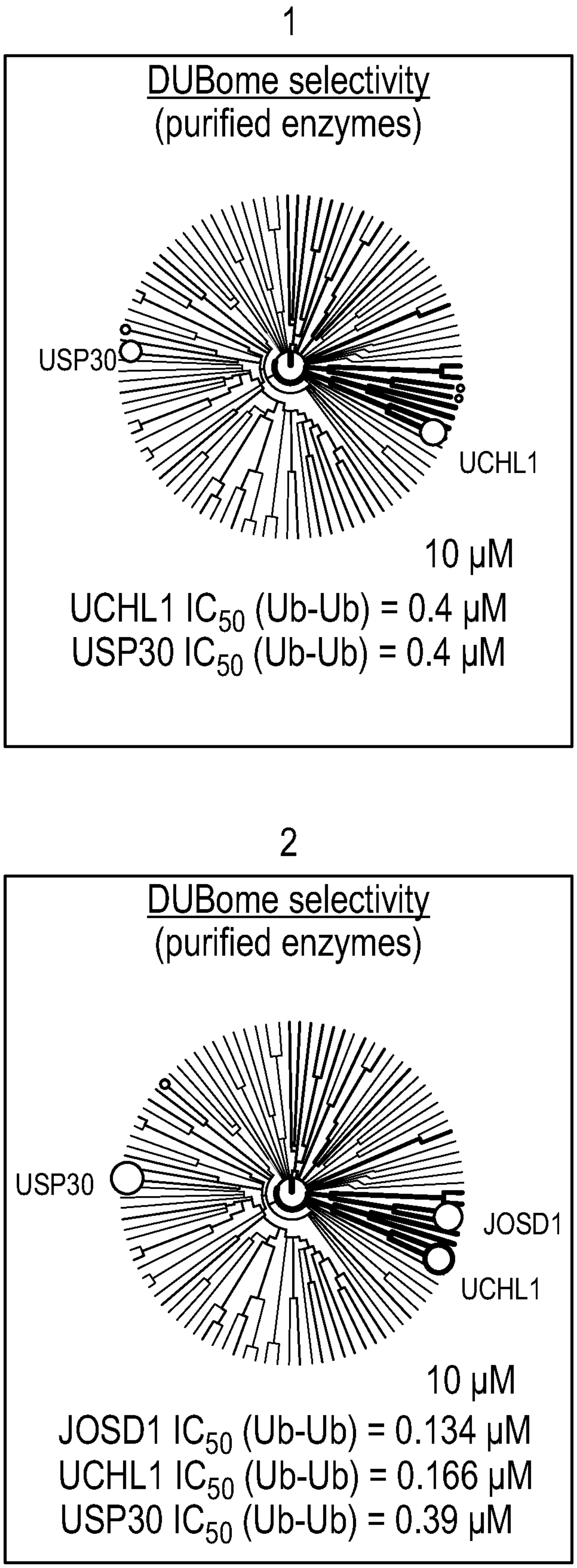
FIG. 10A-FIG. 10C is a profiling schematic, a profiling chart, and a series of line graphs showing that DUBome selectivity profiling of compounds 1 and 2.
Figure 10B:
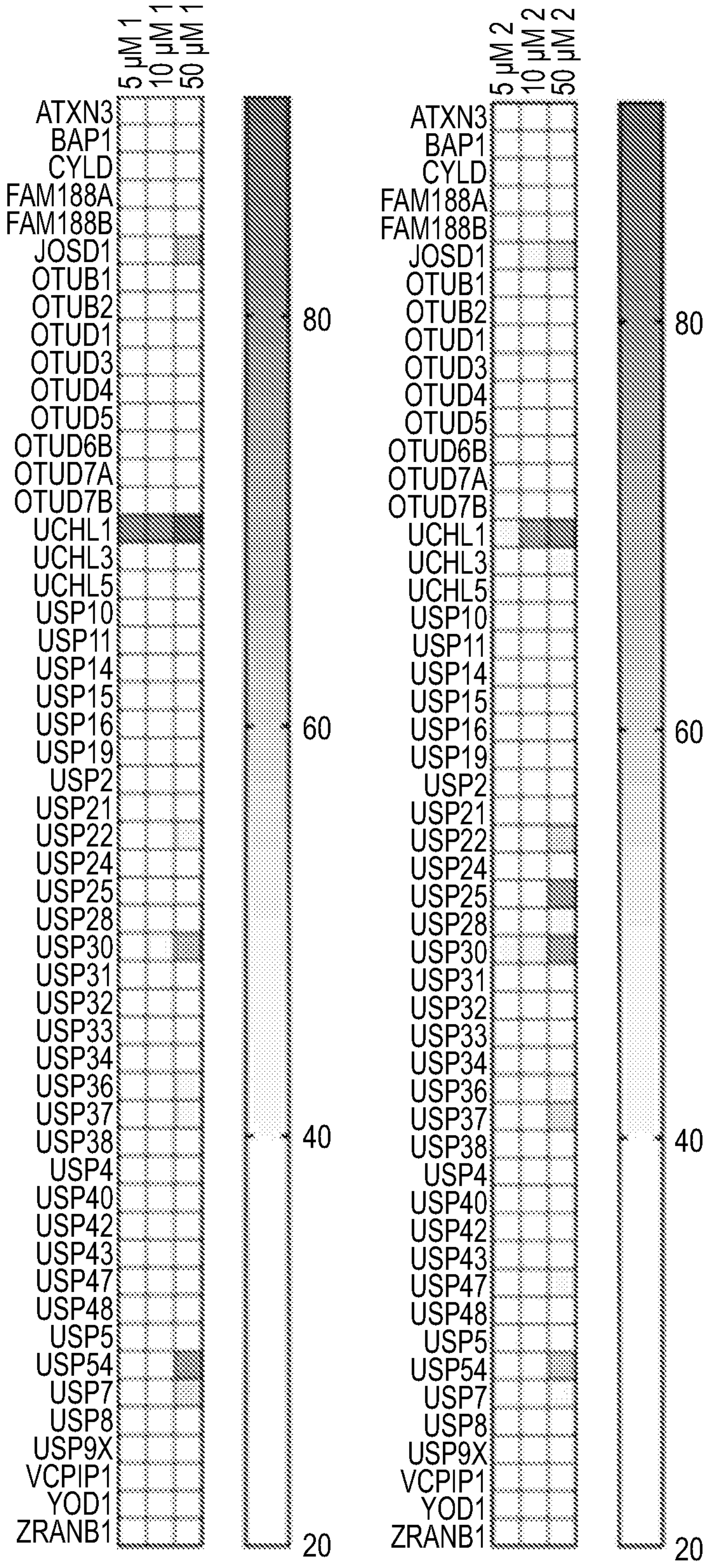
Figure 10C:
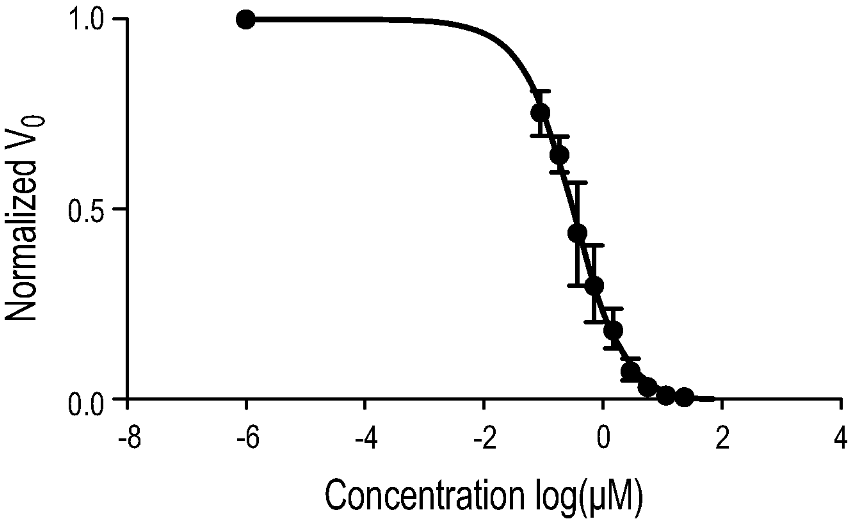
Figure 10C:
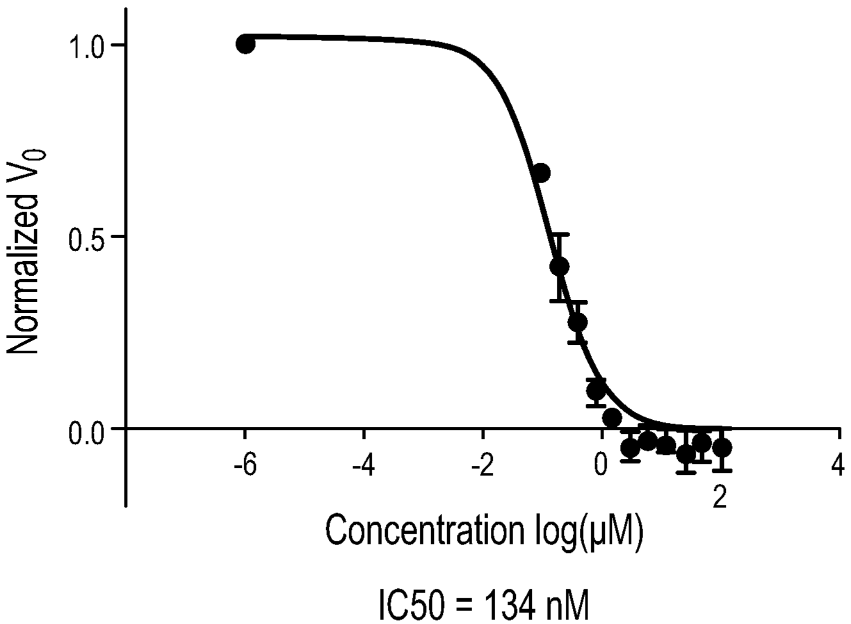

Specifically, quantitative mass spectrometry was utilized to measure the ability of compounds 1 and 2 to block labeling of 60 native DUBs by ubiquitin-based DUB activity-based probes in HEK-293T lysates. This analysis confirmed dose-dependent target engagement of UCHL1, USP30 and JOSD1 by both compounds (FIG. 4B and FIG. 10A-FIG. 10B). A small number of additional DUBs were inhibited at only the highest concentration tested (FIG. 10B). Biochemical $IC_{50}$ s were measured for the compounds against the three targets, which further confirmed inhibition of each target with potencies in the several hundred nM range (FIG. 4C and FIG. 10C).

Figures 11A, 11B, 11C:
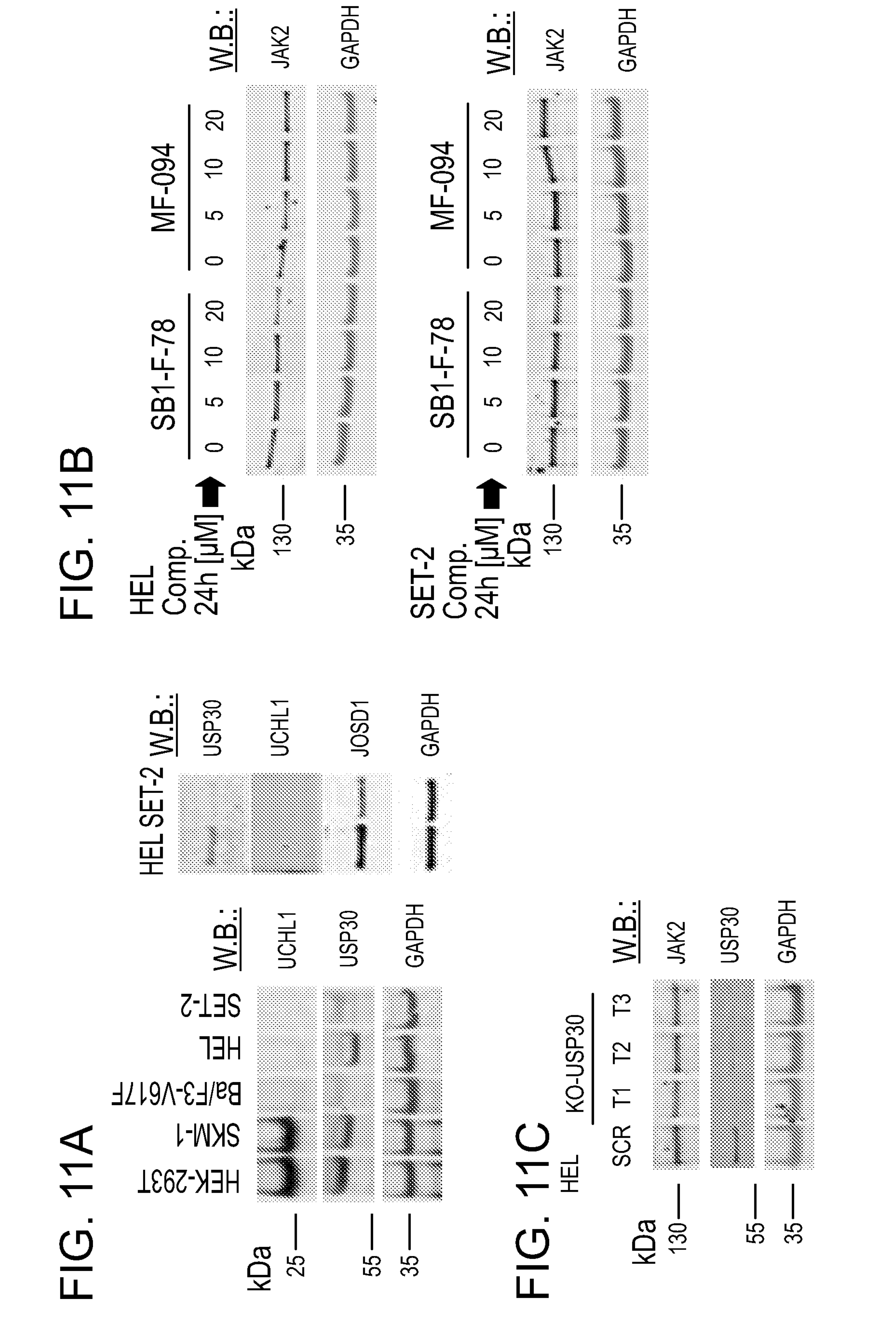
FIG. 11A is a series of blots showing that UCHL1, USP30 and JOSD1 expression levels were visualized in different cell lines by western blotting with indicated antibodies.
FIG. 11B is a western blot showing JAK2 protein levels following treatment with known USP30 inhibitors (SB1-F-78 and MF-094) in HEL and SET-2 cells.
FIG. 11C is a western blot showing the USP30 gene knock out in a HEL-GFP-CAS9 monoclonal cell line by USP30-silencing puromycin-resistant gRNAs (T1, T2 and T3) introduced by lentiviral transduction. Cells were collected after 3d puromycin selection and proteins detected by western blotting with the indicated antibodies.

As an initial assessment of whether UCHL1, USP30, or JOSD1 may be a relevant DUB target for loss of mutant JAK2, levels of the DUBs in HEL and SET2 cells were detected using western blot. UCHL1 was not observed to be expressed in JAK2-V617F-positive cell lines, USP30 was expressed in HEL cells however not in SET-2 cells, and JOSD1 expression was confirmed in both HEL and SET-2 cells (FIG. 11A). Based on the expression data, UCHL1 was ruled out as the DUB target of the inhibitors that stabilizes mutant JAK2. Due to availability of reagents, USP30 was first investigated using pharmacological and genetic inhibition. Little to no inhibitor-induced JAK2-V617F protein loss was observed in either HEL or SET-2 cells with the USP30 inhibitors MF-094 and SB1-F-78 (FIG. 11B) (Kluge, et al., 2018 Bioorg Med Chem Lett., 28(15):2655-59; International Patent Publication No. WO2017009650). In addition, knockout (KO) of USP30 in HEL cells did not lead to JAK2-V617F degradation (FIG. 11C). Taken together, these results suggest that neither UCHL1 nor USP30 stabilizes JAK2-V617F protein. The structures for USP30 inhibitors MF-094 and SB1-F-78 are shown below.

MF-094

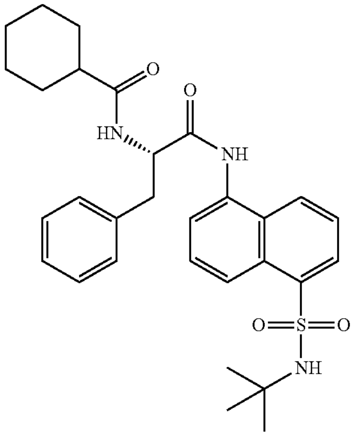

SB1-F-78

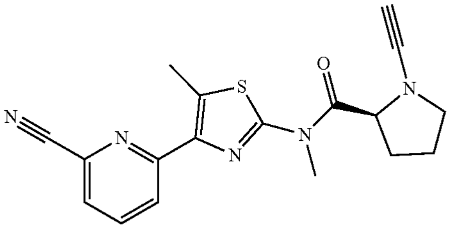

Figure 11E:
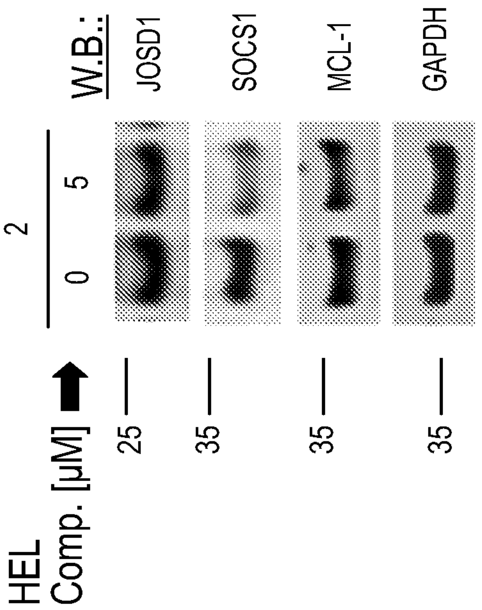
FIG. 11E is a series of blots showing that HEL cells were treated with compound 2 at 0 or 5 μM. JOSD1, SOCS1, MCL-1 and GAPDH were detected by western blotting with the indicated antibodies.
Figure 11D:
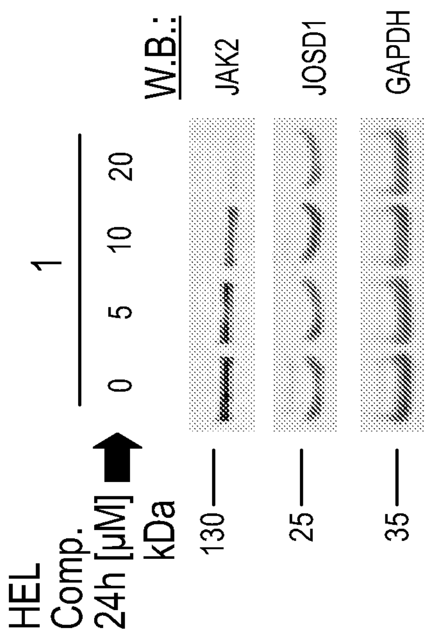
FIG. 11D is a series of blots showing that JAK2, JOSD1 and GAPDH protein levels were visualized after compound 1 treatment of HEL cells by western blotting.
Figure 11F:
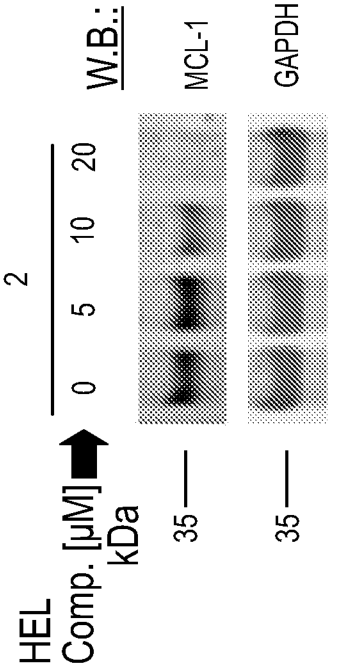
-FIG. 11F is a series of blots showing that UCHL1 and USP30 are unlikely candidates as DUB stabilizers of JAK2-V617F.

With JOSD1 as the prime candidate, JOSD1 binding and inhibition was evaluated by the compounds. First, targeted engagement was confirmed by showing competition with DUB ABP in HEL-FLAG-HA-JOSD1 cells following treatment with the two agents (FIG. 4D). The structures for negative control compounds 66 and 67 are shown below. In addition, the effects of small molecule inhibition of JOSD1 was investigated on MCL-1, an established substrate of JOSD1 (Wu, et al., 2020 Cell Death Differ., 27(1):55-70). It is important to note that treatment of JAK2-V617F-positive cells with a JOSD1-targeting inhibitor did not diminish JOSD1 protein levels (FIG. 11D): this suggests that drug treatment only impairs the enzyme activity of JOSD1. The expression of JOSD1, SOCS1 and MCL-1 were measured in HEL cells treated with 5 μM of compound 2. SOCS1 was observed to decrease after compound 2 treatment (FIG. 11E). The expression of MCL-1, which has been reported to be regulated by JOSD1 (Wang, et al., 2017 Viral Immunology, 30(5):342-49; Wu, et al., 2020 Cell Death & Differentiation, 27(1):55-70) was measured in HEL cells treated with compound 2. MCL-1 was observed to decrease at 10-20 μM drug concentrations (FIG. 11F), supporting the notion that JOSD1 is a DUB target of compound 2. Other exemplary compounds that inhibit DUBs are listed below in Table 3 (See Supra, ¶ [0063] for structures)

(66)

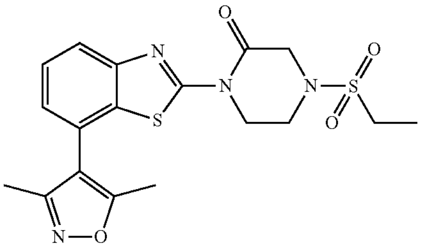

(67)

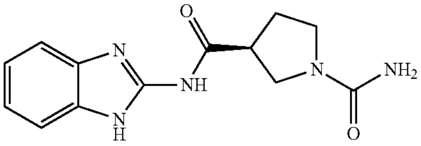

TABLE 3

| Compound # | UCHL1 $IC_{50}$ (μM) | JOSD1 $IC_{50}$ (μM) |
|---|---|---|
| 3 | | 0.028 |
| 4 | | 0.045 |
| 5 | | 0.074 |
| 6 | | 0.082 |
| 7 | | 0.095 |
| 8 | 0.012 | 0.099 |
| 9 | | 0.15 |
| 2 | | 0.16 |
| 10 | | 0.16 |
| 11 | | 0.16 |
| 12 | 0.1 | 0.244 |
| 13 | | 0.26 |
| 14 | | 0.27 |
| 15 | 2 | 0.288 |
| 16 | | 0.305 |
| 17 | | 0.37 |
| 18 | | 0.38 |
| 19 | 0.09 | 0.42 |
| 20 | 2.06 | 0.43 |
| 21 | | 0.46 |
| 22 | | 0.52 |
| 23 | 0.073 | 0.66 |
| 24 | 1.846 | 0.6896 |
| 25 | 8.9 | 0.9307 |
| 26 | 0.1 | 1.098 |
| 27 | | 1.099 |
| 28 | 0.155 | 1.221 |
| 29 | 2.002 | 1.241 |
| 30 | 3.67 | 1.374 |
| 31 | 2.689 | 1.4 |
| 32 | 0.104 | 1.475 |
| 33 | 1.83 | 1.95 |
| 34 | | 2.13 |
| 35 | 0.42 | 2.77 |
| 36 | 1.335 | 3.37 |
| 37 | | 3.96 |
| 38 | 0.089 | 4.15 |
| 39 | | 4.85 |
| 40 | 100 | 5.68 |
| 41 | 100 | 6.07 |
| 42 | 1.078 | 6.226 |
| 43 | | 6.42 |
| 44 | | 8.25 |
| 45 | | 11.15 |
| 46 | 100 | 11.27 |
| 47 | 1.29 | 13.22 |
| 48 | | 16.35 |
| 49 | | 20.28 |

$IC_{50}$ (μM) for identified DUB inhibitors.

TABLE 3-continued

| Compound # | UCHL1 $IC_{50}$ (μM) | JOSD1 $IC_{50}$ (μM) |
|---|---|---|
| 50 | 12.130 | 21.28 |
| 51 | | 22.95 |

$IC_{50}$ (μM) for identified DUB inhibitors.

JOSD1 biochemical inhibition was investigated for the analogs shown using the fluorescent substrate ubiquitin-rhodamine against purified enzyme in a continuous kinetic assay. In this assay, compounds listed were able to inhibit ubiquitin hydrolase activity of JOSD1 and UCHL1, with biochemical $IC_{50}$ s as shown. This confirmed compounds 1 and 2 compounds to be potent inhibitors of JOSD1 with $IC_{50}$ s in the several hundred nM range. The data illustrate that JOSD1 inhibition was improved and abolished with structural changes to the basic scaffold, further supporting the identified compounds to be bona fide inhibitors of JOSD1.

Example 21: JOSD1 Interacts with, Deubiquitinates, and Stabilizes JAK2-V617F

Figures 5A, 5B, 5C, 5D, 5E:
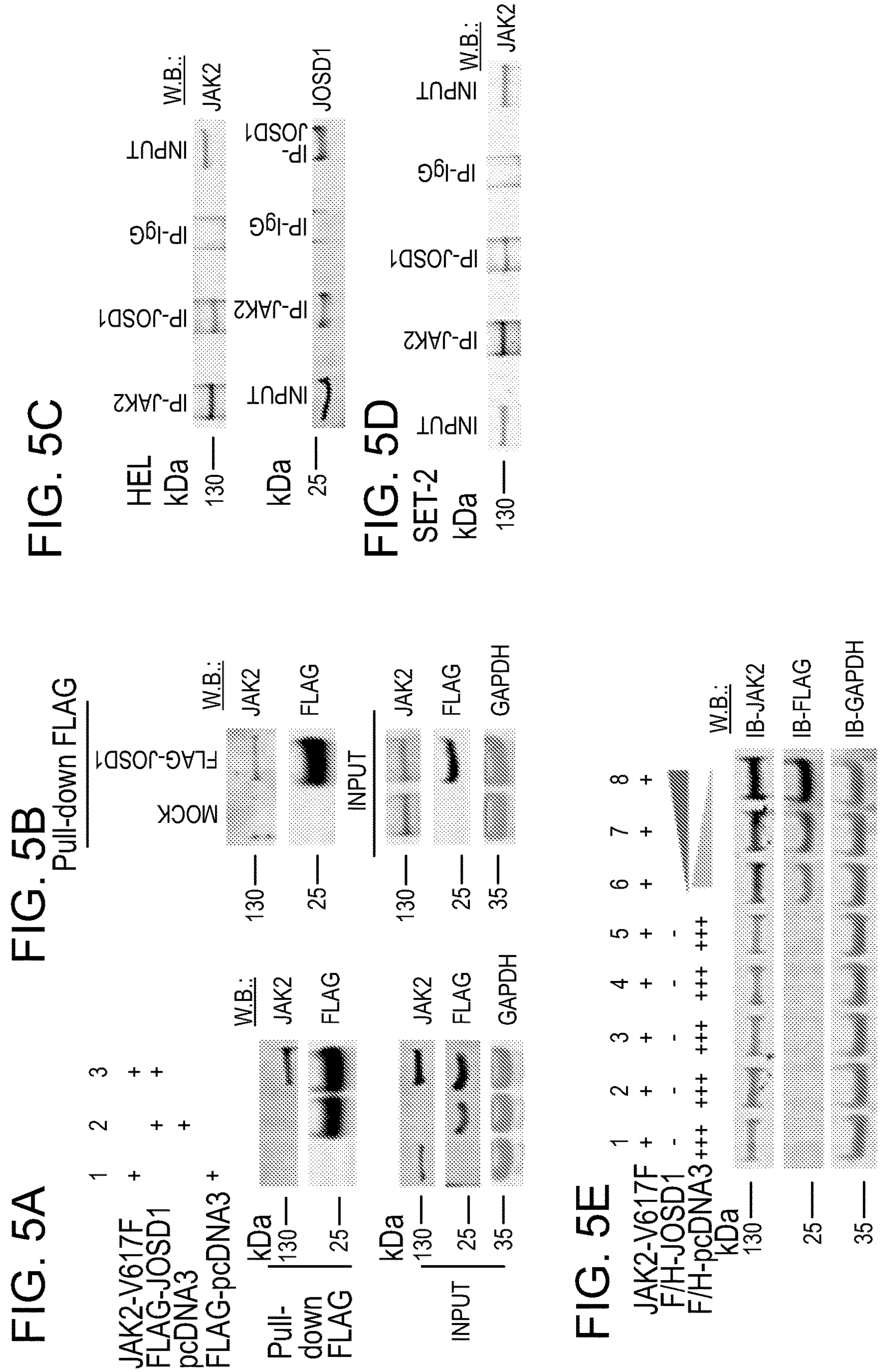
FIG. 5A-FIG. 5E is a series of blots showing that JOSD1 interacts with and stabilizes JAK2-V617F.
Figure 12A:
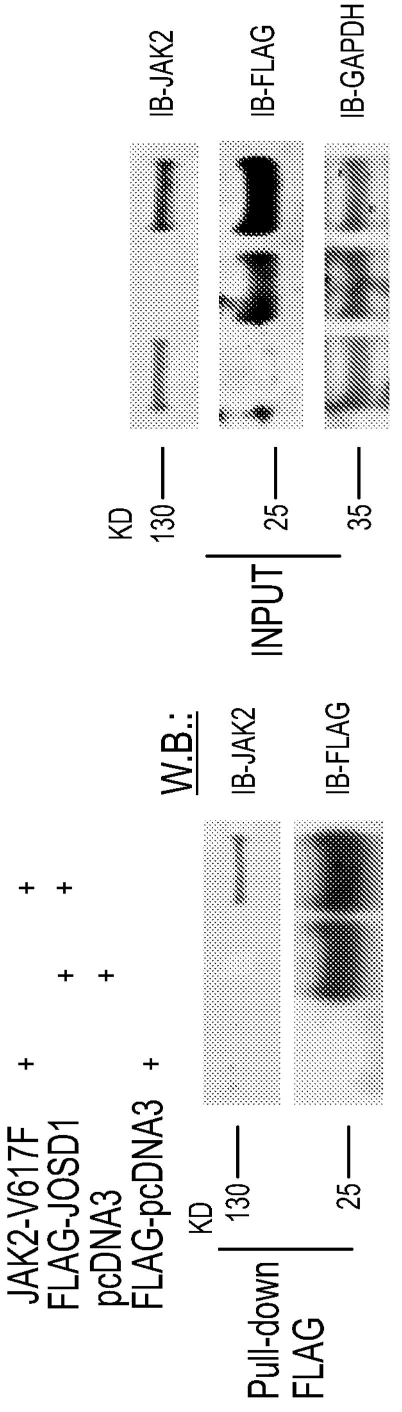
FIG. 12A-FIG. 12C is a series of blots showing that JOSD1 interacts with JAK2-V617F.
Figure 12B:
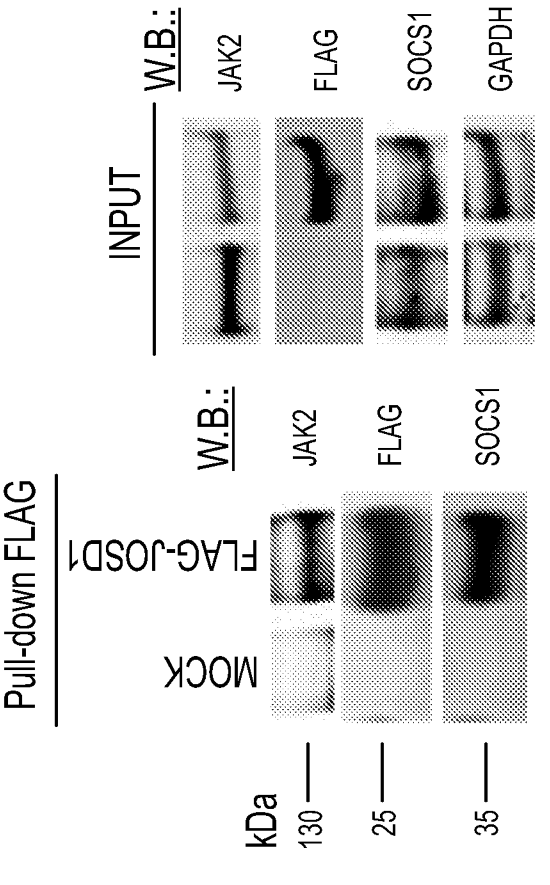
Figure 12C:
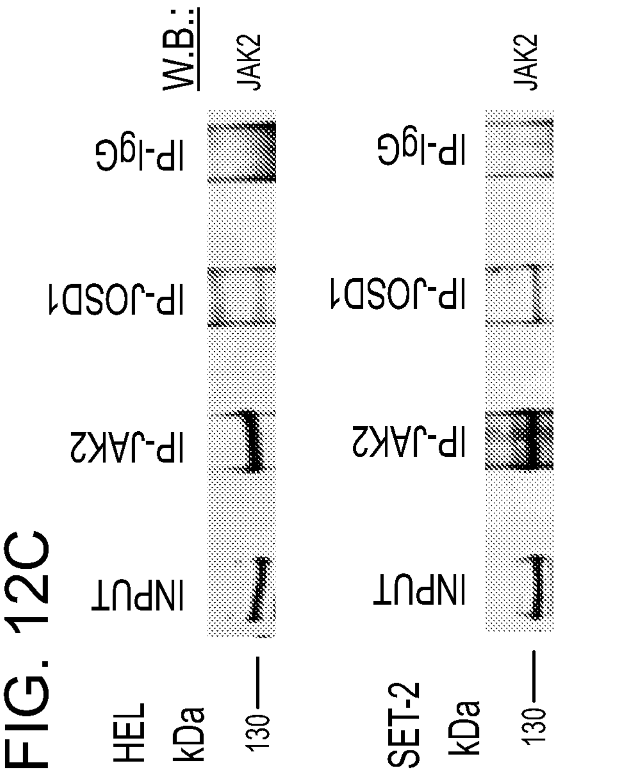

Next, it was investigated whether JOSD1 was involved in regulation of JAK2-V617F stability. First, to address whether there is direct physical association between JOSD1 and JAK2, immunoprecipitation (IP) of JOSD1 with JAK2 was performed in HEK-293T and FLAG/HA-JOSD1-expressing HEL cells. In both systems, robust interaction was observed between JAK2 and JOSD1 in cells engineered to exogenously express JOSD1 (FIG. 5A-FIG. 5B, FIG. 12A-FIG. 12B). In addition, reverse co-IP studies in human AML cells (HEL and SET-2) confirmed the association of endogenous JAK2-V617F with JOSD1 (FIG. 5C-FIG. 5D, FIG. 12C). Next, an overexpression assay was performed with HEK-293T cells and observed robust dose-dependent stabilization of JAK2-V617F with exogenous expression of JOSD1 was observed, as compared to an empty vector control (FIG. 5E).

Example 22: JOSD1 Depletion Selectively Degrades JAK2-V617F Over wt JAK2

Figure 6A:
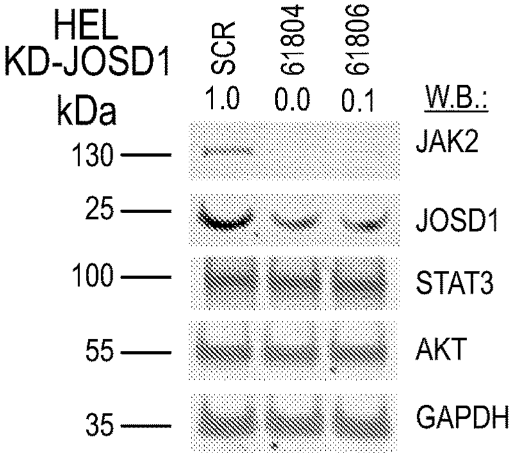
FIG. 6A-FIG. 6H is a series of blots and a bar graph showing the genetic depletion of JOSD1 selectively degrades JAK2-V617F over wild type (wt) JAK2.
Figure 6B:
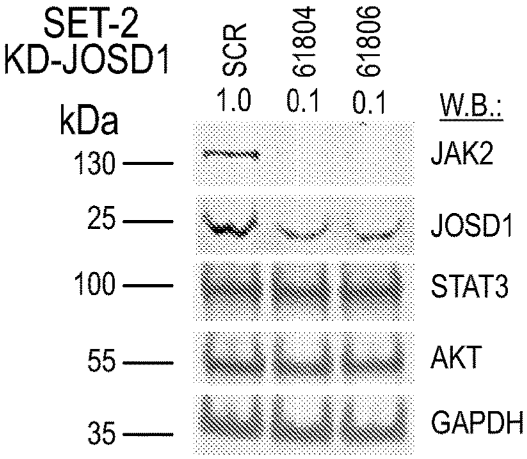
Figure 6C:
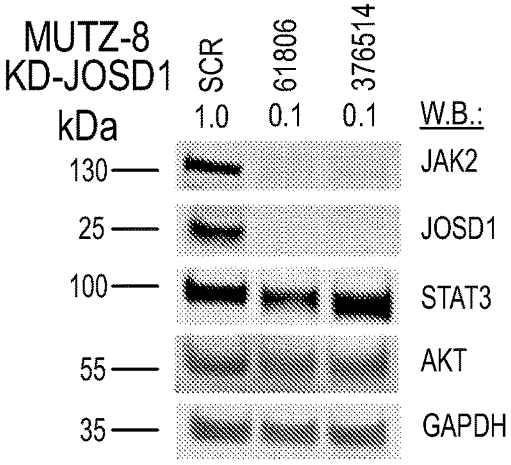
Figure 6D:
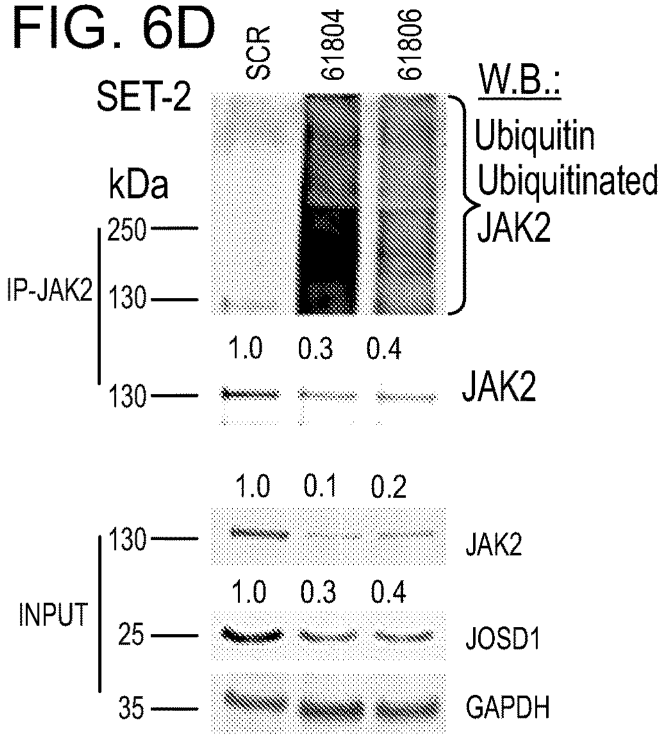
Figures 13A, 13B, 13C, 13D, 13E:
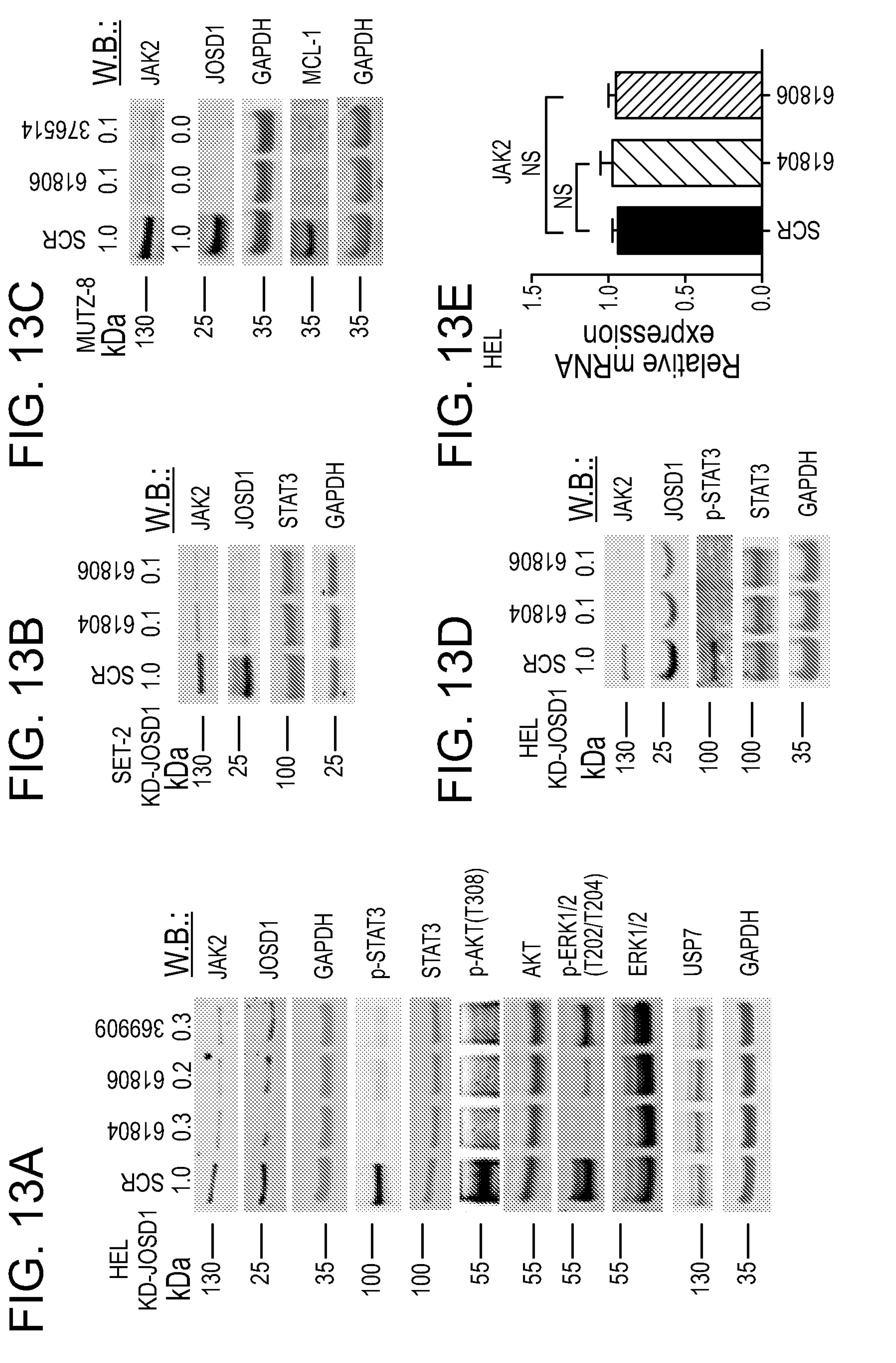
FIG. 13A-FIG. 13E is a series of blots showing depletion of JOSD1 by KD leads to targeted degradation of JAK2-V617F.

Genetic depletion studies were then performed using shRNA and CRISPR/Cas9. JOSD1 knock down (KD) was carried out with different shRNA hairpins targeting JOSD1 in HEL, SET-2 and MUTZ-8 cells. Using western blot, significant decreases were observed in JAK2-V617F protein and downstream signaling in JOSD1 KD cells as compared to SCR controls, with little to no impact on the expression of molecules downstream of JAK2, including STAT3, AKT and MAPK (FIG. 6A-FIG. 6C, FIG. 13A-FIG. 13D). In addition, protein levels of MCL-1 were also strongly decreased, consistent with previous literature identifying MCL-1 as a substrate (FIG. 13C). Consistent with the drug-induced loss of JAK2-V617F protein resulting from ubiquitin-dependent degradation following JOSD1 inactivation (FIG. 9A-FIG. 9B), JAK2-V617F ubiquitination was observed following JOSD1 KD (FIG. 6D). Specifically, JOSD1 KD with each hairpin resulted in the robust increase of poly-ubiquitination levels, as well as substantial degradation of JAK2-V617F, as compared to the scrambled control hairpin (FIG. 6D). These results strongly support the notion that JOSD1 stabilizes JAK2-V617F by interacting with and deubiquitinating it. As with ubiquitin-mediated degradation, there was no apparent decrease in JAK2 mRNA levels following KD (FIG. 13E).

Figure 6E:
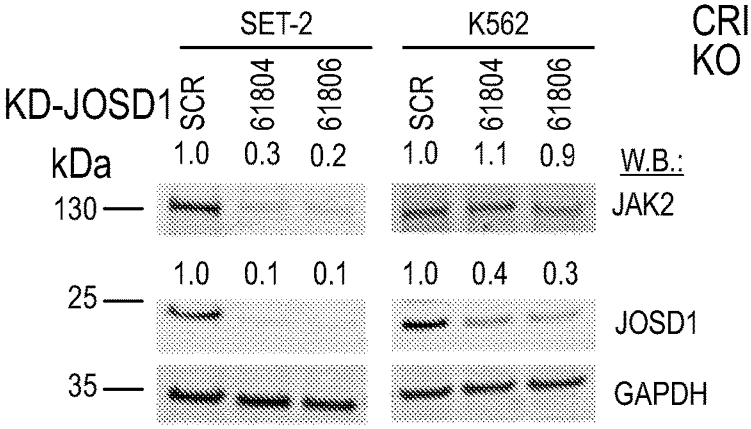

Next, the extent to which JOSD1 selectively stabilizes mutant JAK2 as opposed to wt JAK2 and other downstream markers was investigated via genetic KD and KO. JOSD1 KD was performed in wt JAK2-expressing K562 leukemia cells. Loss of JOSD1 protein was observed in these KD cells, however, there was no apparent decrease of wt JAK2 protein levels (FIG. 6E).

Figure 6F:
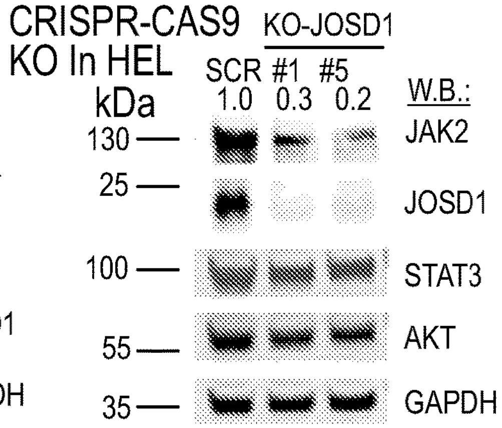
Figure 6G:
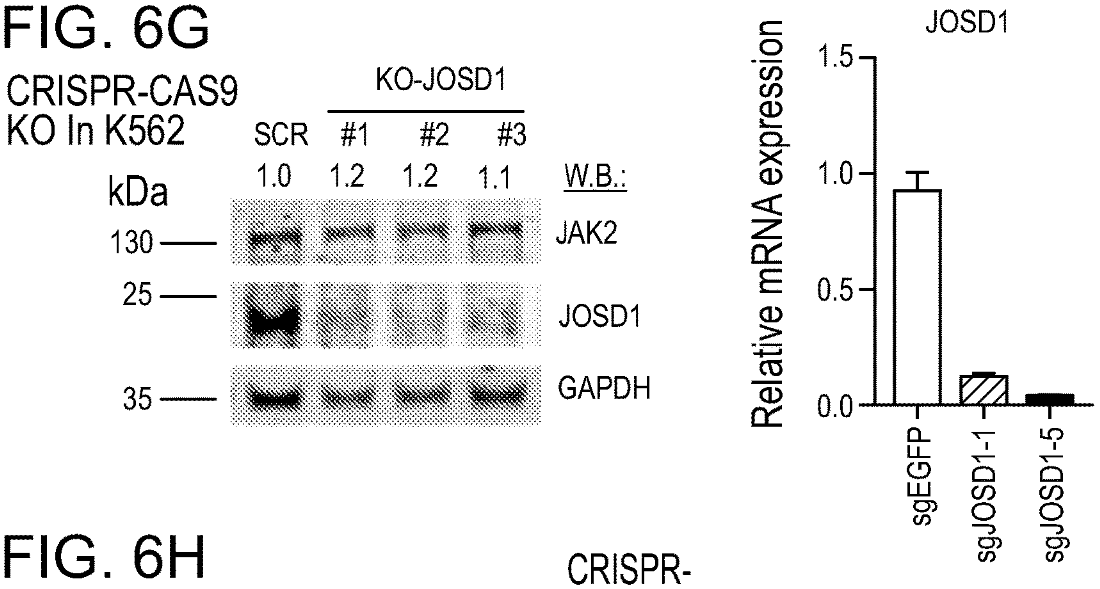
Figure 6H:
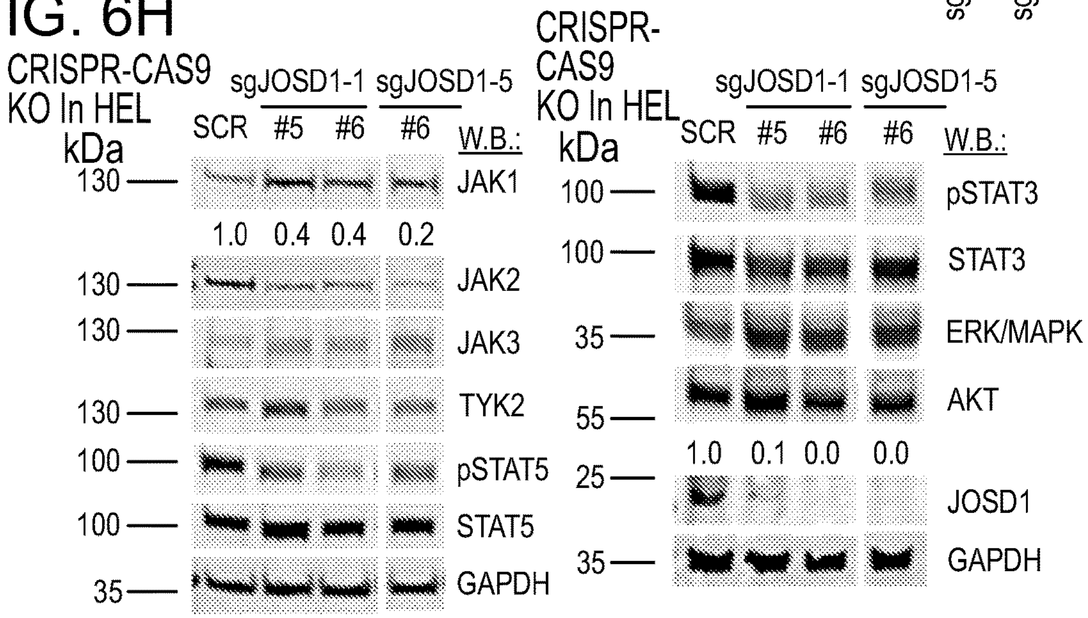
Figure 14A:
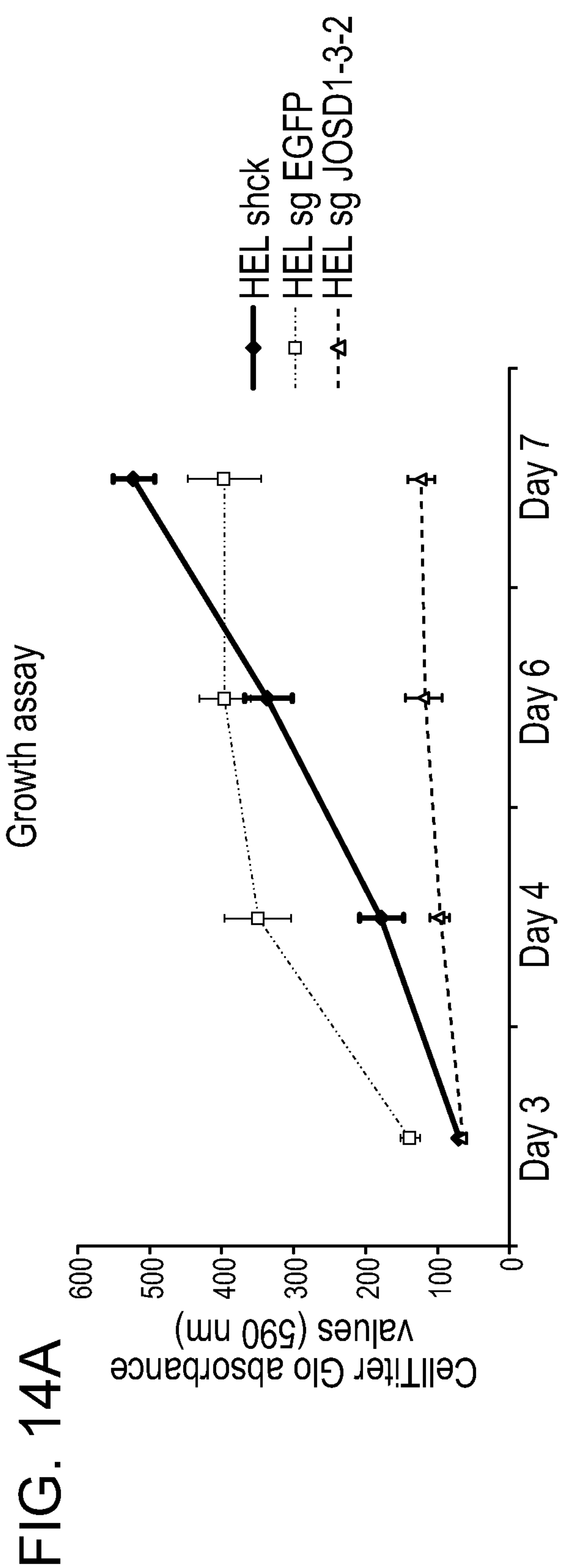
FIG. 14A-FIG. 14B is a line graph and a series of blots showing depletion of JOSD1 by KO leads to targeted degradation of JAK2-V617F.
Figure 14B:
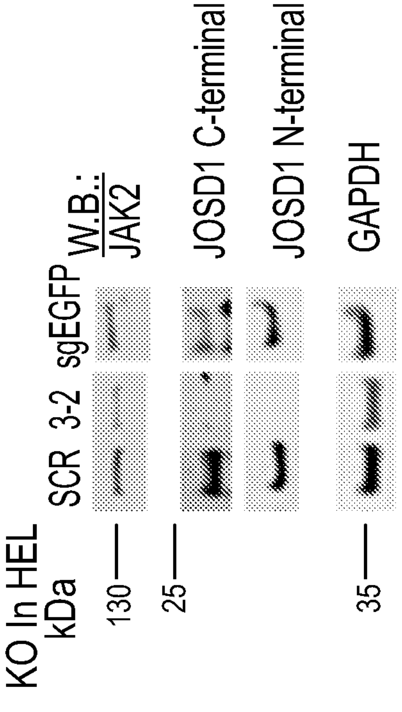
Figure 15A:
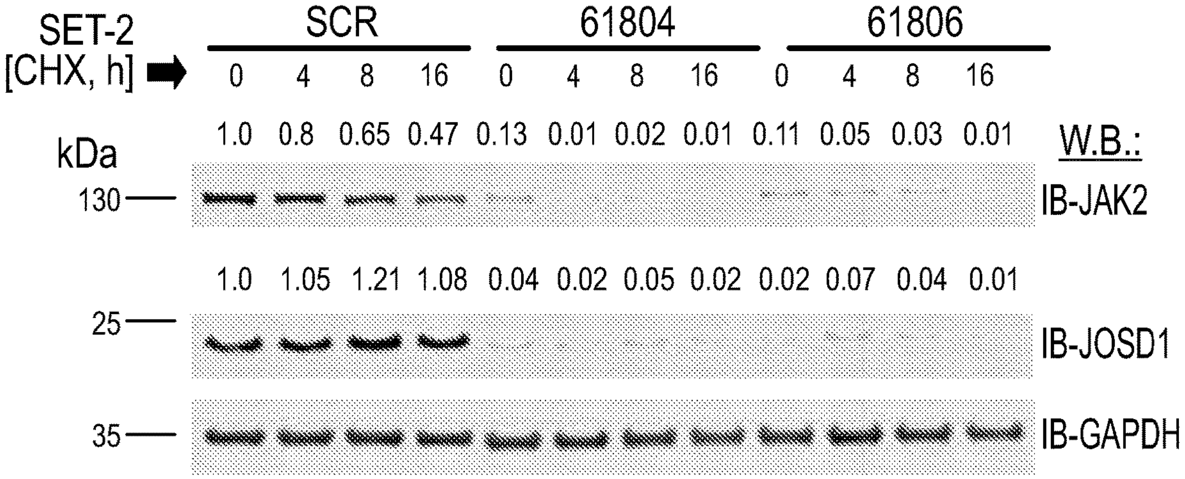
Figure 15B:
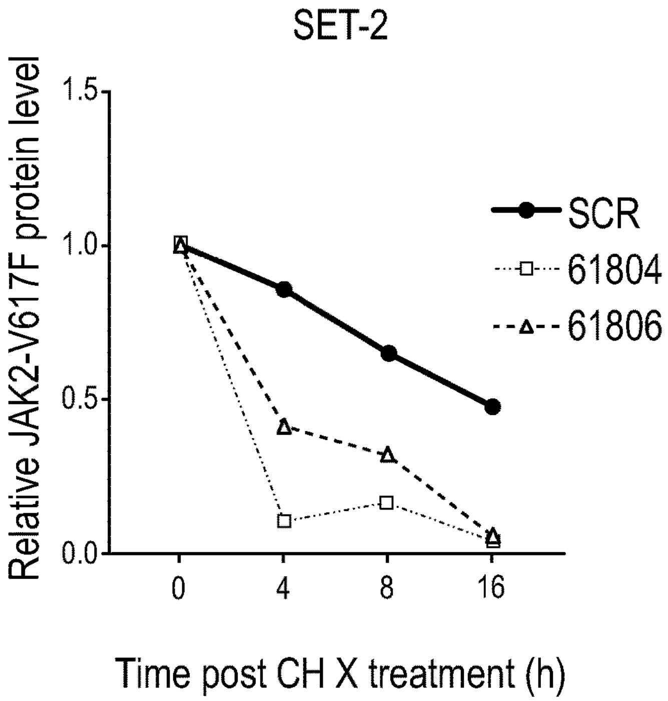

Consistent with the JOSD1 KD results, CRISPR-CAS9 KO of JOSD1 performed in HEL cells led to selective degradation of JAK2 (FIG. 6F), with JOSD1 KO not leading to degradation of wt JAK2 in K562 cells (FIG. 6G). While CRISPR/Cas9-mediated depletion of JOSD1 in HEL cells resulted in significant decreases in JAK2 protein levels and impaired downstream signaling transduction, there was comparatively little degradation of other JAK family members (JAK1, JAK3 and TYK2) or total protein levels of signaling molecules, such as STAT3/5, MAPK and AKT (FIG. 6H). JOSD1 KO in HEL cells correlated with a strong antiproliferative effect (FIG. 14A-FIG. 14B). These results were further validated by analyzing the half-life of JAK2 in JOSD1 KD SET-2 monoclonal cells versus SCR KD control cells. JOSD1 KD was found to considerably shorten the half-life of JAK2-V617F following CHX treatment (FIG. 15A-FIG. 15C), suggesting JOSD1 is a DUB that stabilizes JAK2-V617F. JAK2 protein and mRNA levels were also measured by flow cytometry and Q-PCR (FIG. 15D-FIG. 15E). These results suggest that the loss of JOSD1 leads to destabilization of JAK2 at the protein level with no effect on gene transcription. Taken together, these results strongly support the notion that JAK2-V617F, however not wt JAK2, is a substrate of JOSD1.

Figure 7A:
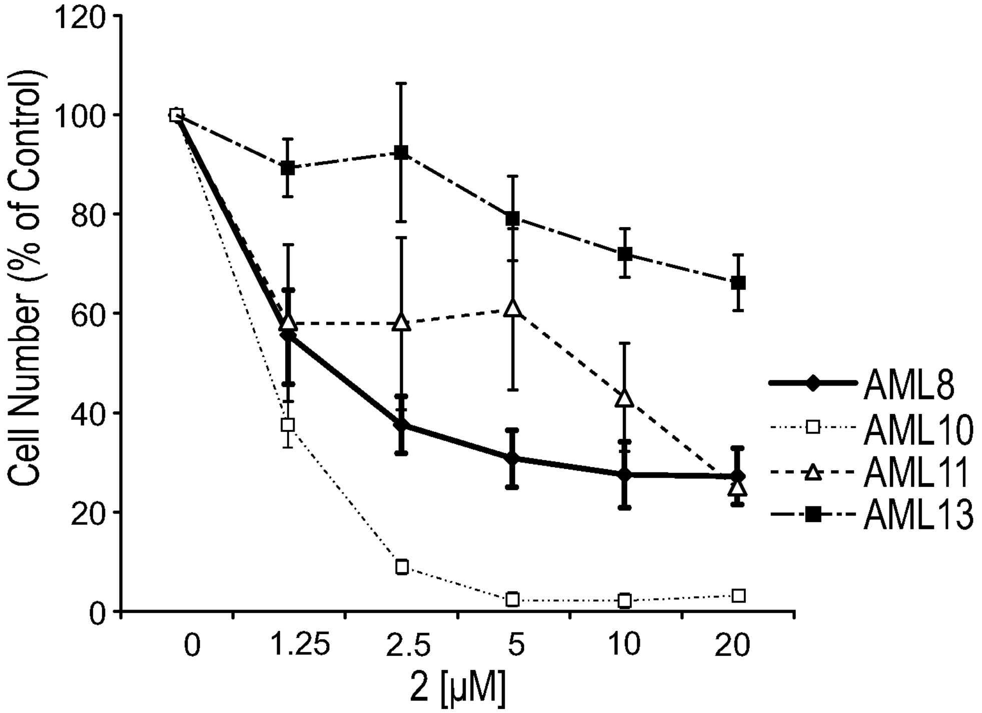
FIG. 7A-FIG. 7H is a series of line graphs and bar graphs showing the targeting of JOSD1 leads to JAK2-V617F-positive primary AML cell death.
Figure 7B:
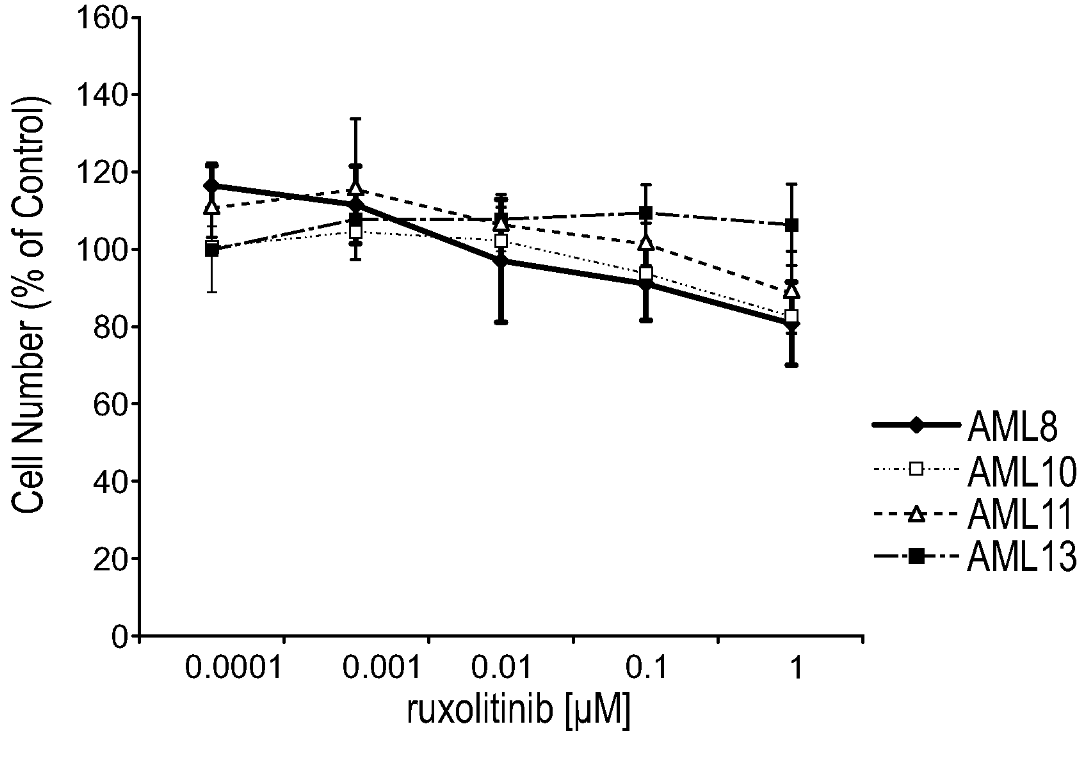
Figure 7C:
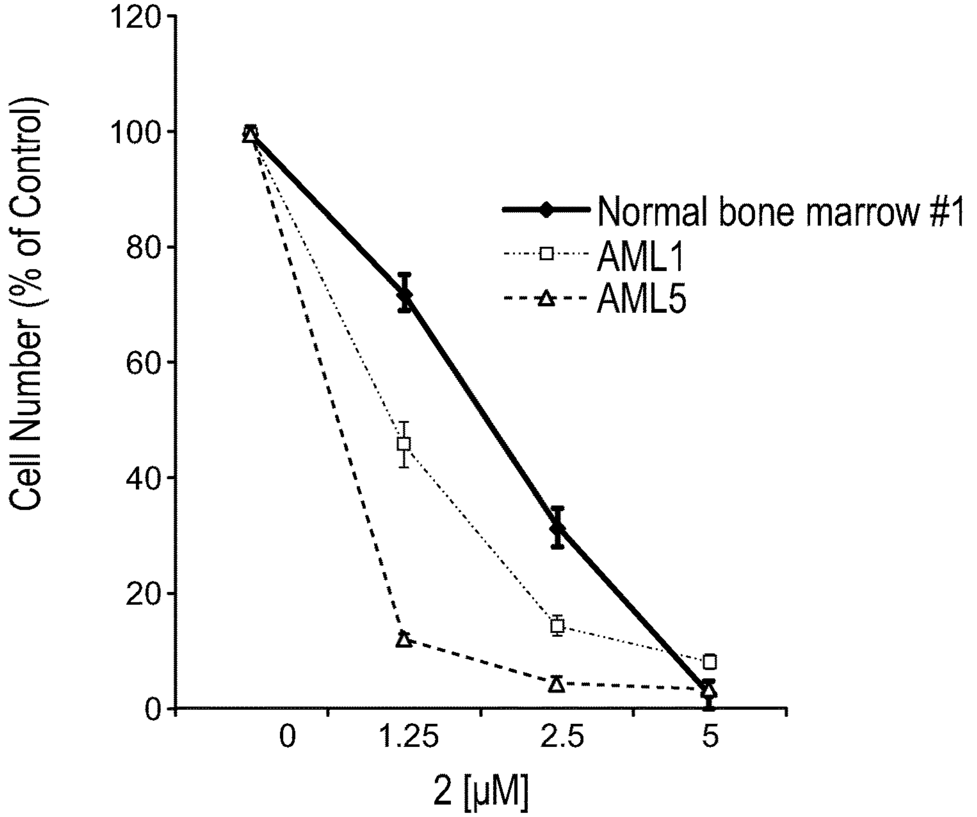
Figure 7D:
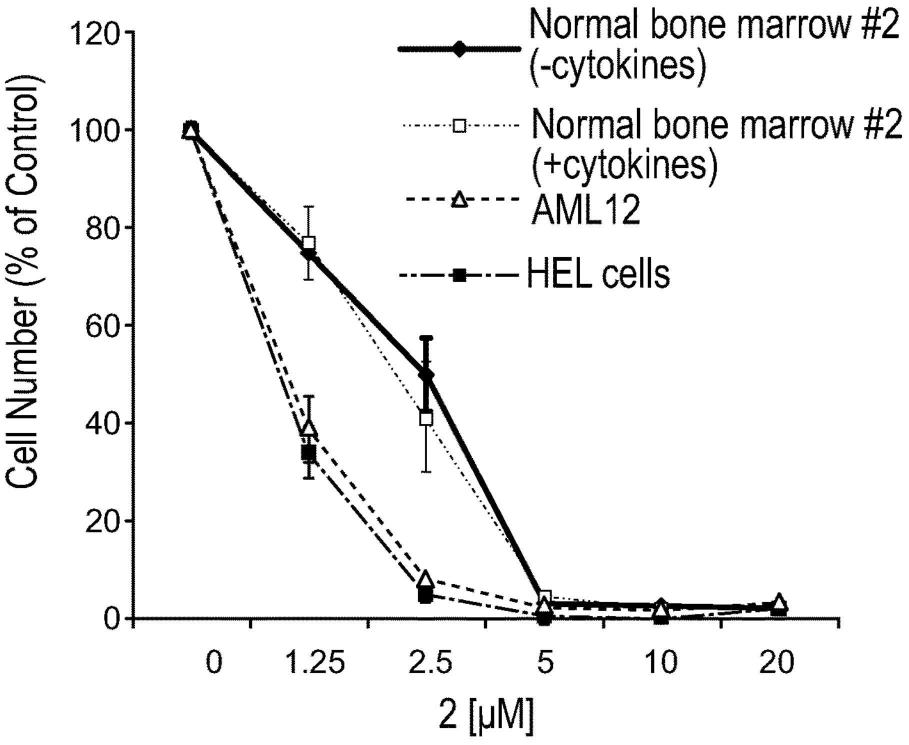
Figure 7E:
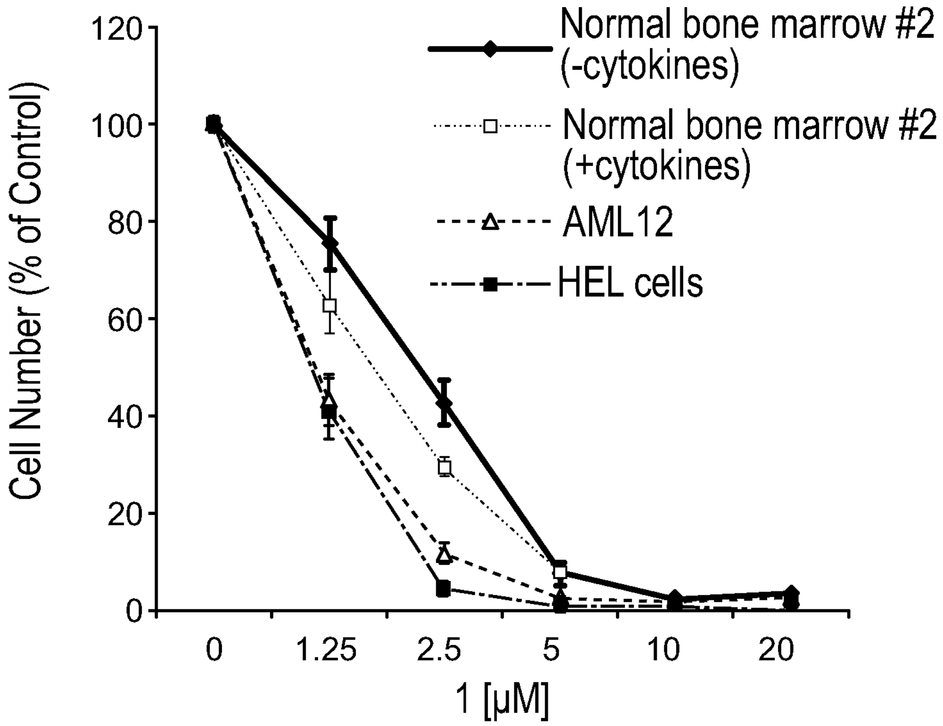
Figure 7F:
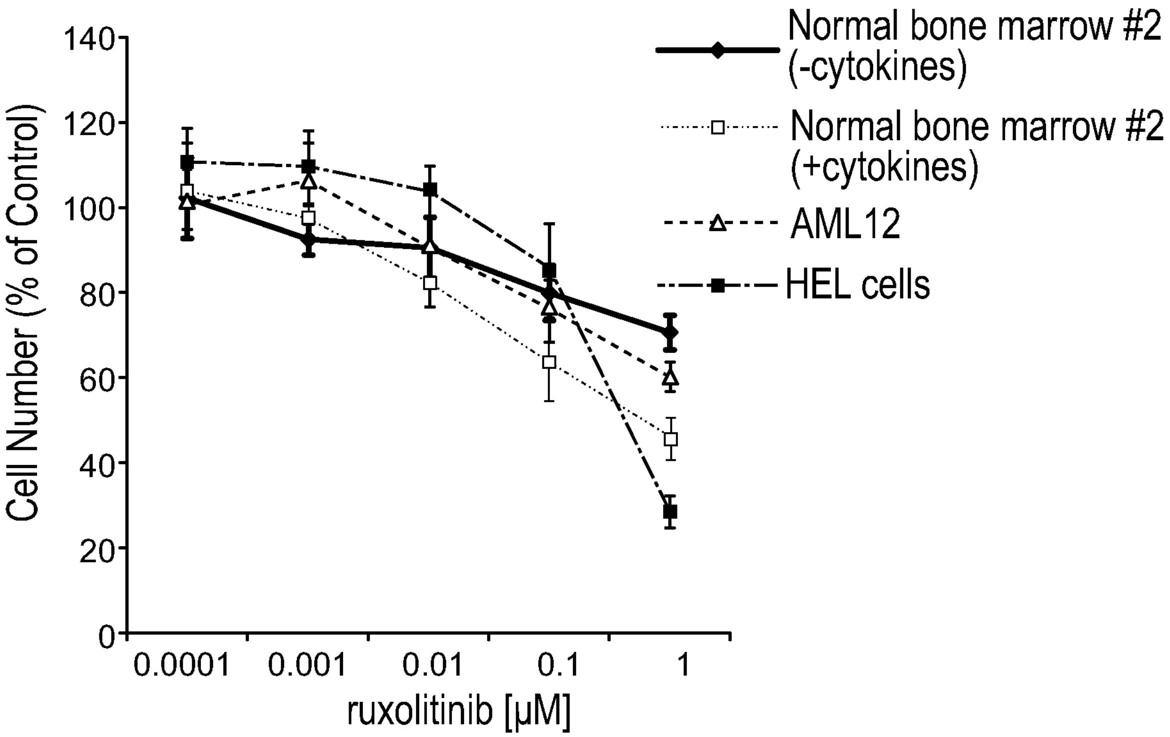

Example 23: Targeting of JOSD1 Leads to JAK2-V617F-Positive Primary AML Cell Death The potency of compound 2 was compared with that of ruxolitinib against JAK2-V617F-positive primary AML patient samples. Josd1 inhibition led to a concentration-dependent decrease in primary cell viability, starting at concentrations around 1 M, as compared to ruxolitinib, treatment with which led to at best modest efficacy at 1 μM (FIG. 7A-FIG. 7B). JAK2-V617F-expressing AML1 (de novo myelodysplastic/myeloproliferative neoplasms (MPD/MDS)), AML5 (secondary AML), and AML12 (secondary AML) samples showed higher sensitivity to treatment with JOSD1-targeting inhibitors than normal bone marrow cells cultured either in the absence or presence of cytokines (FIG. 7C-FIG. 7E). Josd1 inhibition killed >50% of primary AML cells at around 1 μM in contrast to more modest efficacy displayed by ruxolitinib at 1 μM that was indistinguishable from effects against normal bone marrow (FIG. 7C-FIG. 7F). Growth inhibitory effects of compound 2 were observed following 24 h of treatment with higher potency exhibited against JAK2-V617F-positive cells than normal bone marrow cells (FIG. 16A-FIG. 16B). See Table 4 for characteristics of AML cell.

TABLE 4

AML primary patient sample characteristics.

| Primary AML patient sample (date of patient sample vial information acquired) (date of patient sample vial tested in study) | Age | % blasts | Cytogenetics | Mutations |
|---|---|---|---|---|
| AML1<br>De novo<br>MPD/MDS<br>(Oct. 22, 2016)<br>(Oct. 24, 2016) | 45 | 23 (Oct. 22, 2016)<br>23 (Oct. 24, 2016) | 46, XX, inv(6)(p12q21), t(8; 21)(q22; q22), del(9)(q13q32)[20] | JAK2 NM_004972 c.1849G > T p.V617F - in 18.6% of 354 reads |
| AML5<br>Secondary AML<br>(Jan. 2, 2019)<br>(Jan. 2, 2019) | 80 | 25 (Jan. 2, 2019)<br>25 (Jan. 2, 2019) | 46, XY, del(20)(q11.2.q13.3)[8]/ 46, XY, del(7)(q22q36)[3]/ 46, XY[9] | **ASXL1 NM_015338 c.2269C > T p.Q757* - in 3.6% of 618 reads (NEW)<br>**BCOR NM_001123385 c.4310C > G p.S1437* - in 27.1% of 340 reads (NEW)<br>**IDH1 NM_005896 c.394C > T p.R132C - in 12.6% of 627 reads (NEW)<br>JAK2 NM_004972 c.1849G > T p.V617F - in 70.7% of 259 reads<br>U2AF1 NM_006758 c.470A > G p.Q157R - in 45.8% of 435 reads<br>DNMT3A NM_175629 c.2644C > T p.R882C - in 45.0% of 505 reads |
| AML8<br>Secondary AML<br>(Oct. 10, 2017)<br>(May 23, 2017) | 65 | 95 (Oct. 10, 2017)<br>4 (May 23, 2017) | N/A | JAK2 NM_004972 c.1849G > T p.V617F - in 6.7% of 327 reads<br>NRAS NM_002524 c.35G > T p.G12V - in 42.8% of 990 reads |
| AML10<br>Secondary AML<br>(Feb. 27, 2016)<br>(Feb. 29, 2016) | 79 | 20 core (Feb. 27, 2016)<br>4 (Feb. 29, 2016) | 46, XX[20] | JAK2 NM_004972 c.1849G > T p.V617F - in 53.9% of 49 reads<br>SRSF2 NM_001195427 c.284C > A p.P95H - in 56.8% of 118 reads<br>CUX1 NM_181552 c.720delC p.E240fs* - in 45.4% of 1007 reads |

TABLE 4-continued

| AML primary patient sample characteristics. | | | | |
|---|---|---|---|---|
| Primary AML patient sample (date of patient sample vial information acquired) (date of patient sample vial tested in study) | Age | % blasts | Cytogenetics | Mutations |
| | | | | NRAS NM_002524 c.37G > T p.G13C - in 19.6% of 854 reads<br>TET2 NM_001127208 c.3339_3340insA p.D1113fs* - in 43.3% of 402 reads<br>TET2 NM_001127208 c.944delC p.S315fs* - in 45.1% of 2592 reads |
| AML11 Secondary AML (Dec. 20, 2018) (May 7, 2018) | 64 | 30-40 (Dec. 20, 2018) 8 (May 7, 2018) | N/A | IDH2 NM_002168 c.419G > A p.R140Q - in 12.5% of 1080 reads<br>JAK2 NM_004972 c.1849G > T p.V617F - in 34.4% of 422 reads<br>BCOR NM_001123385 c.1659_1659insT p.V554fs* - in 17.7% of 203 reads<br>BCORL1 NM_021946 c.4975C > T p.Q1659* - in 14.3% of 497 reads<br>EZH2 NM_004456 c.2050C > T p.R684C - in 18.6% of 221 reads |
| CMML12 Secondary CMML (Aug. 26, 2016) (Dec. 14, 2018) | 67 | 15 (Aug. 26, 2016) 6 (Dec. 14, 2018) | 46, XY[20] | JAK2 NM_004972 c.1849G > T p.V617F - in 3.6% of 412 reads<br>NRAS NM_002524 c.34G > A p.G12S - in 43.2% of 919 reads<br>KIT NM_000222 c.2447A > T p.D816V - in 5.6% of 357 reads<br>SF3B1 NM_012433 c.1998G > T p.K666N - in 50.7% of 290 reads<br>TET2 NM_001127208 c.2516delA p.H839fs* - in 52.0% of 1044 reads<br>TET2 NM_001127208 c.368delG p.R123fs*5 - in 48.5% of 1669 reads |
| AML13 Secondary AML (Feb. 12, 2016) (Apr. 22, 2016) | 69 | 51 (Feb. 12, 2016) 4 (Apr. 22, 2016) | 46, XY, add(10)(p11.2)[10]/ 47, XY, +21[6]/ 46, XY[4] | JAK2 NM_004972 c.1849G > T p.V617F - in 92.3% of 339 reads<br>CUX1 NM_181552 c.622C > T p.R208* - in 12.3% of 1765 reads<br>IDH2 NM_002168 c.419G > A p.R140Q - in 43.3% of 1776 reads<br>RUNX1 NM_001754 c.592G > A p.D198N - in 4.3% of 990 reads* (new)<br>TP53 NM_000546 c.524G > A p.R175H - in 21.6% of 125 reads |

Figure 7G:
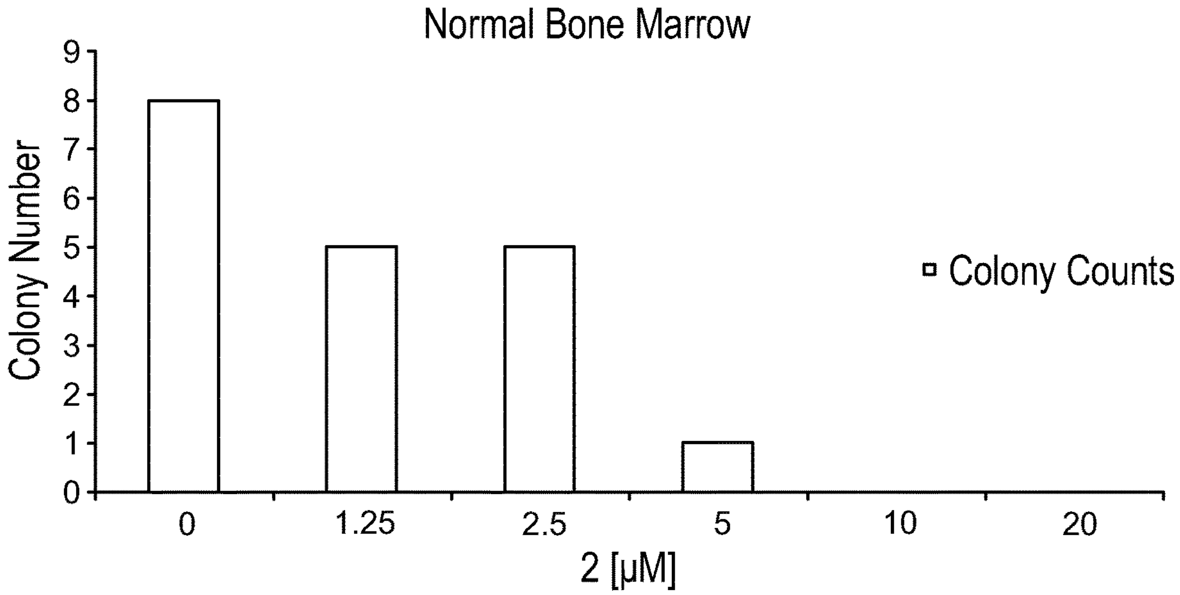
Figure 7H:
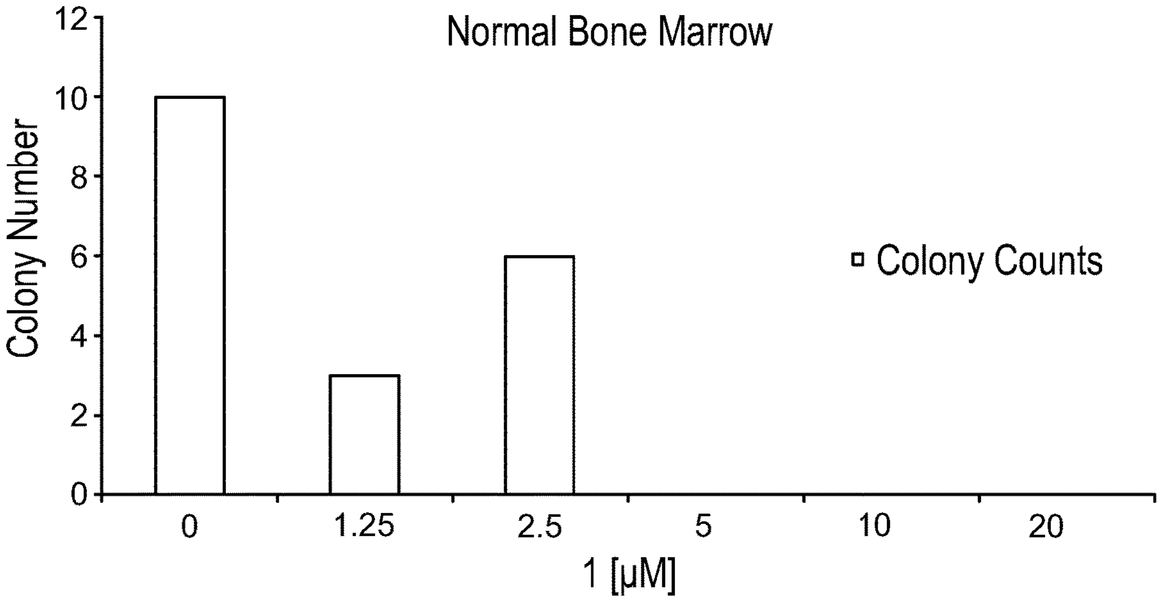

In contrast, ruxolitinib showed similar efficacy against JAK2-V617F-positive cells and normal bone marrow cells (FIG. 16C). Normal bone marrow cell colony formation and cell proliferation were significantly inhibited by Josd1 inhibitor treatment at concentrations of 5 µM and higher. Concentrations of compounds 1 and 2 at 5 µM or higher significantly impaired normal bone marrow colony formation, however colonies were able to form at concentrations up to 2.5 µM (FIG. 7G-FIG. 7H); these results are consistent with treatment effects observed for normal bone marrow cells in liquid proliferation assays. These studies provide a novel approach to selective targeting of mutated JAK2-mediated signaling in MPN patients with DUB inhibitors, ideally with improved selectivity than has thus far been achieved with JAK2 kinase inhibitors.

Other Embodiments

While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this disclosure has been particularly shown and described with references to preferred embodiments thereof, it will be understood by those skilled in the art that various changes in form and details may be made therein without departing from the scope of the disclosure encompassed by the appended claims.

What is claimed is:

1. A method of treating a disease or disorder mediated by dysregulated Janus Kinase 2 (JAK2) activity, in a subject in need thereof, comprising administering a therapeutically effective amount of one or more Josephin domain containing 1 (JOSD1) deubiquitinase (DUB) inhibitors or stereoisomers or pharmaceutically acceptable salts thereof, wherein the JAK2 comprises a valine-to-phenylalanine at position 617 (V617F) mutation; and wherein the one or more JOSD1 DUB inhibitors are selected from the group consisting of:

(1)

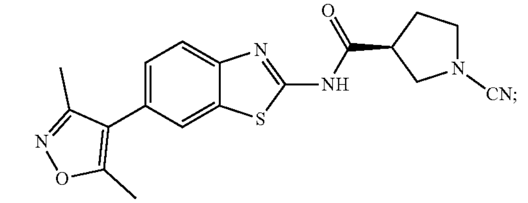

(2)

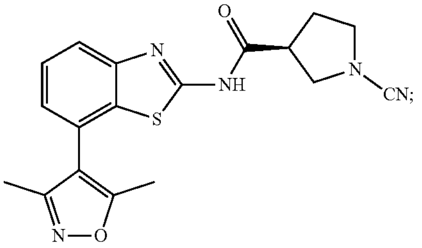

(3)

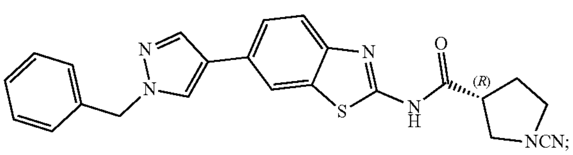

(4)

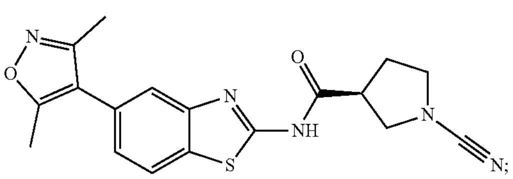

(5)

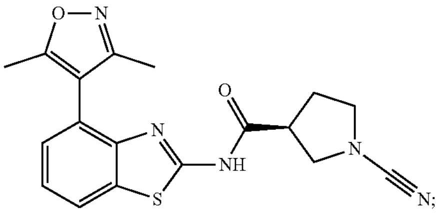

(6)

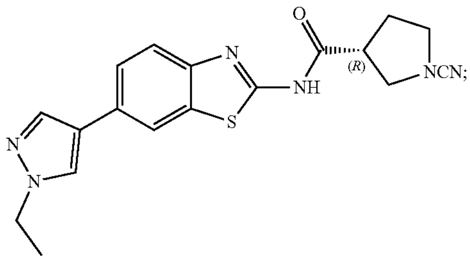

-continued (7)

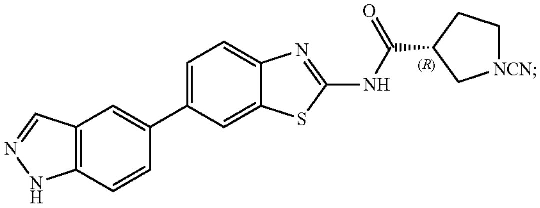

(8)

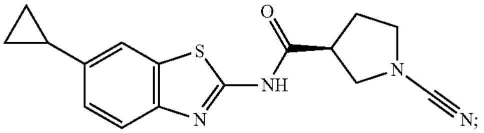

(9)

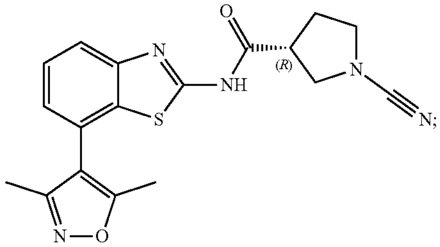

(10)

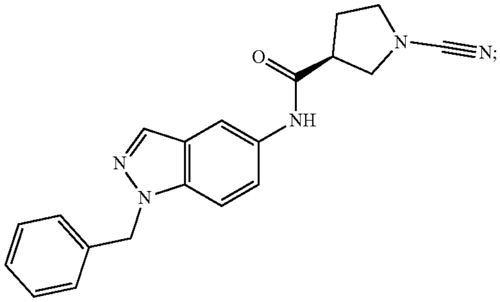

(11)

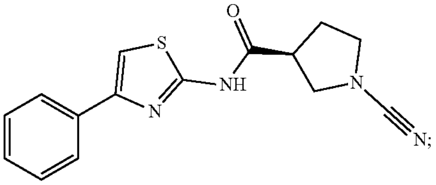

(12)

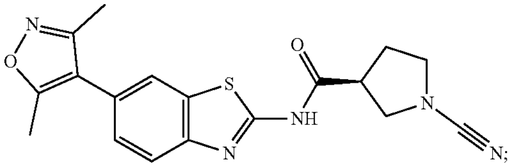

(13)

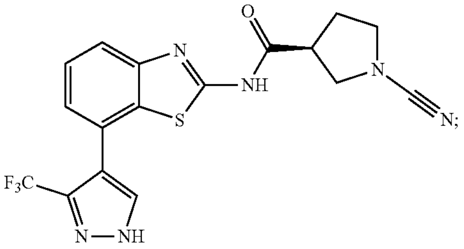

-continued
(14)
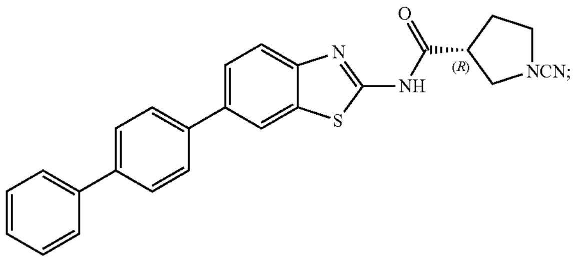
(15)
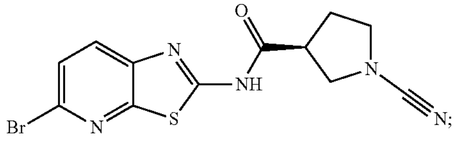
(16)
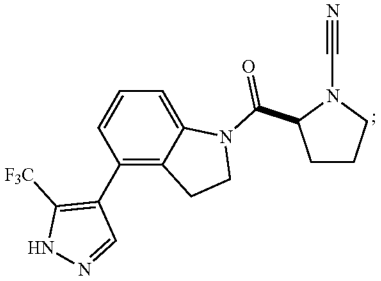
(17)
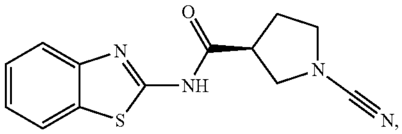
(18)
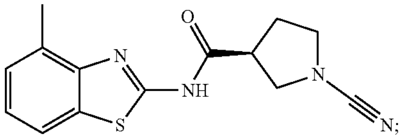
(19)
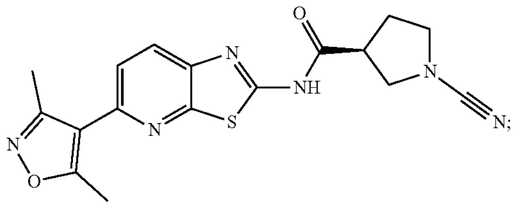
(20)
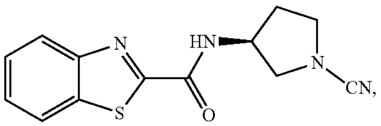
(21)
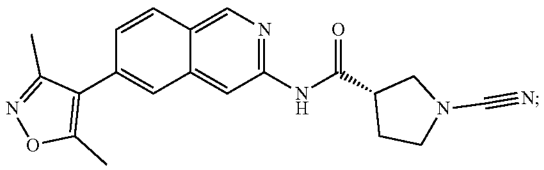
-continued
(22)
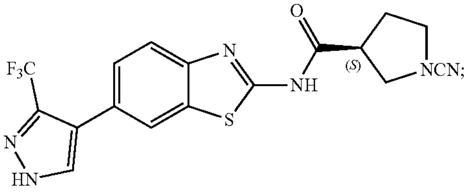
(23)
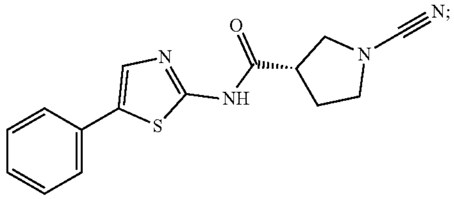
(24)
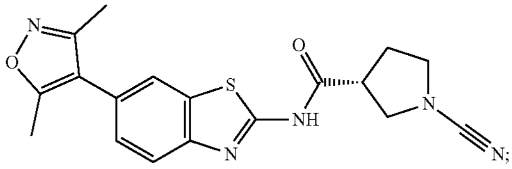
(25)
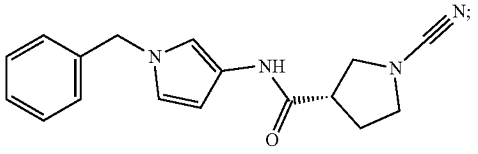
(26)
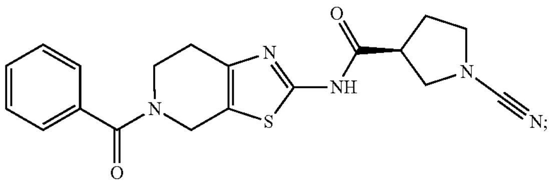
(27)
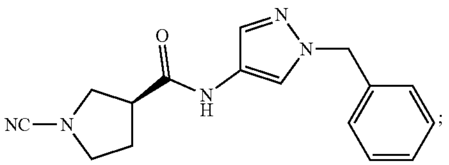
(28)
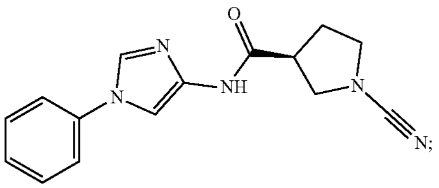
(29)
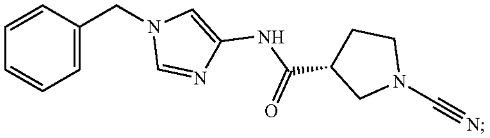
(30)
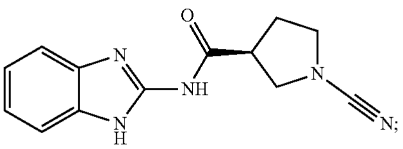

-continued
(31)
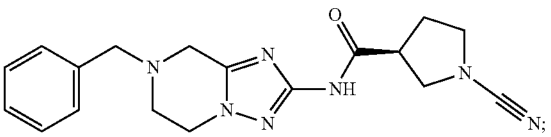
(32)
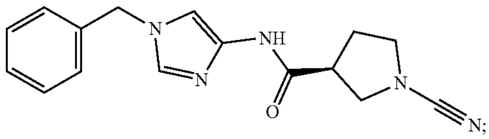
(33)
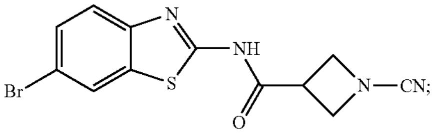
(34)
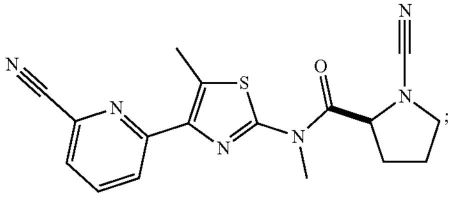
(35)
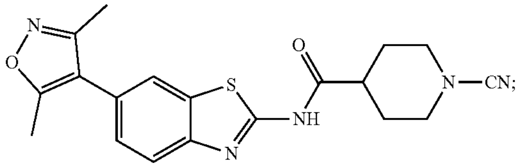
(36)
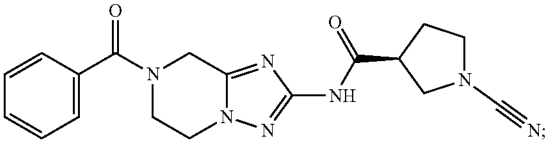
(37)
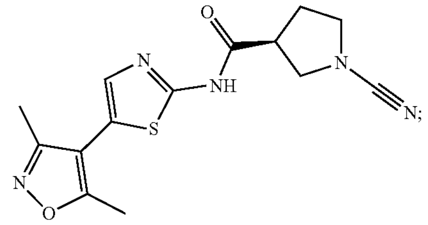
(38)
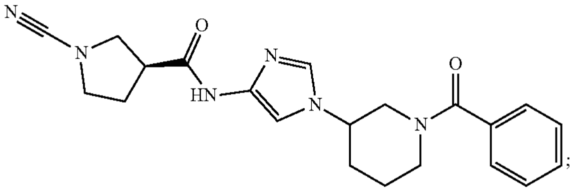
(39)
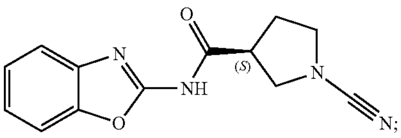
-continued
(40)
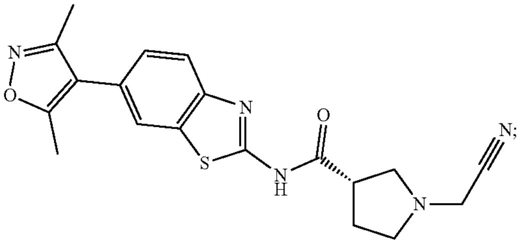
(41)
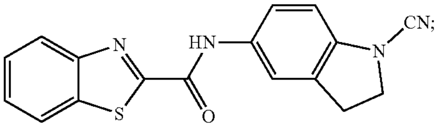
(42)
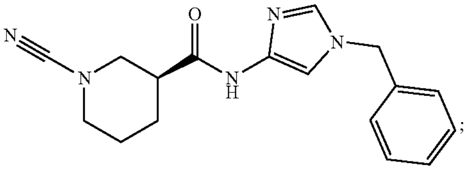
(43)
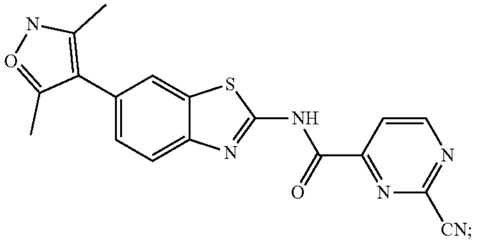
(44)
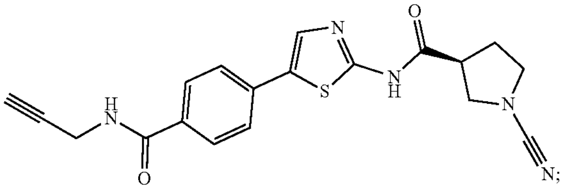
(45)
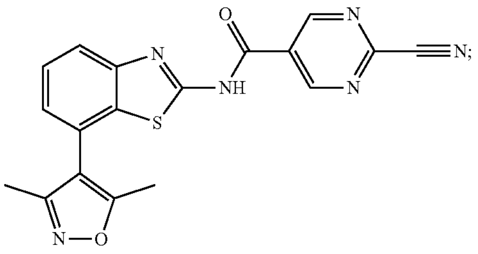
(46)
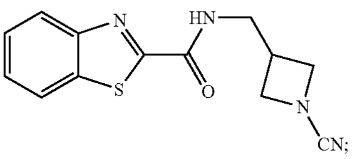

-continued
(47)
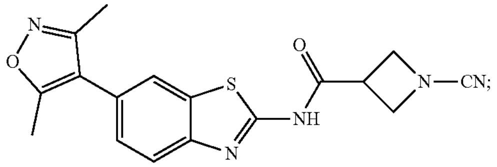
(48)
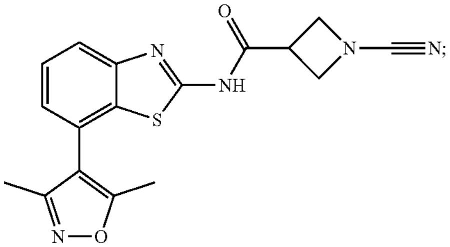
(49)
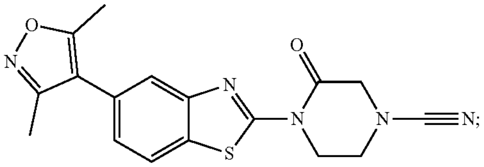
(50)
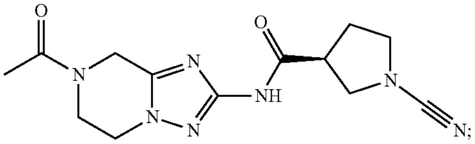
(51)
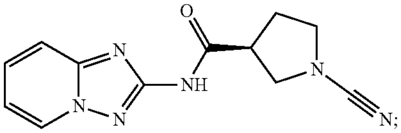
(52)
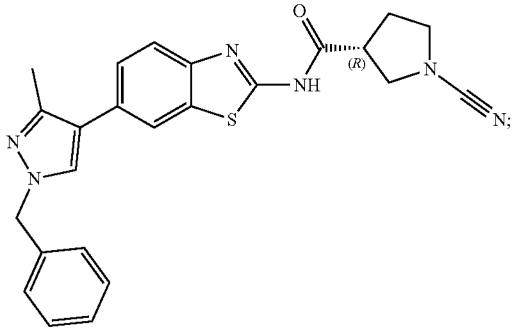
(53)
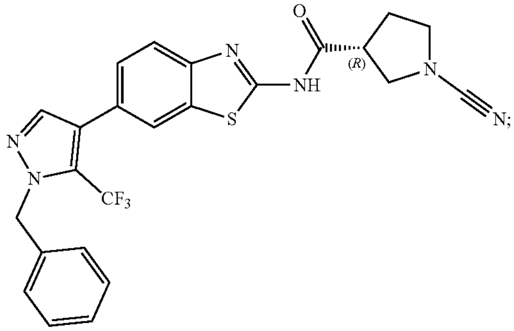
-continued
(54)
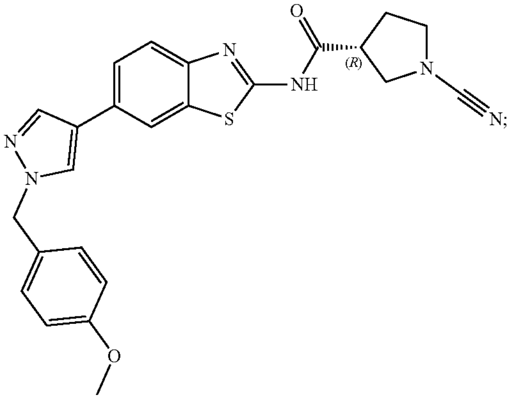
(55)
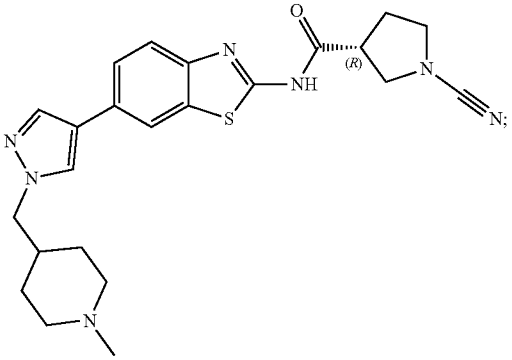
(56)
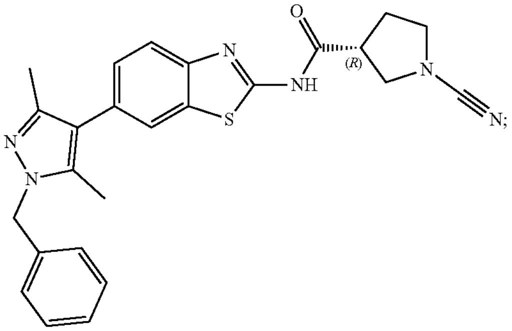
(57)
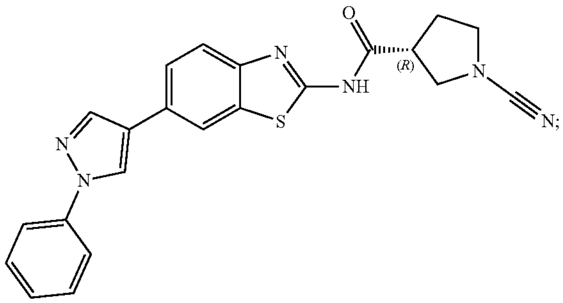

-continued
(58)
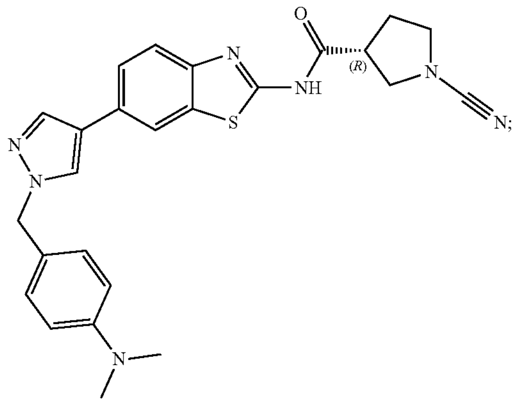
(59)
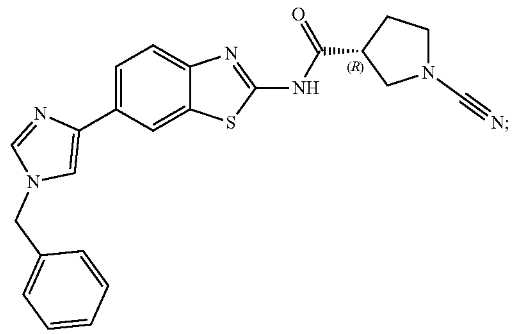
(60)
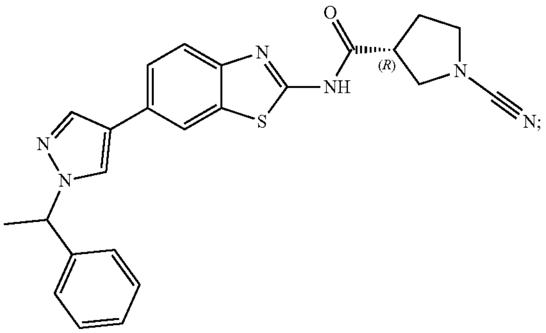
(61)
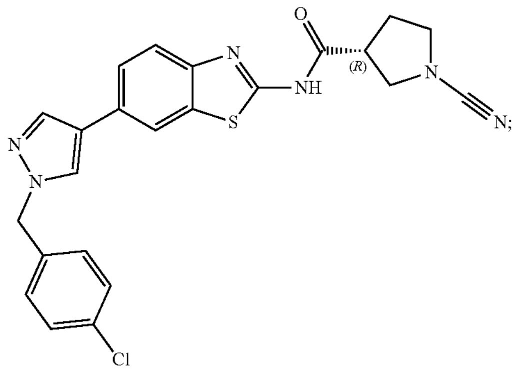
-continued
(62)
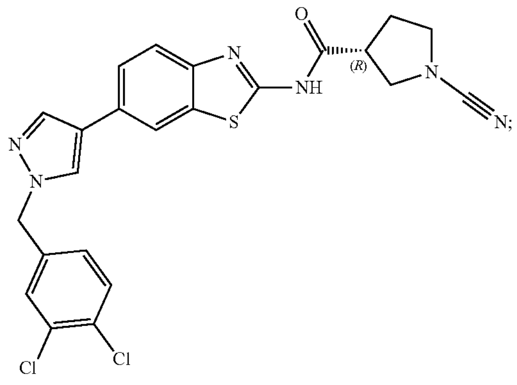
(63)
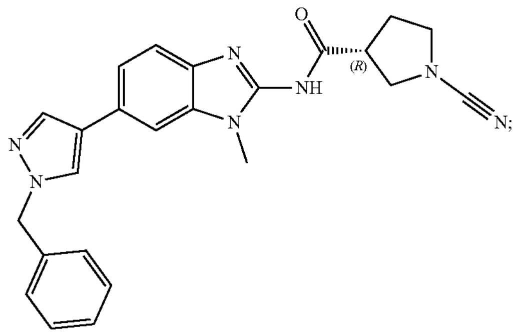
(64)
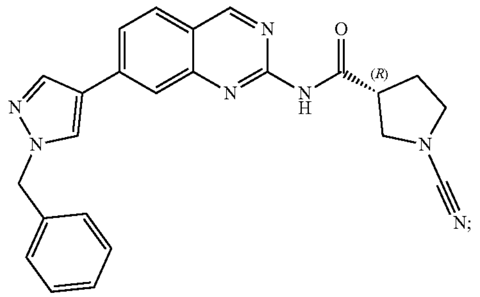
and
(65)
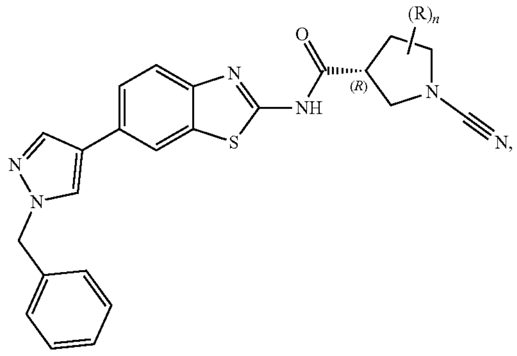
wherein R is methyl or halogen, and n is an integer of 1-7, and stereoisomers or pharmaceutically acceptable salts thereof.

2. The method of claim 1, wherein the one or more JOSD1 DUB inhibitors are any of:

(1)

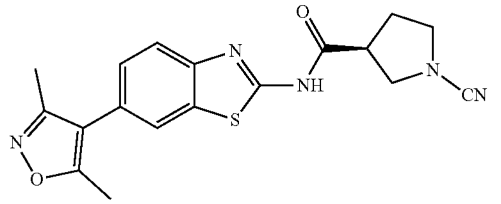

and (2)

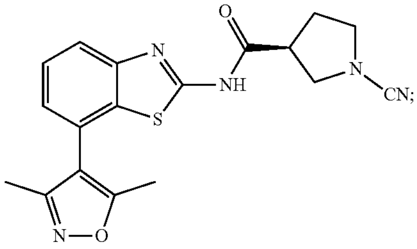

;

and stereoisomers or pharmaceutically acceptable salts thereof.

3. The method of claim 1, wherein the JAK2 comprises a translocation-Ets-leukemia-JAK2 gene fusion, a pericentriolar material 1-JAK2 gene fusion, or a JAK2 with one or more mutations in exon 12.

4. The method of claim 1, wherein the disease is cancer.

5. The method of claim 4, wherein the cancer is a myeloproliferative neoplasm (MPN).

6. The method of claim 5, wherein the MPN is a myeloid neoplasm.

7. The method of claim 6, wherein the myeloid neoplasm is myelodysplastic syndrome (MDS), JAK2-V617F-positive MDS, chronic myelomonocytic leukemia (CMML), or acute myeloid leukemia (AML).

8. The method of claim 6, wherein the myeloid neoplasm is AML.

9. The method of claim 5, wherein the MPN is Polycythemia Vera (PV), Essential Thrombocythemia (ET), or Primary Myelofibrosis (ML).

10. The method of claim 1, wherein the one or more JOSD1 DUB inhibitors are co-administered with a therapeutically effective amount of a chemotherapy or targeted therapy; or wherein the one or more JOSD1 DUB inhibitors are co-administered with a therapeutically effective amount of a chemotherapy or targeted therapy in preparation for or in maintenance therapy after a hematopoietic stem cell transplant for MPN or AML.

11. The method of claim 10, wherein the chemotherapy is doxorubicin, daunorubicin, cytarabine, cladribine, fludarabine, mitoxantrone, etoposide, 6-thioguanine, methotrexate, azacytidine, all trans retinoic acid, arsenic trioxide, or decitabine; or wherein the targeted therapy comprises a poly adenosine diphosphate-ribose polymerase (PARP) inhibitor; or wherein the targeted therapy comprises a JAK2 inhibitor; or wherein the targeted therapy comprises a targeted inhibitor of proviability signaling molecule; or wherein the targeted therapy comprises at least one of a PARP inhibitor, a targeted inhibitor of proviability signaling molecule, and a JAK2 inhibitor.

12. The method of claim 11, wherein the PARP inhibitor is selected from the group of olaparib, rucaparib, niraparib, veliparib, and talazoparib.

13. The method of claim 11, wherein the JAK2 inhibitor is selected from the group of ruxolitinib, fedratinib, momelotinib, and baricitinib.

14. The method of claim 11, wherein the targeted inhibitor of proviability signaling molecule is venetoclax or navitoclax.

15. A method of reducing the activity of JOSD1 DUB in a cell, either in vivo or in vitro, comprising administering a therapeutically effective amount of one or more JOSD1 DUB inhibitors or stereoisomers or pharmaceutically acceptable salts thereof of claim 1.

* * * * *

SEQUENCE LISTING

Sequence total quantity: 19
SEQ ID NO: 1 moltype = AA length = 202
FEATURE Location/Qualifiers
source 1..202
mol_type = protein
organism = Homo sapiens
SEQUENCE: 1
MSCVPWKGDK AKSESLELPQ AAPPQIYHEK QRRELCALHA LNNVFQDSNA FTRDTLQEIF 60
QRLSPNTMVT PHKKSMLGNG NYDVNVIMAA LQTKGYEAVW WDKRRDVGVI ALTNVMGFIM 120
NLPSSLCWGP LKLPLKRQHW ICVREVGGAY YNLDSKLKMP EWIGGESELR KFLKHHLRGK 180
NCELLLVVPE EVEAHQSWRT DV 202

SEQ ID NO: 2 moltype = DNA length = 3746
FEATURE Location/Qualifiers
source 1..3746
mol_type = genomic DNA
organism = Homo sapiens
SEQUENCE: 2
agtcaacgca gaaggagcga gaacgttcgg ccgaaaagcc cggcacagag aagggagggg 60
tgctgaaagc cgcggactgc agccgctggc ctggctgccg ccccgaaaca acgcccacgc 120
ccgggagaag ggcaggctgg cgtccagggc cgcggccaga gggctagaat ccgcgccttc 180
cgagggagcc gcgccctgcg ggccccaccg tacccgaggg gatggagggc tgcccccgag 240
gcccccgcgc ggctcgcggt cccacgcctg ccggcccgcg ctagctactc gactcgtgcg 300
ctaaatttat ccgtcaccca ggccttgtct cccgagtcat tggcgtcgtg gttcaaaaga 360
aatggaagaa aaggagcgat gtgaccgatt gtgttcggtc ctcctgcttt gaggcctggc 420
atttgcagag ggaaacagca agaaaatcgt ggggattttg gagggggggtg ggagggaagg 480
gtggggaaac ggaaacaagg tcttacattt tatgtgtttt tttaaattct gcactttgac 540
agtggtagca aaataaaagt aatccaaaag ttatttttct attgagaaga gagaagaggt 600
gggttttatt tttttccttt tgattccaat cttttctccc agtgacaaag cataaatcat 660
ggacaccaga gaataaggtg gacctcagga atccggaaaa gactgagaag cttacattct 720
tcctctagag ggaagagtgg ggtgtttata gccatctctg gaacctaaaa caaaaaacat 780
gagttgtgtg ccatggaaag gagacaaggc caaatctgaa tcattggagc tgccccaggc 840
agcaccccca caaatctacc atgagaaaca gcgcagggag ctttgtgccc tccacgccct 900
caataacgtc ttccaggaca gcaatgcctt cacccgggat acgctgcaag agatttttcca 960
gaggttgtct ccaaacacca tggtgacacc tcacaagaag agcatgctgg gaaatggcaa 1020
ctacgatgtg aatgtcatta tggcagcact tcagaccaaa ggctatgaag ctgtttggtg 1080
ggacaagcgc agggatgtcg gtgtcattgc cctcactaac gtcatgggct tcatcatgaa 1140
tctgccctcc agcctatgct ggggtccact gaaactgccc ctcaaaaggc agcactggat 1200
ctgtgttcga gaggtgggag gggcctacta caacctcgac tccaaactca agatgcccga 1260
gtggattgga ggcgagagcg agctcaggaa gtttctaaaa catcatttgc gaggaaagaa 1320
ctgtgaactc ctgctggtgg taccagaaga ggtagaggct catcagagtt ggaggaccga 1380
tgtgtaacag ttctgcccaa cctccctctc gcctcagccc cttcagtcct ctgtgacgtg 1440
ctgtggcctc tacagtgggt ctgcccttgc cacttcccca aacatctcat caagtttttc 1500
cccttcagat ctgacagtgc aataggacag acgtgtggac tgttataaga actactcagt 1560
gttttgttcc tgggcaagga aggtaggagt tctgtgcact taaggccagt ggtcacaaac 1620
ccttgtttta tttaagagac agaggagaaa gtggagcggg gagggaatcc tagcttattt 1680
tccctttttct atgaggactt gacacaggtt ctgctgagtt gtcactgctg ctccagactc 1740
acctagagat gctgcctcca ctttccatcc tgtctgggtc tgaaaacagt gggtctgcag 1800
atagtgccca caaaccccat gtgactggtt tgaaggaccc agagcataaa ggtctctcag 1860
gaaaccatgt ccaaaaccct agcagcggta cagcatgctg tctccaaccc ttatccccag 1920
gtttaagggt ggtttatggc catacgtgga ggttttttgt tgttgttttt gagactgagt 1980
ttcactcttg ttgcccaggc tggagtgcaa tggcaccatc tcggctcact gcaacctcca 2040
cctcctggtt caagcgattc tcaggcctca gcttcccaag tagttgggat tacaggcgcc 2100
tgccaccaca cctggctaat tttgtatttt tagtagagat ggggtttctc catgttggtc 2160
aggctggtct caaactcccg acctcaagtg atctgcccgc cttggcctcc caaagtgctg 2220
ggattacagg cgtgagccac cgcacccggc agagttttat aatgaaaaat taactaatat 2280
tctagtatga agtgaggagg atactgaaca ggatgtggct aaagccaacc tgggacagcc 2340
atggggtggc ttggtttctt cactccagtg ttgtccctac catttcgcag cattgattta 2400
ggaggctctg ggacaaaaga gaagccaaag agcagttttc ccagttcact cactctggca 2460
aaatcaggaa aaaaaagtct gcttttgaca tcaaattcca ctaatttggg gcagcgttgg 2520
gtgaggaaag tattgtgaag acaggcttct tggagtaggg gcagccacaa ttcagtagac 2580
actctaggct cggaggctgc cactgtagtt gccaagctca ggttgggtgg ttctgtgctg 2640
tatggatgga ataggacctg ggctggtcat cttcatgtcg tttcctctct gtatcaatgg 2700
aagttcaacc cgcccctacc tcttcagata gttgtaggcc acttttctct tgtaactttg 2760
gaaaacaaaa gaggagaaat aagtatcata ccatatgcgt gtctccaaag tggatgtggt 2820
tgcctcaagg caggtggcag gcaggggtga cctgctggcc ctcagatcaa tggtcgtggc 2880
aggtctgaga gctgtcccac tggccagact tctctccagc agcaaagcca gcctggggct 2940
tgcatgttga tcctgagcaa gcttaacggg gtgaagctgg gctttctccc ccctgtgact 3000
ggagtgcatg ttgacaccag cactttttct gcacatgtat cttcaatcca acaaggccgt 3060
ttttttaatg ctgagtaaca ggccaccaag cggctactgc gttatatctt ctcagcaact 3120
ggccgcagtc tcttctgcac cattttctac accagacctg cttggcacca cagggagctc 3180
ttttcctgcc ctgcacaatg acattccaac caccaccagc cagacattac agccaacctt 3240
gctgattgtc acaagcagga ccttggggcc actggcactg tcagatagta agccatttct 3300
tgggtagagg aggaaactcc tctccacaaa tccacttggg cctgtgcaaa tggcacttga 3360

-continued

```
aagagtcccc atgcacttgg agtccatgag ccaatgggat atgcaaagac gcttaaacat  3420
ttcagggctg gtttctctgt tcatatccaa ttctggtgct taggaacagg gacccatgct  3480
gatgcccaag ggcaaaaagc cccacttcct ttaaggaagt gaacaggcct gaccctgatg  3540
cccaataacg ggcaacccta ggctttttgt ttttcttgct tttattcctt tttgttgttg  3600
gccttgtgct gcgtttgttt acaaaagatg tattttgttt aaccaaatat taaaaatgga  3660
aaactccata tatgtctcct tgtctgcctg aattctataa ttgtgtaaag aaaaataaac  3720
tttagtatga cgctgtttta aaagga                                      3746

SEQ ID NO: 3            moltype = DNA  length = 25
FEATURE                 Location/Qualifiers
source                  1..25
                        mol_type = other DNA
                        organism = synthetic construct
SEQUENCE: 3
caccgtgaag cccatgacgt tagtg                                       25

SEQ ID NO: 4            moltype = DNA  length = 25
FEATURE                 Location/Qualifiers
source                  1..25
                        mol_type = other DNA
                        organism = synthetic construct
SEQUENCE: 4
aaaccactaa cgtcatgggc ttcac                                       25

SEQ ID NO: 5            moltype = DNA  length = 24
FEATURE                 Location/Qualifiers
source                  1..24
                        mol_type = other DNA
                        organism = synthetic construct
SEQUENCE: 5
caccgcactg gatctgtgtt cgag                                        24

SEQ ID NO: 6            moltype = DNA  length = 24
FEATURE                 Location/Qualifiers
source                  1..24
                        mol_type = other DNA
                        organism = synthetic construct
SEQUENCE: 6
aaacctcgaa cacagatcca gtgc                                        24

SEQ ID NO: 7            moltype = DNA  length = 25
FEATURE                 Location/Qualifiers
source                  1..25
                        mol_type = other DNA
                        organism = synthetic construct
SEQUENCE: 7
caccgattgc cctcactaac gtcat                                       25

SEQ ID NO: 8            moltype = DNA  length = 25
FEATURE                 Location/Qualifiers
source                  1..25
                        mol_type = other DNA
                        organism = synthetic construct
SEQUENCE: 8
aaacatgacg ttagtgaggg caatc                                       25

SEQ ID NO: 9            moltype = DNA  length = 25
FEATURE                 Location/Qualifiers
source                  1..25
                        mol_type = other DNA
                        organism = synthetic construct
SEQUENCE: 9
caccgctgga tctgtgttcg agagg                                       25

SEQ ID NO: 10           moltype = DNA  length = 25
FEATURE                 Location/Qualifiers
source                  1..25
                        mol_type = other DNA
                        organism = synthetic construct
SEQUENCE: 10
aaaccctctc gaacacagat ccagc                                       25
```

-continued

```
SEQ ID NO: 11          moltype = DNA  length = 25
FEATURE                Location/Qualifiers
source                 1..25
                       mol_type = other DNA
                       organism = synthetic construct
SEQUENCE: 11
caccgcgctg caagagattt tccag                                          25

SEQ ID NO: 12          moltype = DNA  length = 25
FEATURE                Location/Qualifiers
source                 1..25
                       mol_type = other DNA
                       organism = synthetic construct
SEQUENCE: 12
aaacctggaa aatctcttgc agcgc                                          25

SEQ ID NO: 13          moltype = DNA  length = 20
FEATURE                Location/Qualifiers
source                 1..20
                       mol_type = other DNA
                       organism = synthetic construct
SEQUENCE: 13
ggataaatac tggtgtgagg                                                20

SEQ ID NO: 14          moltype = DNA  length = 20
FEATURE                Location/Qualifiers
source                 1..20
                       mol_type = other DNA
                       organism = synthetic construct
SEQUENCE: 14
gttcacctcc cagtactcca                                                20

SEQ ID NO: 15          moltype = DNA  length = 20
FEATURE                Location/Qualifiers
source                 1..20
                       mol_type = other DNA
                       organism = synthetic construct
SEQUENCE: 15
tagcagggag ttcatgaagc                                                20

SEQ ID NO: 16          moltype = DNA  length = 57
FEATURE                Location/Qualifiers
source                 1..57
                       mol_type = other DNA
                       organism = synthetic construct
SEQUENCE: 16
ccggcctcga ctccaaactc aagatctcga gatctgagtt tggagtcgag gtttttg       57

SEQ ID NO: 17          moltype = DNA  length = 57
FEATURE                Location/Qualifiers
source                 1..57
                       mol_type = other DNA
                       organism = synthetic construct
SEQUENCE: 17
ccggctacga tgtgaatgtc attatctcga gataagacat tcacatcgta gtttttg       57

SEQ ID NO: 18          moltype = DNA  length = 58
FEATURE                Location/Qualifiers
source                 1..58
                       mol_type = other DNA
                       organism = synthetic construct
SEQUENCE: 18
ccggttgcga ggaaagaact gtgaactcga gttcacagtt ctttcctcgc aatttttg      58

SEQ ID NO: 19          moltype = DNA  length = 58
FEATURE                Location/Qualifiers
source                 1..58
                       mol_type = other DNA
                       organism = synthetic construct
SEQUENCE: 19
ccggagacgt gtggactgtt ataagctcga gcttataaca gtccacacgt ctttttg       58
```